US010662458B2

(12) United States Patent
Liu et al.

(10) Patent No.: US 10,662,458 B2
(45) Date of Patent: *May 26, 2020

(54) METHODS AND MATERIALS FOR BIOSYNTHESIS OF MOGROSIDE COMPOUNDS

(71) Applicant: EVOLVA SA, Reinach (CH)

(72) Inventors: Yaoquan Liu, Palo Alto, CA (US); Jorgen Hansen, Frederiksberg (DK); Jens Houghton-Larsen, Birkerod (DK); Muthuswamy Panchapagesa Murali, Chennai (IN); Sathish Kumar, Tamil Nadu (IN); Nina Nicoline Rasmussen, Hvidor (DK)

(73) Assignee: EVOLVA SA, Reinach (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/900,557

(22) Filed: Feb. 20, 2018

(65) Prior Publication Data

US 2018/0251806 A1 Sep. 6, 2018

Related U.S. Application Data

(62) Division of application No. 14/442,694, filed as application No. PCT/EP2013/075510 on Dec. 4, 2013, now Pat. No. 9,932,619.

(60) Provisional application No. 61/733,220, filed on Dec. 4, 2012.

(51) Int. Cl.
| | |
|---|---|
| *C12P 19/18* | (2006.01) |
| *C12P 33/20* | (2006.01) |
| *C12N 9/10* | (2006.01) |
| *C12P 19/56* | (2006.01) |
| *C12P 33/08* | (2006.01) |
| *C12N 9/02* | (2006.01) |
| *C12N 9/14* | (2006.01) |
| *C12N 9/90* | (2006.01) |
| *C12P 33/00* | (2006.01) |
| *C12P 33/12* | (2006.01) |
| *C12N 15/80* | (2006.01) |

(52) U.S. Cl.
CPC ............ *C12P 33/20* (2013.01); *C12N 9/0071* (2013.01); *C12N 9/0073* (2013.01); *C12N 9/1048* (2013.01); *C12N 9/14* (2013.01); *C12N 9/90* (2013.01); *C12P 19/18* (2013.01); *C12P 19/56* (2013.01); *C12P 33/00* (2013.01); *C12P 33/08* (2013.01); *C12P 33/12* (2013.01); *C12Y 114/00* (2013.01); *C12Y 303/00* (2013.01); *C12Y 504/99033* (2013.01); *C12N 15/80* (2013.01); *C12Y 114/13132* (2013.01)

(58) Field of Classification Search
CPC ........................................................ C12P 33/20
USPC ......................................................... 435/97
See application file for complete search history.

(56) References Cited

U.S. PATENT DOCUMENTS

| 8,257,948 B1 | 9/2012 | Markosyan |
| 9,932,619 B2 * | 4/2018 | Liu .................... C12P 33/20 |
| 10,011,859 B2 * | 7/2018 | Liu .................... C12P 19/18 |
| 2007/0118916 A1 | 5/2007 | Puzio et al. |
| 2015/0322473 A1 | 11/2015 | Liu et al. |

FOREIGN PATENT DOCUMENTS

| EP | 1510573 | 3/2005 |
| EP | 1897951 | 12/2010 |
| WO | WO 2001/012845 | 2/2001 |
| WO | WO 0112845 | 2/2001 |
| WO | WO 2008/062165 | 5/2008 |
| WO | WO 2008/065370 | 5/2008 |
| WO | WO 2010/106318 | 9/2010 |
| WO | WO 2011/153378 | 12/2011 |
| WO | WO 2013/076577 | 5/2013 |
| WO | WO 2014/086842 | 6/2014 |

OTHER PUBLICATIONS

Bateman et al., "Pfam 3.1: 1313 multiple alignments and profile HMMs match the majority of proteins," Nucl Acids Res. 27(1):260-2 (1999).
Bowles et al., "Glycosyltransferases: manages of small molecules," Curr Opin Plant Biol. 8(3):254-63 (2005).
Brochado et al., "Improved vanillin production in baker's yeast through in silico design," Microb Cell Fact. 9:84 (2010).
Chatuvedula & Prakash, "Cucurbitane glycosides from Siraitia grosvenorii," J Carbohydrate Chem. 30(1):16-26 (2011).
Chiu et al., "Biotransformation of mogrosides from Siraitia grosvenorii Swingle by *Saccharomyces cerevisiae*," J Agric Food Chem. 61(29):7127-34 (2013).
Donald et al., "Effects of overproduction of the catalytic domain of 3-hydroxy-3-methylglutaryl coenzyme A reductase on squalene synthesis in *Saccharomyces cerevisiae*," Appl Environ Microbiol. 63(9):3341-4 (1997).
Guo et al., "Protein tolerance to random amino acid change," Proc Natl Acad Sci U 22;101(25):9205-10 (2004).
Hamberger & Bak, "Plant P450s as versatile drivers for evolution of species-specific chemical diversity," Philos Trans R Soc Lond B Biol Sci. 368(1612):20120426 (2013).
Jia & Yang, "A minor, sweet cucurbitane glycoside from Siraitia grosvenorii," Nat Prod Commun. 4(6):769-72 (2009).
Kasai et al., "Sweet cucurbitane glycosides from fruits of Siraitia siamensis (chi-zi luo-han-guo), a Chinese folk medicine," Agric Biol Chem. 53(12):3347-9 (1989).
Kirby et al., "Engineering triterpene production in *Saccharomyces cerevisiae*-beta-amyrin synthase from Artemisia annua," FEBS J. 275(8):1852-9 (2008).

(Continued)

*Primary Examiner* — Tekchand Saidha
(74) *Attorney, Agent, or Firm* — McDonnell Boehnen Hulbert & Berghoff LLP

(57) ABSTRACT

The invention relates to methods for producing mogrosides with the aid of enzymes. In particular the invention proposes various biosynthetic pathways useful for mogroside production and enzymes useful for mogroside production are provided. Furthermore, the invention provides recombinant hosts useful in performing the methods of the invention.

19 Claims, 32 Drawing Sheets

Specification includes a Sequence Listing.

(56) References Cited

OTHER PUBLICATIONS

Li et al. "Cucurbitane glycosides from unripe fruits of Lo Han Kuo (Siraiitia grosvenori)," Chem Pharm Bull (Tokyo) 54(10):1425-8 (2006).
Matsumoto, "Minor cucurbitane-glycosides from fruits of Siraitia grosvenorii (Cucurbitaceae)," Chem Pharm Bull. 38(7):2030-2 (1990).
Nilsson et al., "Chemical synthesis of proteins," Annu Rev Biophys Biomol Struct. 34: 91-118 (2005).
Poppenberger et al., "Heterologous expression of Arabidopsis UDP-glucosyltransferases in Saccharomyces cerevisiae for production of zearalenone-4-O-glucoside," Appl Environ Microbiol. 72(6):4404-10 (Jun. 2006).
Richman, Functional genomics uncovers three glucosyltransferases involved in the synthesis of the major sweet glucosides of Stevia rebaudiana, Plant J. 41(1):56-67 (2005).
Seki, Licorice beta-amyrin 11-oxidase, a cytochrome P450 with a key role in the biosynthesis of the triterpene sweetener glycyrrhizin, Proc Natl Acad Sci U S A. 105(37):14204-9 (2008).
Shao et al., "Crysal structures of a multifunctional triterpene/flavonoid glycosyltransferase from Medicago truncatula," Plant Cell. 17(11):3141-54 (Nov. 2005).
Shibuya et al., "Cucurbitadienol synthase, the first committed enzyme for cucurbitacin biosynthesis, is a distinct anzyme from cycloartenol synthase for phytosterol biosynthesis," Tetrahedron 60(33):6995-7003 (2004).
Sonnhammer et al., "Pfam: a comprehensive database of protein domain families based on seed alignments," Proteins 28(3):405-20 (1997).
Sonnhammer et al., "Pfam: multiple sequence alignments and HMM-profiles of protein domains," Nucl Acids Res. 26(1):320-2 (1998).
Takemoto et al., "Studies on the constituents of Fructus Momordicae. I. On the sweet principle," Yakugaku Zasshi 103(11):1151-4 (1983).
Takemoto et al., "Studies on the constituents of Fructus Momordicae. II. Structure of sapogenin," Yakugaku Zasshi 103(11):1155-66 (1983).
Takemoto et al., "Studies on the constituents of Fructus Momordicae. III. Structures of mogrosides," Yakugaku Zasshi 103(11):1167-73 (1983).
Tang et al., "An efficient approach to finding Siraitia grosvenorii triterpene biosynthetic genes by RNA-seq and digital gene expression analysis," BMC Genomics 12:343, p. 1-13 (2011).
Thompson et al., "Clustal W: improving the sensitivity of progressive multiple sequence alignment through sequence weighting, position-specific gap penalties and weight matrix choice," Nucleic Acids Res. 22(22):4673-80 (1994).
Ukiya et al., "Inhibitory effects of cucurbitane glycosides and other triterpenoids from the fruit of Momordica grosvenori on epstein-barr virus early antigen induced by tumor promoter 12-O-tetradecanoylphorbol-13-acetate," J Agric Food Chem. 50(23):6710-5 (2002).
Xiong Mian-jing et al., "Biosynthesis of triterpene glycoside in Lo Han Kuo," Guangdong Pharmaceutical University 27(5):544-5 (2011). English abstract provided.
Wikipedia: "Mogroside," Internet Archive Wayback Machine Jan. 9, 2014 (Jan. 9, 2014), retrieved from the Internet: URL:https://web.archive.org/web/20140109130110/http://en.wikipedia.org/wiki/Mogroside [retrieved on Apr. 14, 2016] (pp. 1-2).
International Search Report issued by the International Searching Authority for International Application No. PCT/EP2013/075510, dated May 4, 2015 (pp. 1-7).
Written Opinion of the International Searching Authority for International Application No. PCT/EP2013/075510, dated Apr. 23, 2014 (pp. 1-14).
Written Opinion of the International Preliminary Examining Authority for International Application No. PCT/EP2013/075510, dated Feb. 4, 2015 (pp. 1-14).
Written Opinion of the International Preliminary Examining Authority for International Application No. PCT/EP2013/075510, dated May 5, 2015 (pp. 1-15).
International Preliminary Report on Patentability issued by the International Preliminary Examining Authority for International Application No. PCT/EP2013/075510, dated Jul. 23, 2015 (pp. 1-15).
Non-Final Office Action for U.S. Appl. No. 14/504,109, dated Jun. 29, 2016, pp. 1-13.
Final Office Action for U.S. Appl. No. 14/504,109, dated Sep. 8, 2016, pp. 1-18.
International Search Report and Written Opinion of the International Searching Authority for International Application No. PCT/EP2015/072645, dated May 20, 2016 (pp. 1-39).
Non-Final Office Action for U.S. Appl. No. 14/442,694, dated May 16, 2017, pp. 1-13.
International Search Report issued by the International Searching Authority for International Application No. PCT/IB2012/002857, dated May 14, 2013 (pp. 1-6).
Written Opinion of the International Searching Authority for International Application No. PCT/IB2012/002857, dated May 14, 2013 (pp. 1-7).
International Preliminary Report on Patentability issued by the International Preliminary Examining Authority for International Application No. PCT/IB2012/002857, dated Jan. 9, 2014 (pp. 1-13).
Non-Final Office Action for U.S. Appl. No. 14/356,782, dated Oct. 30, 2015 (pp. 1-12).
Final Office Action for U.S. Appl. No. 14/356,782, dated Jul. 18, 2016, pp. 1-16.
Response to Non-Final Office Action for U.S. Appl. No. 14/356,782, filed Mar. 22, 2016 (pp. 1-10).
UniProt Database Accession No. AT223684, "Stevia rebaudiana protein SEQ ID No. 10008," Feb. 3, 2011 (1 page).
GenBank Accession No. XP_008442743; last accessed Apr. 28, 2016 (pp. 1-2).
GenBank Accession No. XP_008450117; last accessed Apr. 28, 2016 (p. 1-2).
GenBank Accession No. XP_008454322; last accessed Apr. 21, 2016 (pp. 1-2).
UniProt Accession No. F6GXH0; last accessed Apr. 21, 2016 (pp. 1-2).
UniProt Accession No. F6HIX7; last accessed Apr. 28, 2016 (pp. 1-2).
UniProt Accession No. K7NBR2; last accessed Apr. 29, 2016 (p. 1).
UniProt Accession No. K7NBZ9; last accessed Apr. 21, 2016 (p. 1).
UniProt Accession No. W7PH03; last accessed Apr. 28, 2016 (p. 1).
UniProt Accession No. W9SCC7; last accessed Apr. 21, 2016 (p. 1).
UniProt Accession No. K7NBX0; last accessed Nov. 29, 2016 (pp. 1-4).
GenBank Accession No. AAS01524, dated Jul. 6, 2009 (pp. 1-2).
GenBank Accession No. ADC84219, dated Mar. 21, 2011 (pp. 1-2).
GenBank Accession No. BAA33460, dated Oct. 3, 1998 (pp. 1-2).
GenBank Accession No. BAA76902, dated Dec. 14, 2001 (pp. 1-2).
GenBank Accession No. BAB83085, dated Aug. 15, 2009 (pp. 1-2).
GenBank Accession No. BAB83086, dated Aug. 15, 2009 (pp. 1-2).
GenBank Accession No. BAD34645.1, dated Mar. 11, 2010 (pp. 1-2).
GenBank Accession No. BAE53431, dated Apr. 20, 2006 (pp. 1-2).
GenBank Accession No. XP_002264289, dated Dec. 10, 2014 (pp. 1-2).
GenBank Accession No. XP_002310905, dated Dec. 31, 2013 (pp. 1-2).
Qiao et al., "Identification of a Novel Specific Cucurbitadienol Synthase Allele in Siraitia grosvenorii Correlates with High Catalytic Efficiency," Molecules. 24(3) (2019).
UniProt Accession No. A7VJN1 (pp. 1-5), dated Oct. 23, 2007.
UniProt Accession No. B5AID3, dated Sep. 23, 2008.
UniProt Accession No. B5AID4 (pp. 1-4), dated Sep. 23, 2008.
UniProt Accession No. B5AID5 (pp. 1-4), dated Sep. 23, 2008.
UniProt Accession No. B9R6V0 (pp. 1-5), dated Mar. 24, 2009.
UniProt Accession No. B9RHC3 (pp. 1-6), dated Mar. 24, 2009.
UniProt Accession No. B9S6Y2 (pp. 1-5), dated Mar. 24, 2009.
UniProt Accession No. B9S7T0 (pp. 1-5), dated Mar. 24, 2009.

(56) References Cited

OTHER PUBLICATIONS

UniProt Accession No. B9S7W5 (pp. 1-5), dated Mar. 24, 2009.
UniProt Accession No. B9SX91 (pp. 1-6), dated Mar. 24, 2009.
UniProt Accession No. B9T0Y3 (pp. 1-5), dated Mar. 24, 2009.
UniProt Accession No. B9WZW7 (pp. 1-5), dated Apr. 14, 2009.
UniProt Accession No. C4P9M2 (pp. 1-5), dated Jul. 7, 2009 (pp. 1-5).
UniProt Accession No. C4P9M3, dated Jul. 7, 2009 (pp. 1-5).
UniProt Accession No. C6KE07, dated Sep. 1, 2009 (pp. 1-5).
UniProt Accession No. C6KE08, dated Sep. 1, 2009 (pp. 1-5).
UniProt Accession No. C7EDC9, dated Sep. 22, 2009 (pp. 1-5).
UniProt Accession No. C7EDD0, dated Sep. 22, 2009 (pp. 1-5).
UniProt Accession No. D6QX35, dated Jul. 13, 2010 (pp. 1-5).
UniProt Accession No. D6QX37, dated Jul. 13, 2010 (pp. 1-5).
UniProt Accession No. D6QX38, dated Jul. 13, 2010 (pp. 1-5).
UniProt Accession No. D6QX39, dated Jul. 13, 2010 (pp. 1-5).
UniProt Accession No. D6QX40, dated Jul. 13, 2010 (pp. 1-5).
UniProt Accession No. D6QX41, dated Jul. 13, 2010 (pp. 1-5).
UniProt Accession No. D6QX42, dated Jul. 13, 2010 (pp. 1-5).
UniProt Accession No. D6QX43, dated Jul. 13, 2010 (pp. 1-5).
UniProt Accession No. D6QX44, dated Jul. 13, 2010 (pp. 1-5).
UniProt Accession No. D6QX45, dated Jul. 13, 2010 (pp. 1-5).
UniProt Accession No. D6QX47, dated Jul. 13, 2010 (pp. 1-5).
UniProt Accession No. D6QX53, dated Jul. 13, 2010 (pp. 1-5).
UniProt Accession No. D6QX55, dated Jul. 13, 2010 (pp. 1-5).
UniProt Accession No. O65402, dated Aug. 1, 1998 (pp. 1-9).
UniProt Accession No. O65403, dated Aug. 1, 1998 (pp. 1-10).
UniProt Accession No. O65404, dated May 30, 2000 (pp. 1-10).
UniProt Accession No. O65726, dated May 30, 2000 (pp. 1-7).
UniProt Accession No. O65727, dated Aug. 1, 1998 (pp. 1-7).
UniProt Accession No. O81000, dated Nov. 1, 1998 (pp. 1-9).
UniProt Accession No. Q42760, dated Nov. 1, 1996 (pp. 1-5).
UniProt Accession No. Q42761, dated Nov. 1, 1996 (pp. 1-5).
UniProt Accession No. Q84LE3, dated Jun. 1, 2003 (pp. 1-5).
UniProt Accession No. Q8GSL6, dated Mar. 1, 2003 (pp. 1-6).
UniProt Accession No. Q8GSM8, dated Mar. 1, 2003 (pp. 1-5).
UniProt Accession No. Q8GSM9, dated Mar. 1, 2003 (pp. 1-5).
UniProt Accession No. Q9SM02, dated May 1, 2000 (pp. 1-11).
UniProt Accession No. Q9T064 (Q8VYH2), dated Mar. 1, 2002 (pp. 1-10).

\* cited by examiner

```
  1  mvrlkvqsss vqssdskwvk svsnhlgrqv wsfcadssad tphqllqtqn srnhfhhnrf
 61  hckqssdlfl aiqyskslsk gskggsrkvk sgssvqksav katlsralgf ysvvqtrdgs
121  wssdlgpplf llpglvislh vtgvlnsvls khhrvsscry lynhqssdgg wglhisgtst
181  sfgsslnyvs lrllgsdsdg yqggsstksr swilsrggst sitssgklwl svlgvysssg
241  ssplppsfwl lpyslpfhpg sswchsrswy lpssylygks fvgpitpkvl slrqslytip
301  yhsldwnksr ntcsksdlyy phpksqdilw gslyhvyspl ftrspgkrlr skslqsssth
361  lhysdsnsry lclgpvnkvl nnlccwvsdp ysdsfklhlq rvhdylwvss dgsrsqgyng
421  sqlwdtsfsl qslvstklvd syspsltrksh dfvkdsqlqs dcpgdpsvwf rhlhkgsvpl
481  strdhqvlls dctssglkss lnlsklpsts vgsplsknrl cdsvnvllsl qsdnggfssy
541  slsrsypwls llcpsstfgd lvldypyvss tsstsssltl fkklhpghst ksldtslgks
601  snflskmgrs dgssyqcsgv cftysgwfgl kglvssgrty ssclslrtsc sflloksslpg
661  ggsgssylsc qskvytslsg nkphlvntss vlsslissgq gsrdpsplhr ssrllsssql
721  ssgdfvqgsl sgvfsksssl tysayrslfp lsslgsychr vlts (SEQ ID NO:1).
```

FIG.14

CYP533 (SEQ ID NO:3)
ATGGAACTCTTCTCTACCAAAACTGCAGCCGAGATCATCGCTGTTGTCTTGTTTTTCTACGCTCT
CATCCGGCTATTATCTGGAAGATTCAGCTCTCAACAGAAGAGACTGCCACCTGAAGCCGGTGGCG
CCTGGCCACTGATCGGCCATCTCCATCTCCTAGGTGGGTCGGAACCTGCACATAAAACCTTGGCG
AACATGGCGGACGCCTACGGACCAGTTTTTACGTTGAAACTGGGCATGCATACAGCTTTGGTTAT
GAGCAGTTGGGAAATAGCGAGAGAGTGCTTTACTAAAACGACAGAATCTTTGCCTCCCGCCCCA
TAGTCACTGCCTCAAAGCTTCTCACCTATAACCATACCATGTTTGGGTTCAGCCAATATGGTCCA
TTCTGGCGCCATATGCGCAAATAGCCACGCTTCAACTCCTCTCAAACCACCGCCTCGAGCAGCT
CCAACACATCAGAATATCGGAGGTCCAGACTTCGATTAAGAAACTGTACGAGTTGTGGGTCAACA
GCAGAAATAATGGAGGCGAGAAAGTGTTGGTGGAGATGAAGACGTGGTTCGGAGGCATAACCTTG
AACACCATATTCAGGATGGTGGTCGGAAAGCGATTCTCGACTGCTTTCGAAGGCAGTGGTGGCGA
ACGGTATCGGAAGGCGTTGAGGGATTCTCTTGAATGGTTTGGGGCATTCGTTCCGTCAGATTCAT
TCCCGTTTTTAAGATGGTTGGATTTGGGAGGATATGAGAAGGCGATGAAGAAGACGGCGAGTGTG
CTGGACGAGGTGCTTGATAAATGGCTCAAAGAGCATCAGCAGAGGAGAAACTCCGGTGAACTGGA
GACGGAGGAGCACGACTTCATGCACGTGATGCTGTCTATTGTTAAGGATGATGAAGAACTATCCG
GCTACGATGCCGATACAGTCACAAAAGCTACATGTTTGAATTTAATAGTTGGTGGATTCGACACT
ACACAAGTAACTATGACATGGGCTCTTTCTTTGCTTCTCAACAATGAAGAGGTATTAAAAAGGC
CCAACTTGAACTAGACGAACAAGTTGGAAGAGAGAGGTTTGTGGAAGAGTCCGATGTTAAAAATC
TGTTATATCTCCAGGCCATCGTGAAGGAAACTTTGCGTTTGTACCCTTCAGCGCCAATCTCGACA
TTTCATGAGGCCATGGAAGATTGCACTGTTTCTGGCTACCACATCTTTTCAGGGACGCCTTTGAT
GGTGAATCTTCAAAAGCTTCAAAGAGATCCACTTGCATGGGAGGATCCATGTGACTTTCGACCGG
AGAGATTTCTGACAACTCATAAGGATTTCGATCTTAGAGGACATAGTCCTCAATTGATACCATTT
GGGAGTGGTCGAAGAATATGCCCTGGCATCTCGTTTGCCATTCAAGTTTTGCATCTTACGCTTGC
AAATCTACTTCATGGGTTTGACATTGGAAGGCCATCTCATGAACCAATCGATATGCAGGAGAGTA
AAGGACTAACGAGTATTAAAACAACTCCACTTGAGGTTGTTTTAGCTCCACGCCTTGCTGCTCAA
GTTTATGAGTGA

CYP937 (SEQ ID NO:4)
ATGCCGATCGCAGAAGGTGCAGTCTCTGATTTGTTTGGTCGCCCACTCTTCTTTGCACTATATGA
TTGGTTCTTAGAGCATGGATCTGTTTATAAACTTGCCTTTGGACCAAAAGCCTTTGTTGTTGTAT
CAGATCCCATTGTGGCAAGATATATTCTTCGAGAAAATGCATTGGTTATGACAAGGGAGTGCTT
GCTGATATTTAGAACCGATAATGGGTAAAGGACTAATACCAGCTGACCTTGGCACTTGGAAGCA
GAGGAGACGAGTTATTGCTCCAGGATTCCATGCCTTGTACTTGGAAGCTATGACCAAAGTATTTG
CCAATTGTTCAGAACGATCAATATTGAAATTGGAGAAGCTTCTAGGAGAAGGTGAACTACAGGAG
AATAAACCATTGAGTTGGATATGGAAGCAGAGTTTCAAGTTTGGCTCTTGATATCATTGGACT
CGGTGTTTTCAACTATGATTTTGGTTCTGTAACCAAAGAATCTCCGGTGATTAAGGCTGTATATG
GGACTCTTTTTGAAGCAGAGCATAGATCGACTTTCTATATCCCATATTGGAAAGTACCTTTGGCA
AGGTGGATAGTCCCAAGGCAGCGTAAATTCCATGGTGACCTTAAGGTTATTAATGAGTGTCTTGA
TGGCCTAATACGCAACGCAAGAGAAACCCGAGACGAAACGGATGTTGAGAAATTGCAGCAAAGGG
ACTACTTAAATCTCAAGGATGCCAGTCTTTTGCGTTTCTTAGTTGATATGCGGGGAGCTGATGTT
GATGATCGCCAGCTTAGGGACGATCTGATGACGATGCTTATTGCTGGCCATGAAACAACTGCTGC
TGTGCTTACATGGGCTGTTTTTTTGCTTGCACAAAATCCTTCAAAAATGAAAAAGCGCAAGCAG
AGATTGATTTGGTTCTTGGCATGGGGAGGCCAACTTTTGAATCATTAAAGCATTGAAGTACATC
AGACTTATCGTTGCAGAGACTCTTCGTTTGTTTCCTCAGCCTCCATTGCTGATAAGACGAGCTCT
CAAATCAGATATATTACCAGGAGGATACAATGGTGACAAAACTGGATATGCAATTCCTGCAGGGA
CTGACATCTTCATCTCTGTTTACAATCTCCACAGATCTCCCTACTTCTGGGATAATCCTCAAGAA
TTGAACCAGAGAGATTTCAAGTAAAGAGGGCAAGCGAGGGAATTGAAGGATGGGATGGTTTCGA
CCCATCTAGAAGCCCTGGAGCTCTATACCCGAATGAGATTGTAGCAGACTTTTCCTTCTTACCAT

FIG.15

TTGGTGGAGGCCCTAGAAAATGTGTGGGAGATCAATTTGCTCTAATGGAGTCAACTATAGCATTG
GCCATGTTACTGCAGAAGTTTGATGTGGAGCTAAAAGGAAGTCCAGAATCTGTAGAACTAGTTAC
TGGAGCCACAATACATACCAAAAGTGGGTTGTGGTGCAAACTGAGAAGAAGATCACAAGTAAACT
GA

CYP1798 (SEQ ID NO:5)
ATGGAAATGTCCTCAAGTGTCGCAGCCACAATCAGTATCTGGATGGTCGTCGTATGTATCGTAGG
TGTAGGTTGGAGAGTCGTAAATTGGGTTTGGTTGAGACCAAAGAAATTGGAAAAGAGATTGAGAG
AACAAGGTTTGGCCGGTAATTCTTACAGATTGTTGTTCGGTGACTTGAAGGAAAGAGCTGCAATG
GAAGAACAAGCAAATTCAAAGCCTATAAACTTCTCCCATGACATCGGTCCAAGAGTTTTCCCTTC
AATGTACAAGACCATCCAAAACTACGGTAAAAACTCCTACATGTGGTTAGGTCCATACCCTAGAG
TCCACATCATGGATCCACAACAATTGAAGACCGTTTTTACTTTGGTCTACGACATTCAAAAGCCA
AATTGAACCCTTTGATTAAATTCTTGTTAGATGGTATCGTTACACATGAAGGTGAAAAGTGGGC
TAAGCACAGAAAGATTATTAACCCAGCATTCCATTTGGAAAAGTTGAAGGATATGATACCTGCTT
TCTTTCACTCATGTAATGAAATCGTCAACGAATGGAAAGATTGATTTCAAAAGAAGGTTCCTGC
GAATTGGATGTAATGCCTTATTTGCAAAATTTGGCCGCTGACGCCATTTCAAGAACCGCTTTTGG
TTCTTCATACGAAGAAGGTAAAATGATCTTCCAATTGTTGAAGGAATTGACTGATTTGGTTGTCA
AGGTAGCTTTTGGTGTTTATATTCCAGGTTGGAGATTCTTGCCTACAAAGAGTAACAACAAAATG
AAGGAAATTAATAGAAAAATCAAGTCTTTGTTGTTGGGTATCATTAACAAGAGACAAAAGGCAAT
GGAAGAAGGTGAAGCCGGTCAATCTGATTTGTTGGCTATATTAATGGAAAGTAATTCTAACGAAA
TCCAAGGTGAAGGTAATAACAAGGAAGATGGCATGTCTATTGAAGACGTCATCGAAGAGTGTAAG
GTATTTTATATAGGTGGTCAAGAAACTACAGCAAGATTATTGATCTGGACTATGATATTGTTGTC
CAGTCATACAGAATGGCAAGAAAGAGCCAGAACCGAAGTCTTGAAGGTATTTGGTAATAAGAAAC
CAGATTTCGACGGTTTGTCAAGATTGAAGGTAGTTACTATGATCTTGAACGAAGTTTTAAGATTG
TACCCACCTGCTTCCATGTTGACAAGAATCATCCAAAAGGAAACAAGAGTTGGTAAATTAACCTT
GCCAGCAGGTGTTATCTTGATAATGCCTATCATCTTGATACATAGAGATCACGACTTGTGGGGTG
AAGATGCTAACGAGTTTAAACCAGAAAGATTCAGTAAAGGTGTTTCTAAGGCAGCCAAAGTCCAA
CCAGCCTTTTTCCCTTTTGGTTGGGGTCCTAGAATTTGCATGGGTCAAAACTTCGCTATGATCGA
AGCTAAGATGGCATTGAGTTTGATCTTGCAAAGATTTTCTTTCGAATTGTCTTCATCCTACGTTC
ATGCACCAACTGTCGTCTTCACTACACAACCACAACACGGTGCCCACATCGTTTTGAGAAAGTTA
TGA

CYP1994 (SEQ ID NO:6)
ATGGAACCACAACCAAGTGCCGGAATTCAACTGGAATCACAGCCTAAGCACCGTCGCTATCGGTGT
CATTGCCATTATTTTCTTCCGTTTTCTCGTCAAAAGAGTCACCGGCGCCGGTGAGCGAAAGGGTC
CGAAGCCGCCAAAAGTAGCCGGAGGGTGGCCTCTAATTGGCCACCTCCCTCTCCTCGGAGGACCT
GAACTGCCCCATGTCAAACTGGGTGGTTTGGCTGATAAATATGGTCCAATCTTCTCGATCCGGCT
GGGTGTCCACTCCGCCGTCGTGATAAACAGTTGGGAGGCGGCGAAACAGTTATTAACCAACCATG
ACGTCGCCGTCTCTTCCCGCCCCCAAATGCTCGGCGGAAAACTCCTGGGCTACAACTACGCCGTG
TTTGGTTTCGGACCCTACGGCTCTTACTGGCGCAACATGCGCAAGATAACCACGCAAGAGCTTCT
ATCCAATAGCAGAATCCAGCTCCTAAGAGACGTTCGAGCGTCAGAAGTGAACCAAGGCATAAAAG
AGCTCTACCAGCACTGGAAAGAAAGAAGAGACGGTCACGACCAAGCCTTGGTGGAACTGCAGCAG
TGGGTCGGGGACTTGACTATGAATCTGATTCTCGGAGTCATCGCCGGGAAAAGGTTCTTTGGAGC
TGCAGCAACGGTAGACGAGGAAGAGGCGCGACGGAGCCATAAAGCATTGAAGGAGTTGTTACATT
ATATGGGGCTTTTTCTACTGGGTGATGCTGTTCCATATCTAGGATGGTTGGACGTCGGCGGCCAT
GTGAAGGCGATGAAGAAAACTTCAAAAGAATTGGACCGTATGTTAACACAGTGGTTGGAGGAGCA
CAAGAAGGAAGGACCCAAGAAAGATCATAAAGACTTCATGGACGTGATGCTTTCAGTTCTCAATG
AAACATCCGATGTTCTTTCAGATAAGACCCATGGCTTCGATGCTGATACCATCATCAAAGCTACA
TGTATGACGATGGTTTTAGGAGGGAGTGATACGACGGCGGTGGTTGTGATATGGGCAATCTCGCT
GCTGCTGAATAATCGCCCTGCGTTGAGAAAAGTGCAAGAAGAACTGGAAGCCCATATCGGCCGAG
ACAGAGAACTGGAGGAATCGGATCTCGGTAAGCTAGTGTATTTGCAGGCAGTCGTGAAGGAGACA
TTGCGGCTGTACGGAGCCGGAGGCCTTTTCTTTCGTGAAACCACAGAGGATGTCACCATCGACGG

FIG.15 (CONT.)

ATTCCATGTCGAGAAAGGGACATGGCTGTTCGTGAACGTGGGGAAGATCCACAGAGATGGGAAGG
TGTGGCCGGAGCCAACGGAGTTCAAACCGGAGAGGTTTCTGACGACCCACAAAGATTTTGATCTG
AAGGGCCAGCGGTTTGAGCTCATCCCTTTCGGGGGAGGAAGAAGATCGTGCCCCTGGAATGTCTTT
TGGGCTCCAAAATGCTACAGCTTATTTTGGGTAAACTGCTTCAGGCTTTTGATATATCGACGCCGG
GGGACGCCGCCGTTGATATGACCGGATCCATTGGACTGACGAACATGAAAGCCACTCCATTGGAA
GTGCTCATCACCCCGCGCTTGCCTCTTTCGCTTTACGATTGA

CYP2048 (SEQ ID NO:7)
ATGGAGACTCTTCTTCTTCATCTTCAATCGTTATTTCATCCAATTTCCTTCACTGGTTTCGTTGT
CCTCTTTAGCTTCCTGTTCCTGCTCCAGAAATGGTTACTGACACGTCCAAACTCTTCATCAGAAG
CCTCACCCCCTTCTCCACCAAAGCTTCCCATCTTCGGACACCTTCTAAACCTGGGTCTGCATCCC
CACATCACCCTCGGAGCCTACGCTCGCCGCTATGGCCCTCTCTTCCTCCTCCACTTCGGCAGCAA
GCCCACCATCGTCGTCTCTTCTGCCGAAATCGCTCGCGATATCATGAAGACCCACGACCTCGTCT
TCGCCAACCGTCCTAAATCAAGCATCAGCGAAAAGATTCTTTACGGCTCCAAAGATTTAGCCGCA
TCTCCTTACGGCGAATACTGGAGGCAGATGAAAAGCGTTGGCGTGCTTCATCTTTTGAGCAACAA
AAGGGTTCAATCCTTTCGCTCTGTCAGAGAAGAAGAAGTCGAACTGATGATCCAGAAGATCCAAC
AGAACCCCCTATCAGTTAATTTAAGCGAAATATTCTCTGGACTGACGAACGACATAGTTTGCAGG
GTGGCTTTAGGGAGAAAGTATGGCGTGGGAGAAGACGGAAAGAAGTTCCGGTCTCTTCTGCTGGA
GTTTGGGGAAGTATTGGGAAGTTCAGTACGAGAGACTTCATCCCGTGGCTGGGTTGGATTGATC
GTATCAGTGGGCTGGACGCCAAAGCCGAGAGGGTAGCCAAAGAGCTCGATGCTTTCTTTGACAGA
GTGATCGAAGATCACATCCATCTAAACAAGAGAGAGAATAATCCCGATGAGCAGAAGGACTTGGT
GGATGTGCTGCTTTGTGTACAGAGAAGACTCCATCGGGTTTCCCCTTGAGATGGATAGCATAA
AAGCTTTAATCTTGGACATGTTTGCTGCAGGCACAGACACGACATACACGGTGTTGGAGTGGGCA
ATGTCCCAACTGTTGAGACACCCAGAAGCGATGAAGAAACTGCAGAGGGAGGTCAGAGAAATAGC
AGGTGAGAAAGAACACGTAAGTGAGGATGATTTAGAAAAGATGCATTACTTGAAGGCAGTAATCA
AAGAAACGCTGCGGCTACACCCACCAATCCCACTCCTCGTCCCCAGAGATCAACCCAAGACATC
AGGTTGAGGGGGTACGATATCAGAGGCGGCACCCGGGTTATGATCAATGCATGGGCCATCGGAAG
A

CYP2740 (SEQ ID NO:8)
ATGTCGATGAGTAGTGAAATTGAAAGCCTCTGGGTTTTCGCGCTGGCTTCTAAATGCTCTGCTTT
AACTAAAGAAAACATCCTCTGGTCTTTACTCTTCTTTTTCCTAATCTGGGTTTCTGTTTCCATTC
TCCACTGGGCCCATCCGGGCGGCCCGGCTTGGGGCCGCTACTGGTGGCGCCGCCGCCGCAGCAAT
TCCACCGCCGCTGCTATTCCCGGCCCGAGAGGCCTCCCCCTCGTCGGCAGCATGGGCTTGATGGC
CGACTTGGCCCACCACCGGATTGCCGCCGTGGCTGACTCCTTAAACGCCACCCGCCTCATGGCCT
TTCGCTCGGCACACTCGCGTGATCGTCACATGCAACCCCGACGTCGCCAAAGAGATTCTCAAC
AGCTCCCTCTTCGCCGACCGCCCCGTTAAGGAGTCCGCTTACTCCTTGATGTTCAACCGCGCCAT
TGGGTTCGCCCCTATGGCCTTTACTGGCGGACCCTCCGCCGCATCGCTTCCCACCACCTCTTCT
GCCCCAAGCAAATCAAGTCCTCCCAGTCCCAGCGCCGCCAAATCGCTTCCCAAATGGTCGCAATG
TTCGCAAACCGCGATGCCACACAGAGCCTCTGCGTTCGCGACTCTCTCAAGCGGGCTTCTCTCAA
CAACATGATGGGCTCTGTTTTCGGCCGAGTTTACGACCTCTCTGACTCGGCTAACAATGACGTCC
AAGAACTCCAGAGCCTCGTCGACGAAGGCTACGACTTGCTGGGCCTCCTCAACTGGTCCGACCAT
CTCCCATGGCTCGCCGACTTCGACTCTCAGAAAATCCGGTTCAGATGCTCCCGACTCGTCCCCAA
GGTGAACCACTTCGTCGGCCGGATCATCGCCGAACACCGCGCCAAATCCGACAACCAAGTCCTAG
ATTTCGTCGACGTTTTGCTCTCTCTCCAAGAAGCCGACAAACTCTCTGACTCCGATATGATCGCC
GTTCTTTGGGAAATGATTTTTCGTGGGACGGACACGGTGGCAGTTTTAATCGAGTGGATACTGGC
CAGGATGGTACTTCAACAACGATATCCAAAGGAAAGTTCAAGAGGAGCTAGATAACGTGGTTGGGA
GTACACGCGCCGTCGCGGAATCCGACATTCCGTCGCTGGTGTATCTAACGGCTGTGGTTAAGGAA
GTTCTGAGGTTACATCCGCCGGGCCCACTCCTGTCGTGGGCCCGCCTAGCCATCACTGATACAAT
CATCGATGGGCATCACGTGCCCGGGGGACCACCGCTATGGTTAACATGTGGTCGATAGCGCGGG
ACCCACAGGTCTGGTCGGACCCACTCGAATTTATGCCCCAGAGGTTTGTGTCCGACGCCGGTGAC
GTGGAGTTCTCGGTCATGGGTTCGGATCTCCGGCTGGCTCCGTTCGGGTCGGGCAGAAGGACCTG

CCCCGGGAAGGCCTTCGCCTGGACAACTGTCACCTTCTGGGTGGCCACGGCTTTTACACGACTTCA
AATGGTCGCCGTCCGATCAAAACGACGCCGTCGACTTGTCGGAGGTCCTCAAGCTCTCCTGCGAG
ATGGCCAATCCCCTCACCGTTAAAGTACACCCAAGGCGCAGTTTAAGCTTTTAA

CYP3404 (SEQ ID NO:9)
ATGGATGGTTTTCTTCCAACAGTGGCGGCGAGCGTGCCTGTGGAAGTGGGTGCAATATTGTTCAC
GGCGTTGTGCGTCGTCGTGGGAGGGGTTTTGGTTTATTTCTATGGACCTTACTGGGGAGTGAGAA
GGGTGCCTGGTCCACCAGCTATTCCACTGGTCGGACATCTTCCCTTGCTGGCTAAGTACGGCCCA
GACGTTTCTCTGTCCTTGCCACCCAATATGGCCCTATCTTCAGGTTCCATATGGGTAGGCAGCC
ATTGATAATTATAGCAGACCCTGAGCTTTGTAAAGAAGCTGGTATTAAGAAATTCAAGGACATCC
CAAATAGAAGTGTCCTTCTCCAATATCAGCTTCCCCTCTTCATCAGAAGGGTCTTTTCTTCACA
AGGGATGCAAGATGGTCGACAATGCGGAACACGATATTATCGGTCTATCAGTCCTCCCATCTAGC
GAGACTAATACCTACTATGCAATCAATCATTGAAACTGCAACTCAAAATCTCCATTCCTCTGTCC
AGGAAGACATCCCTTTCTCCAATCTCTCCCTCAAATTGACCACCGATGTGATTGGAACAGCAGCC
TTCGGTGTCAACTTTGGGCTCTCTAATCCACAGGCAACCAAAACTTGTGCTACCAACGGCCAAGA
CAACAAAAATGACGAAGTTTCAGACTTCATCAATCAACACATCTACTCCACAACGCAGCTCAAGA
TGGATTTATCAGGTTCCTTCTCAATCATACTTGGACTGCTTGTCCCTATACTCCAAGAACCATTT
AGACAAGTCCTAAAGAGAATACCATTCACCATGGACTGGAAAGTGGACCCGACAAATCAGAATT
AAGTGGTCGGCTTAATGAGATTGTGGAGAAGAGAATGAAGTGTAACGATCAAGGTTCAAAAGACT
TCTTATCGCTCATTTGAGAGCAAGAGAGTCAGACACAGTATCAAGGAATGTCTTCACTCCAGAC
TACATCAGTGCAGTTACGTATGAACACCTACTTGCTGGGTCGGCTACCACGGCGTTTACGTTGTC
TTCTATTGTATATTTAGTTGCTGGGCATCCAGAAGTCGAGAAGAAGTTGCTAGAAGAGATTGACA
ACTTTGGTCCATCCGATCAGATACCAACAGCTAATGATCTTCATCAGAAGTTTCCATATCTTGAT
CAGGTGATTAAAGAGGCTATGAGGTTCTACACTGTTTCCCTCTAGTAGCCAGAGAAACAGCTAA
AGATGTGGAGATTGGTGGATATCTTCTTCCAAAGGGGACATGGGTTTGGTTAGCACTTGGAGTTC
TTGCCAAGGATCCAAAGAACTTTCCAGAACCAGATAAATTCAAACCAGAGAGGTTTGATCCAAAT
GAAGAAGAGGAGAAACAAAGGCATCCTTATGCTTTAATCCCCCTTTGGAATTGGTCCTCGAGCATG
CATGGTAAAAAATTCGCCCCTTCAGGAGTTGAAGCTCTCGTTGATTCATTTGTACAGGAAGTTTG
TATTTCGGCAT

CYP3969 (SEQ ID NO:10)
ATGGAAATCATTTTATCATATCTCAACAGCTCCATAGCTGGACTCTTCCTCTTGCTTCTCTTCTC
GTTTTTTGTTTTGAAAAAGGCTAGAACCTGTAAACGCAGACAGCCTCCTGAAGCAGCCGGCGGAT
GGCCGATCATCGGCCACCTGAGACTGCTCGGGGGTTCGCAACTTCCCCATGAAACCTTGGGAGCC
ATGGCCGACAAGTATGGACCAATCTTCAGCATCCGAGTTGGTGTCCACCCATCTCTTGTTATAAG
CAGTTGGGAAGTGGCTAAAGAGTGCTACACCACCCTCGACTCAGTTGTCTCTTCTCGTCCCAAGA
GTTTGGGTGGAAAGTTGTTGGGCTACAACTTCGCCGCTTTTGGGTTCAGGCCTTATGATTCCTTT
TACCGGAGTATCCGCAAAACCATAGCCTCCGAGGTGCTGTCGAACCGCCGTCTGGAGTTGCAGAG
ACACATTCGAGTTTCTGAGGTGAAGAGATCGGTGAAGGAGCTTTACAATCTGTGGACGCAGAGAG
AGGAAGGCTCAGACCACATACTTATTGATGCGGATGAATGGATTGGTAATATTAATTTGAACGTG
ATTCTGATGATGGTTTGTGGGAAGCGGTTTCTTGGCGGTTCTGCCAGCGATGAGAAGGAGATGAG
GCGGTGTCTCAAAGTCTCGAGAGATTTCTTCGATTTGACAGGGCAGTTTACGGTGGGAGATGCCA
TTCCTTTCCTGCGATGGCTGGATTTGGGTGGATATGCGAAGGCGATGAAGAAAACTGCAAAAGAA
ATGGACTGTCTCGTTGAGGAATGGCTGGAAGAACACCGCCGGAAGAGAGACTCCGGCGCCACCGA
CGGTGAACGTGACTTCATGGATGTGATGCTTTCGATTCTTGAAGAGATGGACCTTGCTGGCTACG
ACGCTGACACAGTCAACAAAGCCACATGCCTGAGCATTATTTCTGGGGAATCGATACTATAACG
CTAACTCTGACATGGGCGATCTCGTTATTGCTGAACAATCGAGAGGCACTGCGAAGGGTTCAAGA
GGAGGTGGACATCCATGTCGGAAACAAAAGGCTTGTGGATGAATCAGACTTGAGCAAGCTGGTGT
ATCTCCAAGCCGTCGTGAAAGAGACATTAAGGTTGTACCCAGCAGGGCCGCTGTCGGGAGCTCGA
GAGTTCAGTCGGGACTGCACGGTCGGAGGGTATGACGTGGCCGCCGGCACACGGCTCATCACAAA
CCTTTGGAAGATACAGACGGACCCTCGGGTGTGGCCGGAGCCACTTGAGTTCAGGCCGGAGAGGT
TTCTGAGCAGCCACCAGCAGTTGGATGTGAAGGGCCAGAACTTTGAACTGGCCCCATTTGGTTGT

GGAAGAAGAGTGTGCCCTGGGGCGGGGCTTGGGGTTCAGATGACGCAGTTGGTGCTGGCGAGTCT
GATTCATTCGGTGAAACTTGGGACTCGCTCCGATGAAGCGGTGGACATGGCTGCTAAGTTTGGAC
TCACAATGTACAGAGCCACCCCTCTTCAGGCTCTCGTCAAGCCACGGCCTCCAAGCCGGTGCTTAT
TCATGA

CYP4112 (SEQ ID NO:11)
ATGGGTGTATTGTCCATTTTATTATTCAGATATTCCGTCAAGAAGAAGCCATTAAGATGCGGTCA
CGATCAAAGAAGTACCACAGATAGTCCACCTGGTTCAAGAGGTTTGCCATTGATAGGTGAAACTT
TGCAATTCATGGCTGCTATTAATTCTTTGAACGGTGTATACGATTTCGTTAGAATAAGATGTTTG
AGATACGGTAGATGCTTTAAGACAAGAATCTTCGGTGAAACCCATGTTTTTGTCTCAACTACAGA
ATCCGCTAAGTTGATCTTGAAGGATGGTGGTGAAAAATTCACCAAAAAGTACATCAGATCAATCG
CTGAATTGGTTGGTGACAGAAGTTTGTTATGTGCATCTGATTTGCAACACAAGAGATTGAGAGGT
TTGTTGACTAATTTGTTTTCTGCCACATTCTTGGCTTCTTTCGTAACTCAATTCGATGAACAAAT
CGTTGAAGCTTTTAGATCATGGGAATCCGTAGTACCATAATCGTTTTGAACGAAGCATTGAAGA
TCACTTGTAAGGCCATGTGCAAAATGGTCATGTCCTTAGAAAGAGAAAACGAATTGGAAGCTTTG
CAAAAGGAATTGGGTCATGTTTGTGAAGCTATGTTGGCATTTCCATGCAGATTCCCTGGTACAAG
ATTTCACAATGGTTTGAAGGCAAGAAGAAGAATCATTAAAGTTGTCGAAATGCCCATTAGAGAAA
GAAGAAGATCTGAAGCTCCTAGAGAAGATTTCTTGCAAAGATTGTTGACAGAAGAAAAGGAAGAA
GAAGACGGTGGTGGTGTTTTAAGTGATGCCGAAATTGGTGACAACATATTGACAATGATGATCGC
AGGTCAAGATACCACTGCCTCTGCTATTACCTGGATGGTCAAGTTTTTGGAAGAAAACCAAGATG
TATTGCAAAACTTAAGAGACGAACAATTCGAAATCATGGGTAAACAAGAAGGTTGTGGTTCATGC
TTCTTGACATTAGAAGATTTGGGTAATATGTCCTATGGTGCAAAAGTAGTTAAGGAATCATTGAG
ATTAGCCTCCGTCGTACCATGGTTTCCTAGATTGGTTTTACAAGATTCTTTGATCCAAGGTTACA
AAATTAAAAAGGGTTGGAACGTCAACATAGACGTAAGATCTTTACATTCAGATCCATCCTTGTAT
AATGACCCAACAAAGTTTAACCCTAGTAGATTCGATGACGAAGCTAAACCTTACTCATTTTTGGC
ATTCGGTATGGGTGGTAGACAATGTTTGGGTATGAACATGGCAAAGGCCATGATGTTGGTTTTCT
TGCACAGATTGGTCACCTCATTCAGATGGAAGGTTATAGATTCCGACTCTTCAATCGAAAAATGG
GCTTTGTTCTCTAAGTTGAAGTCAGGTTGCCCTATCGTAGTTACCCACATCGGTTCCTAA

CYP4149 (SEQ ID NO:12)
ATGGATTTCTACTGGATCTGTGTTCTTCTGCTTTGCTTCGCATGGTTTTCCATTTTATCCCTTCA
CTCGAGAACAAACAGCAGCGGCACTTCCAAACTTCCTCCCGGACCGAAACCCTTGCCGATCATCG
GAAGCCTTTTGGCTCTCGGCCACGAGCCCCACAAGTCTTTGGCTAATCTCGCTAAATCTCATGGC
CCTCTTATGACCCTAAAGCTCGGCCAAATCACCACCGTCGTAGTTTCCTCCGCTGCCATGGCTAA
GCAAGTTCTCCAAACGCACGACCAGTTTCTGTCCAGCAGGACCGTTCCAGACGCAATGACCTCTC
ACAACCACGATGCTTTCGCACTCCATGGATTCCGGTTTCACCCCTCTGGCGAAACGTTCGACGA
ATATGCAACAACCAGTTGTTTGCCGGCAAGATTCTCGACGGCAACGAGAATCTCCGGCGAACCAA
AGTGGCCGAGCTCGTATCCGATATCTCGAGAAGTGCATTGAAGGTGAGATGGTGGATTTTGGAA
ACGTGGTGTTCGTCACTTCGCTCAATCTGCTTTCCAATACGATTTTCTCGGTGGATTTCTTCGAC
CCAAATTCTGAAATTGGGAAAGAGTTCAGGCACGCAGTACGAGGCCTCATGGAAGAAGCTGCCAA
ACCAAATTTGGGGGATTATTTCCCTCTGCTGAAGAAGATAGATCTTCAAGGAATAAAGAGGAGAC
AGACCACTTACTTCGATCGGGTTTTTAATGTTTTGGAGCACATGATCGACCAGCGTCTTCAGCAG
CAGAAGACGACGTCTGGTTCTACCTCCAACAACAACAACGACTTACTGCACTACCTTCTCAACCT
CAGCAACGAAAATAGCGACATGAAATTGGGGAAACTTGAGCTGAAACACTTCTTATTGGTGCTAT
TCGTCGCTGGGACTGAAACGAGTTCTGCAACACTGCAATGGGCAATGGCAGAACTACTAAGAAAC
CCAGAAAAGTTAGCAAAAGCTCAAGCGGAGACCAGGCGGGTGATTGGGAAAGGGAACCCAATTGA
AGAATCAGACATTTCGAGGCTGCCTTATCTGCAAGCAGTGGTGAAAGAAACTTTCAGATTGCACA
CACCAGCGCCATTTCTACTGCCGCGCAAAGCACTACAGGACGTGGAAATTGCAGGTTTCACAGTC
CCAAGGACGCTCAGGTACTGGTAAATTTATGGCTATGAGCAGAGATTCAAGCATCTGGAGAA
CCCAGAGTGGTTCGAGCCAGAAAGGTTTTTGGAGTCGGAGCTGGACGTTAGAGGGAGAGATTTTG
AGCTGATCCCGTTCGGCGGTGGCGGAGGATTTGCCCCGGTCTGCCGTTGGCGATGAGAATGTTG
CATTTGATTTTGGGTTCTCTCATCCACTTCTTTGATTGGAAGCTGAAGATGGGTGTCGGCCGGA

FIG.15 (CONT.)

AGACGTGAAAATGGACGAAAAGCTTGGCCTCACTCTGGAGTTGGCTTTTCCCCTCACAGCCTTGC
CTGTCCTTGTCTAA

CYP4491 (SEQ ID NO:13)
ATGTCCTCCTGCGGTGGTCCAACTCCTTTGAATGTTATCGGTATCTTATTACAATCAGAATCCTC
CAGAGCCTGCAACTCAGACGAAAACTCAAGAATTTTGAGAGATTCGTAACAAGAGAAGTTAACG
CTTTCTTATGGTTGTCCTTGATCACTATCACAGCAGTTTTGATCAGTAAAGTTGTCGGTTTGTTT
AGATTGTGGTCTAAGGCAAAGCAATTGAGAGGTCCACCTTGTCCATCATTCTACGGTCATTCTAA
GATCATCTCAAGACAAAATTTGACTGATTTGTTATATGACTCCCACAAAAGTACGGTCCAGTAG
TTAAATTGTGGTTAGGTCCTATGCAATTGTTAGTCTCCGTAAAGGAACCAAGTTTGTTGAAGGAA
ATATTGGTTAAAGCTGAGGATAAGTTGCCTTTAACAGGTAGAGCCTTTAGATTGGCTTTCGGTAG
ATCTTCATTATTGCATCCAGTTTCGAAAAGGTTCAAAACAGAAGACAAAGATTGGCCGAAAAGT
TGAATAAGATCGCATTCCAAAGAGCCAACATCATTCCAGAAAAGGCCGTAGCTTGTTTCATGGGT
AGAGTTCAAGATTTGATGATAGAAGAATCTGTCGACTGTAATAAGGTTTCTCAACATTTGGCTTT
TACTTTGTTAGGTTGCACATTGTTTGGTGACGCCTTCTTAGGTTGGTCTAAGGCTACAATCTATG
AAGAATTGTTGATGATGATCGCTAAGGACGCATCCTTTTGGGCTAGTTATAGAGTTACCCCAATC
TGGAAGCAAGGTTTCTGGAGATACCAAAGATTGTGTATGAAGTTGAAGTGCTTGACTCAAGATAT
CGTTCAACAATACAGAAAGCATTACAAGTTGTTTCTCACTCACAAAACCAAAACTTACACAACG
AAACCAAGTCAACTGGTGTTGAAGTCGCTTTTGATATTCCACCTTGTCCTGCTGCAGACGTTAGA
AATTCTTGCTTTTTCTACGGTTTGAACGATCATGTTAACCCCAAACGAAGAACCTTGTGGTAATAT
TATGGGTGTCATGTTTCACGGTTGCTTGACTACAACCTCTTTGATCGCATCAATCTTGGAAAGAT
TGGCCACTAACCCAGAAATCCAAGAAAAGATTAATTCTGAATTGAACTTAGTTCAAAAGGGTCCA
GTCAAGGATCATAGAAAGAATGTTGACAACATGCCTTTGTTATTGGCAACAATCTATGAATCAGC
TAGATTATTGCCAGCAGGTCCTTTATTGCAAAGATGTCCTTTGAAGCAAGATTTGGTTTTGAAAA
CAGGTATCACCATTCCAGCTGGTACCTTGGTCGTAGTTCCTATTAAATTGGTTCAAATGGATGAC
TCTTCATGGGGTTCAGATGCCAATGAGTTTAATCCATACAGATTCTTGTCCATGGCTTGTAATGG
TATTGACATGATACAAAGAACCCCTTTAGCTGGTGAAAACATTGGTGACCAAGGTGAACGTTCAT
TTGTCTTGAATGACCCAATTGGTAACGTAGGTTTCTTACCTTTTGGTTTCGGTGCAAGAGCCTGC
GTTGGTCAAAAGTTTATAATCCAAGGTGTCGCTACTTTGTTCGCAAGTTTGTTGGCCCATTACGA
AATTAAATTGCAATCCGAGAGTAAGATGATTCTAAACCATCCAGTAACACCTCTGCCAGTCAAA
TCGTCCCAAACTCAAAAATCGTATTCGTAAGAAGAAACTCATAA

CYP5491 (SEQ ID NO:14)
ATGTGGACTGTCGTGCTCGGTTTGGCGACGCTGTTTGTCGCCTACTACATCCATTGGATTAACAA
ATGGAGAGATTCCAAGTTCAACGGAGTTCTGCCGCCGGGCACCATGGGTTTGCCGGCTCATCGGAG
AGACGATTCAACTGAGTCGACCCAGTGACTCCCTCGACGTTCACCCTTTCATCCAGAAAAAGTT
GAAAGATACGGGCCGATCTTCAAAACATGTCTGGCCGGAAGGCCGGTGGTGGTGTCGGCGGACGC
AGAGTTCAACAACTACATAATGCTGCAGGAAGGAAGAGCAGTGGAAATGTGGTATTTGGATACGC
TCTCCAAATTTTTCGGCCTCGACACCGAGTGGCTCAAAGCTCTGGGCCTCATCCACAAGTACATC
AGAAGCATTACTCTCAATCACTTCGGCGCCGAGGCCCTGCGGGAGAGATTTCTTCCTTTTATTGA
AGCATCCTCCATGGAAGCCCTTCACTCCTGGTCTACTCAACCTAGCGTCGAAGTCAAAAATGCCT
CCGCTCTCATGGTTTTTAGGACCTCGGTGAATAAGATGTTCGGTGAGGATGCGAAGAAGCTATCG
GGAAATATCCCTGGGAAGTTCACGAAGCTTCTAGGAGGATTTCTCAGTTTACCACTGAATTTTCC
CGGCACCACCTACCACAAATGCTTGAAGGATATGAAGGAAATCCAGAAGAAGCTAAGAGAGGTTG
TAGACGATAGATTGGCTAATGTGGGCCCTGATGTGGAAGATTCTTGGGGCAAGCCCTTAAAGAT
AAGGAATCAGAGAAGTTCATTTCAGAGGAGTTCATCATCCAACTGTTGTTTTCTATCAGTTTTGC
TAGCTTTGAGTCCATCTCCACCACTCTTACTTTGATTCTCAAGCTCCTTGATGAACACCCAGAAG
TAGTGAAAGAGTTGGAAGCTGAACACGAGGCGATTCGAAAAGCTAGAGCAGATCCAGATGGACCA
ATTACTTGGGAAGAATACAAATCCATGACTTTTACATTACAAGTCATCAATGAAACCCTAAGGTT
GGGGAGTGTCACACCTGCCTTGTTGAGGAAAACAGTTAAAGATCTTCAAGTAAAAGGATACATAA
TCCCGGAAGGATGGACAATAATGCTTGTCACCGCTTCACGTCACAGAGACCCAAAAGTCTATAAG
GACCCTCATATCTTCAATCCATGGCGTTGGAAGGACTTGGACTCAATTACCATCCAAAAGAACTT

FIG.15 (CONT.)

CATGCCTTTTGGGGGAGGCTTAAGGCATTGTGCTGGTGCTGAGTACTCTAAAGTCTACTTGTGCA
CCTTCTTGCACATCCTCTGTACCAAATACCGATGGACCAAACTTGGGGGAGGAAGGATTGCAAGA
GCTCATATATTGAGTTTTGAAGATGGGTTACATGTGAAGTTCACACCCAAGGAATGA

CYP6479 (SEQ ID NO:15)
ATGAAGATGAAGATGGAATCCATGCGCACCTCCCTGGATATCTCCGACCATGACATACTTCCAAG
GGTTTATCCTCATGTTCACCTATGGATCAACAAATATGGGAAAAACTTCATTCAGTGGAATGGCA
ACGTAGCTCAGTTGATTGTTTCGGATCCTGACACGATCAAGGAGATACTCCAAAACCGAGAACAA
GCTGTTCCCAAAATAGATCTCAGCCGGAGATGCACGGAGGATATTCGGGAATGGGCTTTCGACTTC
TGACGGTGAAAAATGGGCTAAGGCTCGAAGAATCGCTGATTACGCTTTCCACGGGGATCTCCTAA
GAAATATGGGGCCAACCATGGTTTCCTGTGCTGAGGCAATGGTGGAAAAGTGGAAGCATCATCAA
GGCAAAGAGCTTGATTTGTTCGAAGAGTTTAAGGTGCTCACTTCAGATATCATTGCACATACAGC
CTTTGGAAGCAGTTATTTGGAAGGGAAAGTTATTTTTCAGACTCTAAGTAAGCTGAGCATGATAT
TATTTAAGAATCAGTTCAAACGAAGGATTCCTGTTATCAGCAAGTTCTTCAGATCAAAGGATGCG
AGGGAGGGAGAGGAGCTGGAAAGAAGGTTGAAAAAATTCCATAATTTCAATAATGGAAAAGAGAGA
AGAGAAGGTGATAAGTGGTGAAGCAGATAACTATGGTAATGATTTTCTTGGATTACTTTTGAAGG
CAAAGAATGAGCCTGACCAGAGGCAGAGGATTTCTGTTGATGATGTAGTGGATGAATGCAAAACA
GTTACTTCGCTGGGCAAGAAACTACAAGTGTTTGCTTGCTTGGACCGCCTTTCTTTTAGCAAC
TCATGAGCATTGGCAAGAAGAAGCAAGAAAGGAAGTGCTGAATATGTTTGGCAACAAGAATCCAA
CTTTAGAAGGCATCACAAAATTAAAGATTATGAGCATGATCATCAAGGAATCTCTAAGATTATAT
CCTCCAGCCCCGCCCATGTCAAGGAAGGTTAAAAAGGAAGTCAGATTGGGGAAGCTGGTTCTCCC
CCCCAACATTCAAGTAAGCATCTCAACTATTGCAGTTCATCATGATACTGCAATATGGGGTGAAG
ATGCCATGTATTCAAACCAGAAAGATTTTCTGAAGGAACAGCTAAAGATATCCCATCAGCTGCA
TACATCCATTTGGCTTTGGTCCTCGAAACTGCATCGGCAATATCTTGGCCATCAACGAAACTAA
GATTGCACTGTCGATGATTCTACAACGATTTTCTTTCACCATCTCCCCGGCCTACGTCCACGCAC
CTTTCCAGTTCCTCACTATCTGCCCCCAACACGGGGTTCAGGTAAAGCTTCAGTCCCTATTAAGT
GAAAGGTGA

CYP7604 (SEQ ID NO:16)
ATGGAAGCTGAATTTGGTGCCGGTGCTACTATGGTATTATCCGTTGTCGCAATCGTCTTCTTTTT
CACATTTTTACACTTGTTTGAATCTTTCTTTTTGAAGCCAGATAGATTGAGATCTAAGTTGAGAA
AGCAAGGTATTGGTGGTCCATCTCCTTCATTTTTGTGGGTAATTTGTCAGAAATTAAATCCATC
AGAGCTTTGTCTTCACAAGCTAAGAACGCAGAAGATGCCTCTGCTGGTGGTGGTGGTGGTTCCGC
CAGTATAGCTCATCGTTGGACTTCAAATTTGTTTCCTCACTTAGAACAATGGAGAAACAGATATG
GTCCAATTTTCGTATACTCCAGTGGTACAATCCAAATCTTGTGTATCACAGAAATGGAAACCGTT
AAGGAAATCTCTTTGTCAACCTCCTTGAGTTTAGGTAAACCTGCTCATTTGTCTAAGATAGAGG
TCCATTGTAGGTTTGGGTATCTTAGCCTCTTCAGGTCCTATTTGGGTTCACCAAAGAAAGATCA
TCGCTCCACAATTGTATTTGGATAAAGTAAAGGGTATGACCTCATTGATGGTTGAAAGTGCAAAT
TCTATGTTAAGATCCTGGGAAACTAAAGTTGAAAATCATGGTGGTCAAGCCGAAATTAACGTCGA
TGGTGACTTGAGAGCATTAAGTGCCGATATCATTTCTAAGGCTTGCTTTGGTTCAAACTATTCCG
AAGGTGAAGAAATTTTCTTGAAGTTGAGAGCATTGCAAGTTGTCATGAGTAAGGGTTCTATTGGT
ATACCTGGTTTTAGATACATACCAACTAAAAATAACAGAGAAATGTGGAAGTTGGAAAAGGAAAT
CGAATCAATGATCTTGAAGGTTGCCAACGAAAGAACACAACATTCCAGTCACGAACAAGATTTGT
TGCAAATGATTTTGGAAGGTGCAAAGTCTTTGGGTGAAGACAATAAGAGTATGAACATATCAAGA
GACAAGTTTATTGTTGACAATTGTAAGAACATCTATTTCGCTGGTCATGAAACTACAGCTATAAC
CGGCATCTTGGTGCTTGATGTTGTTAGCTGCACACCCTGATTGGCAAGCAAGAGCCAGATCTGAAG
TTTTACAATGTTGCCGATGACAGACCAATCGATGCAGACACAGTCAAAAATATGAAGACCTTGACT
ATGGTAATTCAAGAAACTTTGAGATTGTACCCACCTGCTGTATTCGTTACAAGACAAGCATTAGA
AGATATCAGATTCAAAAACATCACAATACCAAAGGGTATGAACTTTCATATACCAATCCCTATGT
TGCAACAAGACTTCCACTTATGGGGTCCTGATGCTTGTTCATTTGACCCACAAAGATTCTCCAAT
GGTGTCTTAGGTGCATGCAAAAACCCACAAGCCTATATGCCTTTTGGTGTTGGTCCAAGAGTCTG
TGCCGGTCAACATTTCGCTATGATCGAATTGAAAGTCATCGTATCATTGGTTTTGTCCAGATTCG

AATTTTCTTTGTCACCTTCCTACAAGCATTCACCAGCCTTCAGATTAGTTGTCGAACCAGAAAAC
GGTGTCATATTGCATGTCAGAAAGTTGTGA

CYP8224 (SEQ ID NO:17)
ATGGAAGTGGATATCAATATCTTCACCGTCTTTTCCTTCGTATTATGCACAGTCTTCCTCTTCTT
TCTATCCTTCTTGATCCTCCTCCTCCTCCGAACGCTCGCCGGAAAATCCATAACGAGCTCCGAGT
ACACGCCAGTGTACGGCACCGTCTACGGTCAGGCTTTCTATTTCAACAACCTGTACGATCATCTA
ACGGAGGTGGCCAAGAGACATCGAACCTTCCGGCTGCTTGCGCCGGCATACAGCGAGATATACAC
GACCGATCCGAGAAACATCGAGCATATGTTGAAGACGAAATTCGATAAGTATTCGAAAGGAAGCA
AGGATCAAGAAATCGTTGGGGATCTGTTTGGAGAGGGGATATTTGCAGTCGATGGAGATAAGTGG
AAGCAGCAGAGGAAGCTGGCTAGCTATGAATTCTCGACGAGGATTCTTAGGGATTTTAGCTGCTC
GGTTTTCAGACGAAGTGCTGCTAAACTTGTTGGAGTTGTTTCGGAGTTTTCCAGCATGGGTCGGG
TTTTTGATATCCAGGATTTGCTAATGCGGTGCGCTTTGGACTCCATTTTCAAAGTGGGGTTCCGG
GTTGATTTGAATTGCTTGGAGGAATCAAGCAAAGAAGGGAGCGATTTCATGAAAGCCTTCGATGA
TTCTAGCGCTCAGATTTTTTGGCGCTATATCGATCCCTTCTGGAAATTGAAGAGATTGCTTAAACA
TCGGTTCCGAAGCTTCGTTAGGAACAACATAAAAACCATAGATGCTTTTGTGCACCAGTTGATC
AGAGACAAGAGAAAATTGCTTCAGCAACCGAATCACAAGAATGACAAAGAGGACATACTTTGGAG
GTTCTGATGGAAAGTGAGAAGGATCCAACAAGAATGAATGATCAATATCTAAGGGATATAGTCC
TCAATTCATGTTGGCTGGCAAAGATTCAAGTGGAGGAACTCTGTCCTGGTTCTTCTACATGCTA
TGCAAGAACCCTTTAATACAGGAAAAAGTTGCAGAAGAAGTGAGGCAAATTGTTGCGTTTGAAGG
GGAAGAAGTTGACATCAATTTGTTCATACAAAACTTAACTGATTCAGCTCTTGACAAAATGCATT
ATCTTCATGCAGCATTGACCGAGACTCTGAGGCTATATCCTGCAGTCCCTTTGGATGGAAGGACT
GCAGAAATAGATGACATTCTTCCTGATGGCTATAAACTAAGAAAAGGGGATGGAGTATACTACAT
GGCCTATTCCATGGGCAGGATGTCCTCCCTTTGGGGAGAAGATGCTGAAGATTTTAAACCCGAAA
GATGGCTTGAAAGTGGAACTTTTCAACCCGAATCACCTTTCAAATTCATCGCTTTTCATGCGGGT
CCTCGAATGTGTTTGGGAAAAGAGTTTGCTTATCGACAAATGAAGATAGTATCTGCTGCTTTGCT
TCAATTTTTTCGATTCAAAGTAGCTGATACAACGAGGAATGTGACTTATAGGATCATGCTTACCC
TTCACATTGATGGAGGTCTGCCTCTTCTTGCAATTCCGAGAATTAGAAAATTTACCTAA

CYP8728 (SEQ ID NO:18)
TTGGATAGTGGAGTTAAAAGAGTGAAACGGCTAGTTGAAGAGAAACGGCGAGCAGAATTGTCTGC
CCGGATTGCCTCTGGAGAATTCACAGTCGAAAAGCTGGTTTTCCATCTGTATTGAGGAGTGGCT
TATCAAAGATGGGTGTTCCCAGTGAGATTCTGGACATATTATTTGGTTTCGTTGATGCTCAAGAA
GAATATCCCAAGATTCCCGAAGCAAAAGGATCAGTAAATGCAATTCGTAGTGAGGCCTTCTTCAT
ACCTCTCTATGAGCTTTATCTCACATATGGTGGAATATTTAGTTGACTTTTGGGCCAAAGTCAT
TCTTGATAGTTTCTGATCCTTCCATTGCTAAACATATACTGAAGGATAATCCGAGGAATTATTCT
AAGGGTATCTTAGCTGAAATTCTAGAGTTTGTCATGGGGAAGGGACTTATACCAGCTGACGAGAA
GATATGGCGTGTACGAAGGCGGGCTATAGTCCCATCTTTGCATCTGAAGTATGTAGGTGCTATGA
TTAATCTTTTTGGAGAAGCTGCAGATAGGCTTTGCAAGAAGCTAGATGCTGCAGCATCTGATGGG
GTTGATGTGGAAATGGAGTCCCTGTTCTGCCGTTTGACTTTAGATATCATTGGCAAGGCAGTTTT
TAACTATGACTTTGATTCACTTACAAATGACACTGGCATAGTTGAGGCTGTTTACACTGTGCTAA
GAGAAGCAGAGGATCGCAGTGTTGCACCAATTCCAGTATGGGAAATTCCAATTTGGAAGGATATT
TCACCACGGCAAAAAAAGGTCTCTAAAGCCCTCAAATTGATCAACGACACCCTCGATCAACTAAT
TGCTATATGCAAGAGGATGGTTGATGAGGAGGAGCTGCAGTTTCATGAGGAATACATGAATGAGC
AAGATCCAAGCATCCTTCATTTCCTTTTGGCATCAGGAGATGATGTTTCAAGCAAGCAGCTTCGT
GATGACTTGATGACTATGCTTATAGCTGGGCATGAAACATCTGCTGCAGTTTTAACATGGACCTT
TTATCTTCTTTCCAAGGAGCCGAGGATCATGTCCAAGCTCCAGGAGGAGGTTGATTCAGTCCTTG
GGGATCGGTTTCCAACTATTGAAGATATGAAGAACCTCAAATATGCCACACGAATAATTAACGAA
TCCTTGAGGCTTTACCCACAGCCACCAGTTTTAATACGTCGATCTCTTGACAATGATATGCTCGG
GAAGTACCCCATTAAAAAGGGTGAGGACATATTCATTTCTGTTTGGAACTTGCATCGCAGTCCAA
AACTCTGGGATGATGCGGATAAATTTAATCCTGAAAGGTGCCTTCTGGATGGACCCAATCCAAAT
GAGACAAATCAAAATTTCAGATATTTACCTTTTGGTGGCGGACCACGGAAATGTGTGGGAGACAT

FIG.15 (CONT.)

GTTTGCTTCGTACGAGACTGTTGTAGCACTTGCAATGCTTGTTCGGCGATTTGACTTCCAAATGG
CACTTGGAGCACCTCCTGTAAAAATGACAACTGGAGCTACAATTCACACAACAGATGGATTGAAA
ATGACAGTTACACGAAGAATGAGACCTCCAATCATACCACATTAGAGATGCCTGCAGTGGTCGT
TGACTCGTCTGTCGTGGACTCGTCCGTCGCCATTTTGAAAGAAGAAACACAAATTGGTTAG

CYP10820 (SEQ ID NO:19)
CAGTTCCTCTCCTGGTCCTCCCAGTTTGGCAAGAGGTTCATCTTCTGGAATGGGATCGAGCCCAG
AATGTGCCTCACCGAGACCGATTTGATCAAAGAGCTTCTCTCTAAGTACAGCGCCGTCTCCGGTA
AGTCATGGCTTCAGCAACAGGGCTCCAAGCACTTCATCGGCCGCGGTCTCTTAATGGCCAACGGC
CAAAACTGGTACCACCAGCGTCACATCGTCGCGCCGGCCTTCATGGGAGACAGACTCAAGAGTTA
CGCCGGGTACATGGTGGAATGCACAAAGGAGATGCTTCAGTCAATTGAAAACGAGGTCAACTCGG
GGCGATCCGAGTTCGAAATCGGTGAGTATATGACCAGACTCACCGCCGATATAATATCACGAACC
GAGTTCGAAAGCAGCTACGAAAAGGGAAAGCAAATTTTCCATTGCTCACCGTTTTACAGCATCT
CTGCGCTCAGGCGAGCCGCCACCTCTGCCTTCCTGGAAGCCGGTTTTTTCCGAGTAAATACAACA
GAGAGATAAAGGCATTGAAGACGAAGGTGGAGGGGTTGTTAATGGAGATAATACAGAGCAGAAGA
GACTGTGTGGAGGTGGGGAGGAGCAGTTCGTATGGAAATGATCTGTTGGGAATGTTGCTGAATGA
GATGCAGAAGAAGAAAGATGGGAATGGGTTGAGCTTGAATTTGCAGATTATAATGGATGAATGCA
AGACCTTCTTCTTCGCCGGCCATGAAACCACTGGTCTTTTGCTCACTTGGACTGTAATGTTATTG
GCCAGCAACCTTCTTGGCAACACAAGGTTCGAGCCGAAGTTATGGCCGTCTGCAATGGAGGAAC
TCTCTCTCTTGAACATCTCTCCAAGCTCTCTCTGTTGAGTATGGTGATAAATGAATCGTTGACGC
TATACCCGCCAGCAAGTATTCTTCCAAGAATGGCATTTGAAGATATAAAGCTGGGAGATCTTGAG
ATCCCAAAAGGGCTGTCGATATGGATCCCAGTGCTTGCAATTCACCACAGTGAAGAGCTATGCGG
CAAAGATGCAAATGAGTTCAACCCAGAAAGATTTGCAAATTCAAAAGCCTTCACTTCGGGGAGAT
TCATTCCCTTTGCTTCTGGCCCTCGCAACTGCGTTGGCCAATCATTTGCTCTCATGGAAACCAAG
ATCATTTTGGCTATGCTCATCTCCAAGTTTTCCTTCACCATCTCTGACAATTATCGCCATGCACC
CGTGGTCGTCCTCACTATAAAACCCAAATACGGAGTCCAAGTTTGCTTGAAGCCTTTCAATTAA

CYP10285 (SEQ ID NO:20)
ATGGAAGACACCTTCCTACTCTATCCTTCCCTCTCTCTTCTCTTTCTTCTTTTTGCTTTCAAGCT
CATCCGTCGATCCGGAGGAGTTCGCAGGAACTTACCGCCGAGTCCGCCCTCTCTTCCGGTTATCG
GCCACCTCCATCTCTTGAAAAAGCCACTCCACCGGACTTTCCAGAAACTTTCCGCCAAATATGGT
CCTGTTATGTCCCTCCGCCTCGGGTCTGGCCTCGCAGTCATTGTATCGTCGTCGTCGGCGGTGGA
CGAGTGTTTCACTAAAAACGACGTCGTGCTCGCCAACCGTCCTCGTTTGCTAATTGGCAAACACC
TCGGCTACAACTACACTACCATGGTTGGGGCTCCCTACGGCGACCACTGGCGTAGCCTCCGCCGC
ATCGGTGCCCTCGAAATCTTCTCTTCATCTCGCCTCAACAAATTCGCCGACATCCGAAGGGATGA
AGTAGAGGGATTGCTTCGCAAACTCTCACGCAATTCGCTCCATCAATTCTCGAAAGTGGAAGTTC
AATCGGCCTTGTCGGAGCTGACGTTCAACATCTCGATGAGAATGGCGGCAGGGAAACGGTATTAC
GGAGATGACGTGACGGACGAGGAAGAGGCGAGAAAGTTCAGAGAGTTAATTAAACAGATAGTGGC
GCTGGGCGGAGTATCAAATCCAGGGGATTTCGTCCCGATTCTGAATTGGATTCCGAACGGTTTCG
AGAGGAAGTTGATCGAGTGTGGGAAGAAGACGGATCGTTCTTGCAGGGCTGATCGAGGACCAC
CGGAGAAGAAGGAAGAGGGTAGGAACACGATGATCGATCACCTGCTCTCTCTGCAAGAATCCGA
GCCTGCTCACTACGGAGACCAAATAATCAAAGGATTTATACTGGTGTTACTGACGGCGGGGACCG
ATACATCGGCCGTGACAATGGAGTGGGCGCTATCTCATCTCCTGAACAATCCTGAAGTGCTAAAG
AAGGCAAGAGATGAGGTCGACACTGAAATTGGACAAGAACGACTTGTCGAAGAATCAGACGTAGT
ATCTAAGTTACCCTATCTTCAAGGGATCATCTCCGAGACTCTCCGGCTGAATCCGCCGCTCCGA
TGTTGTTGCCCCATTACGCCTCGGACGACTGCACGATATGTGGATACGACGTGCCACGTGACACA
ATCGTAATGGTCAATGCATGGGCCATACATAGGGATCCAAACGAATGGGAGGAGCCCACGTGTTT
CAGACCAGAACGATATGAAAAGTCGTCGTCGGAAGCGGAGGTACACAAGTCGGTGAGTTTCGGGG
TGGGAAGGCGAGCTTGTCCTGGGTCTGGCATGGCGCAGACGGTGATGGGCTTGACTTTGGCGGCA
CTGGTTCAGTGCTTCGAGTGGGAGAGAGTTGGAGAAGAAGAAGTGGACATGAACGAAGGCTCAGG
TGCCACAATGCCCAAGATGGTGCCATTGGAGGCCATGTGCAGAGCTCGTCCCATCGTCCACAACC
TTCTTTACTGA

CYP10969 (SEQ ID NO:41)
GTGGGCCGTCGTCTGTTGAAGCTCCTCAGCGGACGATTTCGAAGCCTGAACAGAGGGAGCTACC
GTTGAGGAAGATTCCCGGGGACTATGGGCCGCCGTTGTTGGGTCCGATTAAGGACCGACAAGACT
ATTTTTACAATCAGGGGAGGGAGGAGTTCCTGAGATCACGCATGAACAGGTACGAATCAACTGTG
TACAGAACTAATATGCCACCAGGTCCCTTTATCTCCTCCGATTCTCGTGTCATCGTTTTACTCGA
CGGCAAGAGCTTCCCTGTACTCTTCGACGTTTCTAAAGTTCTGAAACAAGACGTCTTCACCGAA
CTTATATGCCCTTAACGGAGCTCACTGGCGGCTACCGAGTTCTTCTTATCTCGACCCCTCCGAG
CCCGATCACGAGAAGCTTAAACAGTTCCTCTTCTACCTCCTCAAGTACCGTCGCGACAAGATTCT
GCCGGAGTTTCACTCTACCTTTTCGGAGCTGTTTGAGACTCTGGAGAAGGAGGTGGCTGCCGCCG
GTAGAGCAGATTATAATGATCCCGGTGAACAGGCGGCGTTTAACTTCTTGGCTCGGTCTCTGTTC
GGCGCCAACCCGCCCGACACCAAACTGGGAAACGACGCTCCGAGTTTAATATCCAAATGGGTGCT
GTTCCAGCTGGGTCCGGTTCTCACTCTTGGTCTTCCCAAGCCTGTCGAGGAGCTTCTCCTGCGAA
CCGTCCGGCTGCCACCGGCGCTTGTGAAATCGGATTACCAGCGGCTGTACGATTTCTTTTACGAG
GCGTCGGAGGCTGTGTTTGCGGAGGCGGATAGATTGGGCATTGCGAGAGAGGAAGCGTGTCACAA
CTTGGTCTTCGCCACGTGCTTCAATTCCTTCGGAGGGATGAAGATCCTCTTCCCCAATATGATAA
AATGGATCGGACGTGCCGGAGTGAATCTCCATACGGAGCTCGGACGGGAGATAAGATCCGCCGTC
AAAGCCCACGGCGGCAAGATCACGATGGCGGCTATGGAACAGATGCCGCTGATGAAGTCCGTAGT
GTACGAAACGCTCAGAATCGAACCCCCGGTTCCTGCGCAATACGGGCGAGCGAAGGAGGACCTGG
TGATCGAGAGCCACGACGCCGCTTTCGAGATCAAAGAAGGGGAAATGTTGTGTGGGTAGCAGCCA
TTCGCCACTAGAGATCCGAAAATATTCGAGAGATCCGAAGAATTCGTACCGGATCGGTTCACCGG
CGACGGCGAGGAGTTGCTGAAGCACGTGCTCTGGTCAAACGGACCGGAGACTCAATCCCCAACCG
TTAAGACAAGCAGTGCGCTGGCAAAGACTTCATAGTCTTCGTCTCCCGCCTCCTCGTCGTCGAA
CTCTTCCTCCGATACGACTCCTTCGACATTGAAGTCGCAGCTTCGCCGTTGGCGCCGCCGTCAC
CATAGCTTCCCTGAAGAAGGCAAGCTTTTAA

FIG.15 (CONT.)

UGT73C3 (SEQ ID NO:21)

MATEKTHQHPSLHFVLFPFMAQGHMIPMEDIARLLAQRGVTITIVTTPHNAARFKNVLNRAIESGLAINILIVKFPYQEFGLP
EGKEMIDSLDSTELMVPFFKAVNLLEDPVMKLMEEMKPRPSCLISDWCLPYTSHAKFNIPKLVFHGMGCFNLLQMHVLRRN
LHILENVKSDEEYFLVPSFFDRVEFTKLQLPVKANASGDWKEIMDEMVKAEYTSYGVIVNTFQELEPPYVKDYKEAMDGKV
WSIGPVSLCNKAGADKAFRGSKAAIDQDECLQWLDSKEEGSVLYVCLGSIONLPSLQLKELGLQLEESRRSFTWVIRGSEKYK
ELFEWMLESGFEERIKERGLLIKGWAPQVLILSHPSVGGFLTHCGWNSTLEGITSGIPLLITWPLFGIDQFCNQKLYVQVLKAGV
SAGVEFEVMKWGEEDKIGVLVDKEGVKKAVEELMGPSDDAKERRRRVKELGELAHKAVEKGGSSHSNTLLLQDIMQLAQF
KN

UGT73C5 (SEQ ID NO:22)

MVSETTKSSPLHFVLFPFMAQGHMIPMVDIARLLAQRGVLJTIVTTPHNAARFKNVLNRAIESGLPINLVQVKFPYLEAGLQEQ
QENIDSLDTMERMIPFFKAVNFLEEPVQKLIEEMNPRPSCLISDFCLPYTSKIACKFNIPKILFHQMGFCLLCMHVLRKNREIL
DNLKSDKELFTVPDFPDRVEFTRTQVPVETYPACDWKDIFDGMVEANETSYGVINSFQELEPAYAKDYKEVRSGKAWTT
GPVSLCNKVQADKAERQNKSDIDQDECLKWLDSKKHGSVLYVCLGSIONLPSLQLKELGLQLEESQRFTWVIRGWEKYKEL
VEWFSESGFEDRIQDRGLLIKGWSPQMLILSHPSVGGFLTHCGWNSTLEGITAGLPLLTWPLFADQFCNEKLVVEVLKAGVR
SGVEQPMKWGEEEKJGVLVDKEGVKKAVEELMGESDDAKERRRAKELGDSAHKAVEEGGSSHSNISFLLQDIMELAEPNN

UGT73C6 (SEQ ID NO:23)

MAFEKNNEPFLHFVLFPFMAQGHMIPMVDIARLLAQRGVLJTIVTTPHNAARFKNVLNRAIESGLPINLVQVKFPYQEAGLQ
EGQENMDLLTIMEQITSFFKAVNLLKEPVQNLIEEMSPRPSCLISDMCLSYTSELAKKFKIPKLFHGMGCFCLLCVNVLRKNR

FIG.16

EILDNLKSDKEYFLVPYFPDRVEFTRPQVPYETYVPAGWKEILEDMVEADKTSYGVYVSFQELEPAYAKDFKEAPSGKAWTI
GPVSLCNKVGVDKAERGNKSDIDQDECLEWLDSKEPGSVLYVCLGSICNLPLSQLLELGLGLEESQRPFTWVIRGWEKYKEL
VEWPSESGFEDRIQDRGLLIKGWSPQMLILSHPSVGGFLTHCGWNSTLEGITAGLPMLTWPLFADQFCNEKLVVQILKVGVS
AEVKVMKWGEEKIGVLVDKEGVKKAVEELMGESDDAKERRRAKELGESAJKAVEEGGSSHSNITFLLQDIMQLAQSN

LIGT73E1 (SEQ ID NO:24)
MSPKMVAPPTNLIFVLFPLMAQGHLVPMVDIARILAQRGATVTITTPYHANRVRPVISRAIATNLKIQLLELQLRSTEAGLPE
GCESFDQLPSFEYWKNISTAIDILQQPAEDLLRELSPPPDCIISDFLFPWTTDVARRLNIPRLVFNGPGCFYLLCHVAITSNLLG
ENEPVSSNTERVVLPGLPDRIEVTKLQIVGSSRPANVDEMGSWLRAVEAEKASFGIVVNTFEELEPEYVEEYKTVXDKKIMWC
IGPVSLCNKTGPDLAERGNKAATEHNCLKWLDERKLGSVLYVCLGSTLARISAAQAELGLQLESINRPFFWCVRNFTDELKT
WFLIXGFEERVRDRGLIVIGWAPQVILLSHPTTGCFLTHCGWNSTIESITAGVPMITWPFFADQFLNEAFTVEVLKIGVRUGVER
ACLFGEHDKVGVLVKKEDVKKAVECLMDEDEDGIDQRRKRVIELAKMAKIAMAEGGSSYENVSSLIRDVTETVRAPH

LIGT85C2 (SEQ ID NO:25)
MDAMATTEKKPHVIFIFFPAQSHIKAMLKLAQLLHHKGLQIFVNTDFIHNQFLESSGPHCLDGAPGFRFETIPDGVSHSPEASI
PIRESLLRSIETNFLDRFEDLVTKLPDPPTCIISDGFLSVFTTDAAKKLGIPVMMYWTLAACGFMGFYHHSLIEKGFAPLXDASY
LINGYLDTVIDWVPGMEGIRLKDFFLDWSTDLNDKVLMFTTEAPQRSHKVSHHHTFDELEPSIKTLSRYNHYTIGPLQL
LLDQIPEEKKQTGTSLHGYSLVKEEPECPQWLQSKEPNSVVYVNFGSTTVMSLEDMTEPGWGLANSMHYFLWIIRSNLVGEE
NAVLPPELHHHKRGFLASWCSQEKVLKHPSVGGFLTICCWGSTIESLSAGVPMICWPYSWDQLTNCRYICKEWEVGLEMG
TKVKRDEVKRLVQELMGEGHKMENKLAKDWKEKARAIA PNGSSSLNDKMVKETVLARN

FIG.16 (CONT.)

UGT98 (SEQ ID NO:26)
ATGGATGCCGAGGAGGTCACAATTCCACATCTACTTCTGCCTTCTCTCAGCCACCACCCACCATTTGATGCTCCCATGGCTCCGGCTACGGCCATCTCTTCCTTCCTCGAGCTGGCAGCTGGCCAAAAGCCTCTC
CAGGAGGAAATTATTCACAATGGAGAGGTAGCCGAGCGCCATTAAACCAAGGCCATTAAACCAAGTTCCTCCTTTCTTATCCTCTGATGATTCCA
TCCAACTTGTGGAACTTCGTCGTCTCCCTTCTCGTCTCGAGTACCTCCTCATCTACAAACACTTTACAAACAACTTGCCCCGCCATCTCCTTATTGACATTCCAACCTTCGGCCTCTCCAC
CAAGCCTTGCGATCCATGGCCCCAACACTTCAGGTCATTTTACAAACACTTCAGTCATTATGACGCTTCACCTACTCACTACCCAGTTCTA
AGTGGCTTCATCCCTAACATTCAGAGATTGTGTTCTTCAGAAGCCATGGAGCATGTACGCGAGAGCCATGCGGATGGGCTCTTACAGGAGAAGGCTCAAAATTGAAGAA
AATTCCCAATCTCAGATGTTGTTCTTCAGATACTTCCTTGGCCGCATTCTTCGCCGAGACGAAATATATCCTCTCTCTT
ACACTTGCGAATTGCTTGGCTTGTTCGGTCCGGTCCTTGGTTCGGACCGATTCAAACGAATACTTCCCGTCAAACGGAAGGCAAGATACCCGTATTCAAGCATCAAAATTGGCTTAGCTCAGC
AGGAACCGTCCTCAACCGTCTTCATCCTGGTCCTCTGTTCCAAGGCACACCAGCAGCAGCGAATACCACGGAGAGCGTGCCGAAGGGCTTCCTGAAGAGGGTTTCTCTGAGAAGAGGAGAG
GTTAATTCATCTGGGTGAAGGTTGGCCTGCGAGGATTGGCTCAAGAGACCTGGAGCATTGGACACGGGAGAGCTTCTGAGTCGACTCGAGAGCTGGCGTCGGCGTCCGGTAA
AGGGCATGATGTTTGGTGTACACCCATAATACCCAAAATTCAAGAAGAAGATGGTCCGAATGATCAGCATCTCAGAAAGTCAAGAGAGTGATCAAAGAAGGAAGGAAAA
GCCAAGAAGCAGCCTTGGACGCGAAATTCAAGGAGAGTTAAGAAGTAAAGGAGTAAGAGATTGATTTCTCTTGGCCTGAAATTTCTCTTTTGGCTAGAACCTCCATGTT
CAATTAA

UGT1495 (SEQ ID NO:27)
ATGGTTCCATGGCTGGCTCCAGGGCTCAGGGGCCATGTCCTCCCCTTTCTTCCTGAGCTGCCGCCCAAGTTGCTGCCGCCAAGTTGCTCGCCGCCTAGAAACTTCCACATATTCTTCCTGCTCCCCACCGGC
CGTAGAAACAGCTCCTTCCACCACCAAAAACTTCCTCGAGAAGCCCTCCCACCACGTGGAGCTCGTGGTGGCTCAACTCAACTACGCCTTCGCGGAGCTCCTC
CGCACCGGCCACACCACCGGCGACTTCCACGTCGACACGACGCCACCTCAACACCACCTCCTCCCTCTCGCTCAACCGACTCGACACCCAAGCATGCGCGGTTCCTACATGCTCCGC
CACCCGCTGAACCCGGACTTGCTCATCTACGACGGAGCCCTGCTCTCGAAGCTCATCAGCGATGCGCTCCAAGTTCCGGCGATATCCGGCGATGTTCAAAAGCAC
GAGTGCGGCTCATGGCGCCCATGGCGCTGATCCCGAATCTGGTACTCAGCTCTGAATTTTTCCGCGTTTTTCGGGATTATCGTTAAGGATGTTATGAGATCTTGCGGTCGAGTGCGAGA
TTAAACAGCTCGAGAGAACTCGAGAGAAAATGCAGAAATGCGCAGCAGCTCCAGAAGTTCCTTCAAGGATTAAGGATGTGTTATGACAGGATGTATGGACACGACGTTCAACAAAC
GTCGAATCCTTCAGGAGAACGCGTCATCCGGAAGTTGGAAAATCGGAAATAGATATGATCGTCCATACCGTCTCATACTCGTGTCTTCGGGAAGCAGAGTTCTAAGGTGT
CCAAGAGAAGAGACGACCAGTTCCTAGAGCTCGAGCCAGCTAGAGAGAGAGCTGGAGCTCCGTGCAAGTGGTCTCAAGGAGGCCTCAAAGCTTCGA
ACAAGTGGAAGAAGAAGAACTGCCAAGAGGCTTCTAGAGAGAGAGAGGAGAAGCATGAAATTCGGCTCGATCCGATCTTGAA
ACATCCAAGCGTGTGCGTGGCAGCGCCCTCGAATTCCTCAGCCGTGGTCGCAGGGCTCGTGGTGGCGTGGTCGGAGAGGCCGCGGAGAATGCGGAGAGCGCCACGGAGGGCCTCAGATCTTGAA
TCGACCAGCCGCCTCGAATTCCTCAGCCGTGGTCGCAGGGCTCGTGGTGGCGTGGTCGGAGAGGCCGCGGAGAATGCGGAGAGCGCCACGGAGGGCCTCAGATCTTGAA
ACGAGGTGGTGGTGGTGGAGAAGAGTAAGAGAGTGGAGTGGAGGTCATGAGATCATGAGATCATGAGAATCATGAGAGATCATGCAGAGATGAAGAAAGCAATAGAGAGTGGA

UGT1817 (SEQ ID NO:28)

UGT3494 (partial gene sequence) (SEQ ID NO:29)

UGT5914 (SEQ ID NO:30)

```
CTGCTGCCGGATTCCGCTGGCCGGAAACCGGCCGCCGGATCTCCTTGCCGGAAGATCCAGAGGCCGACGGTGGATATTCCGTCCGACAAGAGATTCCGTATCTGAA
ATTGGCCCTGCATCTCGCCGAGCAGCCGGTTCGGAAGTTGTCGTTGAGCGGTCGCGGATTGAATGATCGCTGATTTAATGCTACTGGGTCTGCG
ATATTCTGGAGCTTCCCGAAATCGTTGCCAATCCCAATCGTTTCTTCCGTGTCTTCTTCCGCTGGATTTCTTGCCATGCTGGCTGGACTCCATGCGCGCG
CGTGTCGAGATCGAAGCCTTCTGGTATGAGTGATCGGTGTAAACCAAAAATTCCTCTGCAAGCAAGTCGATGAAGGCCCAGAAAGCCGAGTCGCCGCC
TCGAGAAGAACCGTTGAAATTGTAAACGACCTTGAGTGGCTTGACAAACAAGAGTGATTCCTCCAGATCAGTGTGTTCGGCAGCGAATGCAACTCACGAAAGA
TTGAGTATTGAAATTGTACGACCTTGAGTGGCTTGACAAACAAGAGTGATTCCTCCAGATCAGTGTGTTCGGCAGCGAATGCAACTCACGAAAGA
GATTGGCCATGGAAACGACCTTGAGTGGCTTGACAAACAAGAGTGATTCCCGATCAGTGTGTTCGGCAGCGAATGCAACTCACGAAAGA
TGATGTTTACGACGATAGCGCGGAGTGGAGCTGTCGGAGAAACGACTGTTTGTGGCTCTGGAGCATGGTGAGCATGGGAGATTGAAGCTGATGGC
CTCGCCTGGCATTCCTCCGAGGAGCACCGGCCTCCAGGGTGGACATCCGTGTGAGCATGGGGTGGCATGCCGCCAGATGGGAGATTTAACGCACCCCGTGCGATTGGC
GGCTCTCGTTTCACCGCTGGACAAGGCCGTGTTGCAGTCCGAAGTTGAAGTTCGAAGAAAGGAAGACGGCGTCTTTAGTGAAGAACACATAGCTAAAGCTCAAGAGAAG
TGCAAGGCTTCTCGTTTCACCGCTGGACAAGGCCGTGTTGCAGTCCGAAGTTGAAGTTCGAAGAAAGGAAGACGGCGTCTTTAGTGAAGAACACATAGCTAAAGCTCAAGAGAAG
CTATGGTTTCAGAGACAAGGTTCAGCAAGATGCCGAGGCAAGCGAGAAAG

UGT15423 (partial gene sequence) (SEQ ID NO:36)
ATGGCGCCTCCATCGCGTTTTGCACGTGGTGATTGCATGGCGTGGTATCCCATGCCTAGCCTTGGGTCATCCATTCCATTCCTTCGGCTTGACCTGCTTAGCCACAA
GGCTCTCAGGCACGGGTTGCTTCGTATCAACCACAAGGAACCTGAGCAGAATTCCCAAATACCCTCCAGCAAGCGCTGCGATTCGTCTCCTCGTCGGCTTTC
CTCTGCCCACTGCGACGGCTTCCGACGCGCGCCTCCGACGGCCTCGTAAGACCAATGAAGCAGCAGAAGCAACAAGAACAGCAGTTACTGAAGAAGGCCTTCGACTCTCTG
GAATCAGGCCCGCCGCCATTGCTTCTTGCTTCGTGAATCCGGATTCCGTGATTTGAATCCGGATTATCTACGATTACGGCTTCATTGGCTTCCCGCAGCTCGGCGGAGCTCCG
TAACCTCGTCTGTTTCTGTTGTTGTCTGTTTGCCTTCGTTTTCGTTGGCCCGACCGTTGAGCCGGTTTGACCGGTTCGGGGGACGCGGTCGGGGGACGCGGTCGGGGGACGCGGTCCGGGTGA
```

FIG. 17 (CONT.)

METHODS AND MATERIALS FOR BIOSYNTHESIS OF MOGROSIDE COMPOUNDS

CROSS-REFERENCE TO RELATED APPLICATIONS

This application is divisional of U.S. Ser. No. 13/442,694, filed May 13, 2015, now U.S. Pat. No. 9,932,619, granted Apr. 3, 2018, which is a U.S. national phase of International Application No. PCT/EP2013/075510 filed Dec. 4, 2013, which claims the benefit of U.S. Provisional Application No. 61/733,220 filed Dec. 4, 2012. The entire disclosure contents of these applications are herewith incorporated by reference in their entirety into the present application.

FIELD OF INVENTION

The present invention relates to methods and materials for biosynthesis of mogroside compounds, and more particularly to methods involving use of cytochrome P450 enzymes to produce mogrol and/or using uridine-5'-diphospho (UDP) dependent glucosyltransferases (UGTs) to glycosylate mogrol and produce various mogrol glycosides (mogrosides). The methods may also involve use of enzymes involved in biosynthesis of substrates for mogrol production.

BACKGROUND OF INVENTION

Mogrosides are a family of triterpene glycosides isolated from fruits of *Siraitia grosvenorii* (Swingle), also known as *Momordica grosvenori* (Swingle). Extracts of the fruits are commercially used as natural sweeteners. Four major compounds, Mogroside V, Mogroside IV, Siamenoside I, and 11-Oxomogroside V, have been identified from the fruits of *Siraitia grosvenorii* (Swingle) that are responsible for the sweetness of the fruits (see FIG. 1). Mogroside V is the most abundant of these four compounds at approximately 0.57% (w/w) of the dry fruit, followed by Mogroside IV and Siamenoside I, each of which contain four glucose moieties. 11-Oxomogroside V has a ketone group instead of a hydroxyl at C-11. See, e.g., Takemoto, et al., Yakugaku Zasshi, 103, 1151-1154; 1155-1166; 1167-1173, (1983); Kasai, et al., *Agric. Biol. Chem.* 53, 3347-3349 (1989); Matsumoto, *Chem. Pharm. Bull.* 38, 2030-2032 (1990); and Prakash, et al., *J. Carbohydrate Chem.* 30, 16-26 (2011). However, the enzymes responsible for producing mogrosides have not been identified.

Tang et al. BMC Genomics 2011, 12:343 describes seven CYP450s and five UDPGs as potential candidates involved in mogroside biosynthesis. However, the document does not specifically identify any CYPs or UDPGs involved in mogroside biosynthesis.

SUMMARY OF INVENTION

The present invention provides methods and materials for biosynthesis of mogroside compounds. Interestingly, the invention provides enzymes involved in mogroside biosynthesis.

Mogroside biosynthesis may involve several steps, and accordingly it is an aspect of the present invention to provide enzymes capable of catalysing each of these steps. It is however also foreseen that the methods may involve performing only some of the steps enzymatically, whereas others may be performed by other means.

In one aspect, this document features a method of producing a mogroside compound.

Thus, the invention provides a method of producing a mogroside, wherein the method comprises one or more of the following steps:
Step Ia. Enhancing levels of oxido-squalene
Step Ib. Enhancing levels of dioxido-squalene
Step IIa. Oxido-squalene→cucurbitadienol
Step IIb. Dioxido-squalene→24,25 epoxy cucurbitadienol
Step IIIa. Cucurbitadienol→11-hydroxy-cucurbitadienol
Step IIIb. 24,25 epoxy cucurbitadienol→11-hydroxy-24,25 epoxy cucurbitadienol
Step IVa. 11-hydroxy-cucurbitadienol→mogrol
Step IVb. 11-hydroxy-24,25 epoxy cucurbitadienol→mogrol
Step V mogrol→mogroside Methods for performing each of the above-mentioned steps are described herein below. In particular, enzymes or mixture of enzymes useful for each of above-mentioned steps are described in details herein below.

The invention also features a recombinant host comprising one or more of the following heterologous nucleic acids:
IIa. Heterologous nucleic acid(s) encoding an enzyme or mixture of enzymes capable of catalysing Step IIa (Oxido-squalene→cucurbitadienol)
IIb. Heterologous nucleic acid(s) encoding an enzyme or mixture of enzymes capable of catalysing Step IIb (Dioxido-squalene→24,25 epoxy cucurbitadienol)
IIIa. Heterologous nucleic acid(s) encoding an enzyme or mixture of enzymes capable of catalysing Step IIIa (Cucurbitadienol→11-hydroxy-cucurbitadienol)
IIIb. Heterologous nucleic acid(s) encoding an enzyme or mixture of enzymes capable of catalysing Step IIIb (24,25 epoxy cucurbitadienol→11-hydroxy-24,25 epoxy cucurbitadienol)
IVa. Heterologous nucleic acid(s) encoding an enzyme or mixture of enzymes capable of catalysing Step IVa (11-hydroxy-cucurbitadienol→mogrol)
IVb. Heterologous nucleic acid(s) encoding an enzyme or mixture of enzymes capable of catalysing Step IVb (11-hydroxy-24,25 epoxy cucurbitadienol→mogrol)
V. Heterologous nucleic acid(s) encoding an enzyme or mixture of enzymes capable of catalysing Step V (mogrol→mogroside)

In addition to the heterologous nucleic acids, said recombinant host may have been modified to achieve Step Ia and/or Step Ib.

Unless otherwise defined, all technical and scientific terms used herein have the same meaning as commonly understood by one of ordinary skill in the art to which the invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and are not intended to be limiting. Other features and advantages of the invention will be apparent from the following detailed description. Applicants reserve the right to alternatively claim any disclosed invention using the transitional phrase "comprising," "consisting essentially of," or "consisting of," according to standard practice in patent law.

DESCRIPTION OF DRAWINGS

FIG. 11A shows the LC-MS chromatogram of reference mogroside I A1, while

FIG. 14 shows the amino acid sequence of a cucurbitadienol synthase from *Cucurbita pepo* (SEQ ID NO:1).

FIG. 15 shows the nucleic acid sequences of CYP533, CYP937, CYP1798, CYP1994, CYP2048, CYP2740, CYP3404, CYP3968, CYP4112, CYP4149, CYP4491, CYP5491, CYP6479, CYP7604, CYP8224, CYP8728, CYP10020, CYP10285, and CYP10969 (SEQ ID NOs:3-20 and 41, respectively).

FIG. 16 shows the amino acid sequences of UGT73C3, UGT73C5, UGT73C6, UGT73E1, and UGT85C2 (SEQ ID NOs:21-25, respectively).

Figure 17:
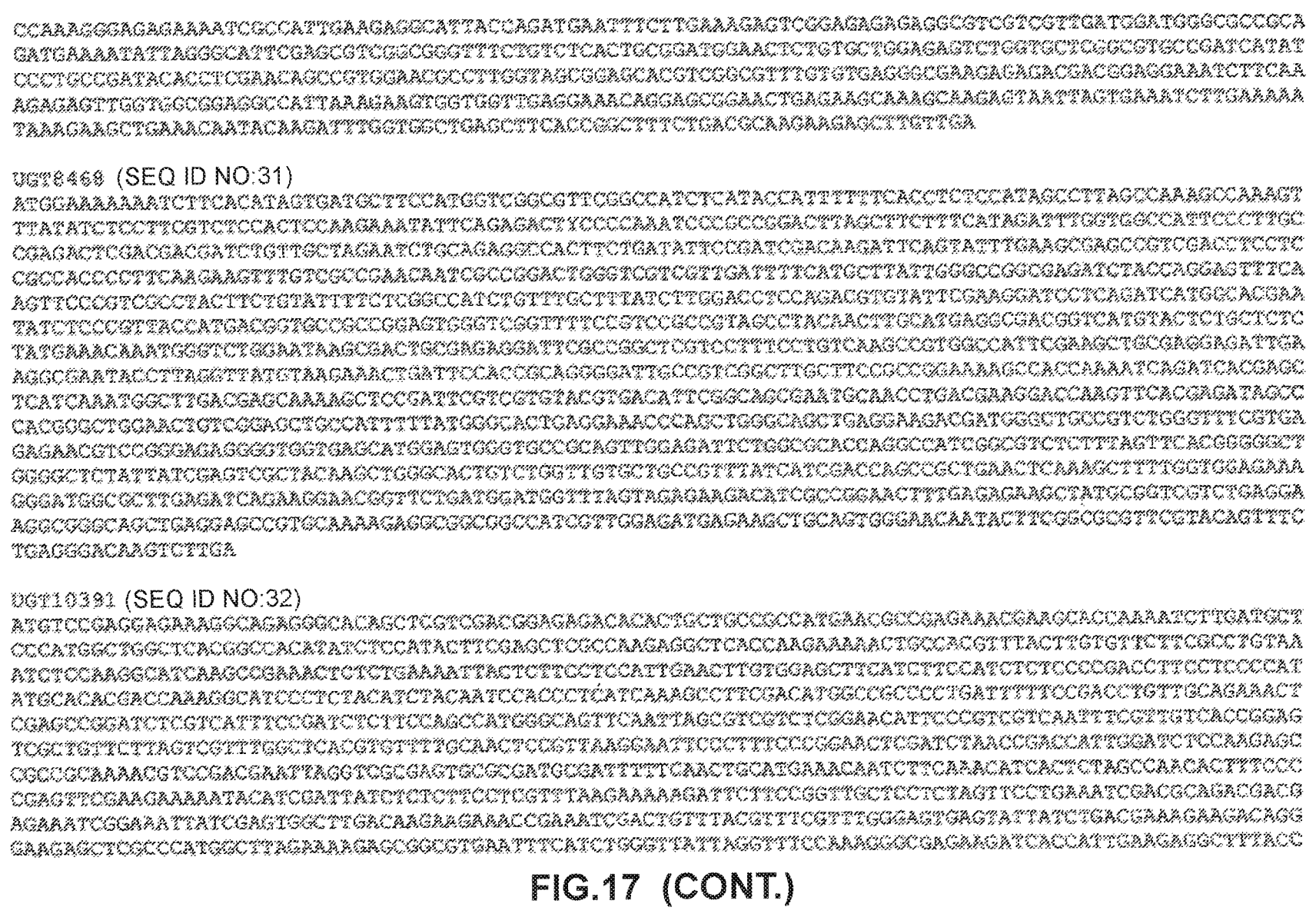

FIG. 17 shows the nucleic acid sequences of UGT98, UGT1495, UGT1817, UGT3494 (partial gene sequence), UGT5914, UGT8468, UGT10391, UGT11789 (partial gene sequence), UGT11999 (partial gene sequence), UGT13679 (partial gene sequence), and UGT15423 (partial gene sequence) (SEQ ID NOs:26-36, respectively).

DETAILED DESCRIPTION OF THE INVENTION

Method of Producing a Mogroside

This document is based on the invention that recombinant hosts such as microorganisms, plant cells, or plants can be developed that express polypeptides useful for the biosynthesis of mogrol (the triterpene core) and various mogrol glycosides (mogrosides). The aglycone mogrol is glycosylated with different numbers of glucose moieties to form various mogroside compounds. Recombinant microorganisms are particularly useful hosts. The recombinant host may be any of the recombinant hosts described herein below in the section "Recombinant host".

Figure 2:
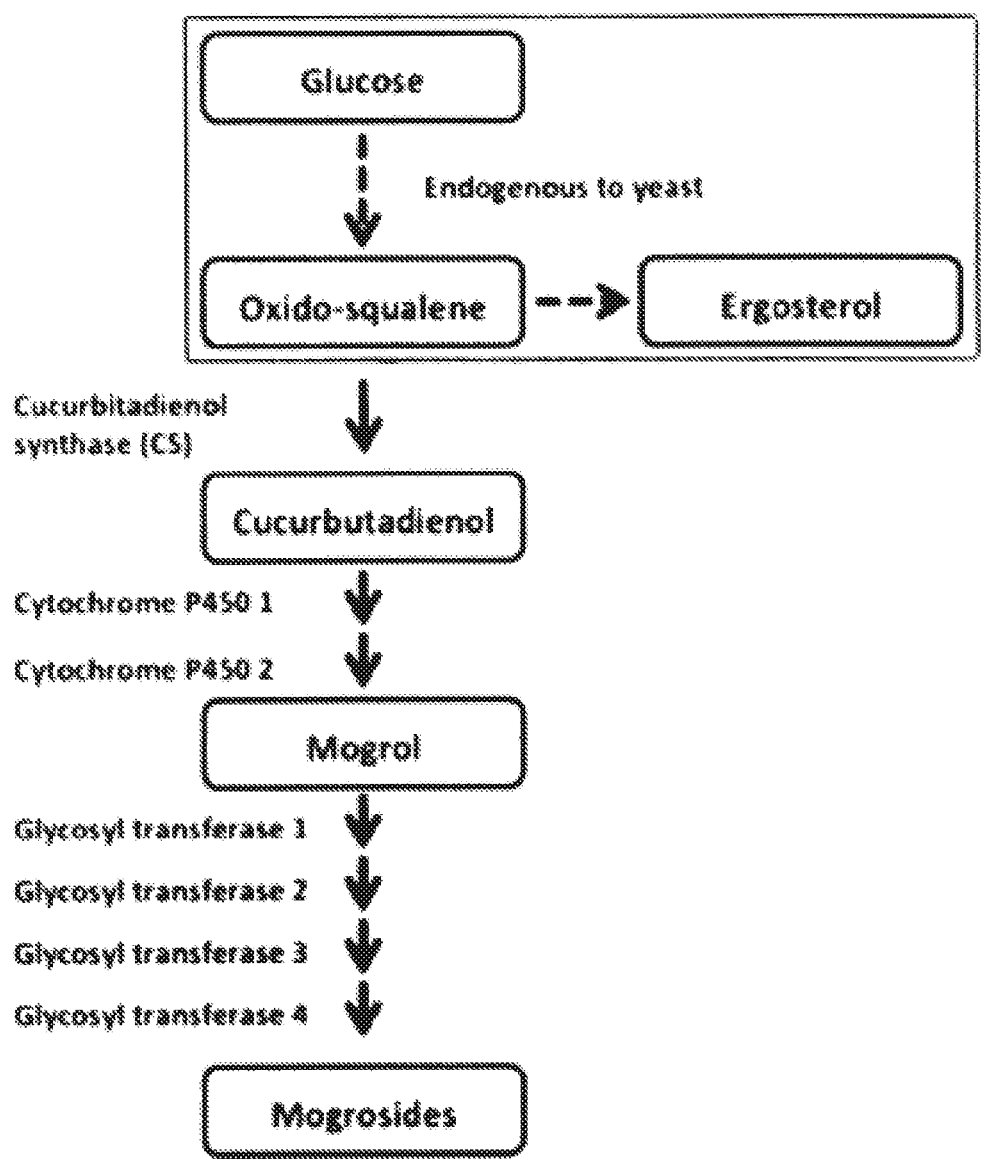
FIG. 2 is a schematic of the pathway for the production of mogrosides from glucose.

Expression of these biosynthetic polypeptides in various microbial chassis allows mogrol and its glycosides to be produced in a consistent, reproducible manner from energy and carbon sources such as sugars, glycerol, $CO_2$, $H_2$ and sunlight. FIG. 2 provides a schematic of the pathway for production of mogrol and various mogrosides from glucose.

It is one aspect of the invention to provide a method of producing a mogroside, wherein the method comprises one or more of the following steps:
Step Ia. Enhancing levels of oxido-squalene
Step Ib. Enhancing levels of dioxido-squalene
Step IIa. Oxido-squalene→cucurbitadienol
Step IIb. Dioxido-squalene→24,25 epoxy cucurbitadienol
Step IIIa. Cucurbitadienol→11-hydroxy-cucurbitadienol
Step IIIb. 24,25 epoxy cucurbitadienol→11-hydroxy-24,25 epoxy cucurbitadienol
Step IVa. 11-hydroxy-cucurbitadienol→mogrol
Step IVb. 11-hydroxy-24,25 epoxy cucurbitadienol→mogrol
Step V mogrol→mogroside Methods and materials for performing each of the steps are described in more detail herein below. Each of the steps of the method results in generation of a product. Said products may also be referred to as "intermediate products" herein. Each step uses a substrate, which may also be referred to as "precursor molecules". It is clear from above that the intermediate products also may serve as precursor molecules for a subsequent step.

Thus, the invention provides methods of producing mogrosides, wherein the method may comprise the steps of
Step Ia. Enhancing levels of oxido-squalene
Step IIa. Oxido-squalene→cucurbitadienol
Step IIIa. Cucurbitadienol→11-hydroxy-cucurbitadienol
Step IVa. 11-hydroxy-cucurbitadienol→mogrol
Step V. mogrol→mogroside
and optionally isolating said mogroside.

The invention also provides methods of producing mogrosides, wherein the method may comprise the steps of
a) Providing oxido-squalene
b) Performing Steps IIa, IIIa, IVa and V identified above
c) optionally isolating said mogroside.

The invention also provides methods of producing mogrosides, wherein the method may comprise the steps of
Step Ib. Enhancing levels of dioxido-squalene
Step IIb. Dioxido-squalene→24,25 epoxy cucurbitadienol
Step IIIb. 24,25 epoxy cucurbitadienol→11-hydroxy-24, 25 epoxy cucurbitadienol
Step IVb. 11-hydroxy-24,25 epoxy cucurbitadienol→mogrol
Step V. mogrol→mogroside
and optionally isolating said mogroside.

The invention also provides methods of producing mogrosides, wherein the method may comprise the steps of
a) providing dioxido-squalene
b) performing steps IIb, IIIb, IVb and V identified above
c) optionally isolating said mogroside.

The invention also provides methods of producing mogrosides, wherein said mogroside may be a higher glycosylated mogroside, wherein the method may comprise the steps of
a) providing cucurbitadienol
b) performing steps IIIa, IVa and V identified above
c) optionally isolating said mogroside.

The invention also provides methods of producing mogrosides, wherein said mogroside may be a higher glycosylated mogroside, wherein the method may comprise the steps of
a) providing 24,25 epoxy cucurbitadienol
b) performing steps IIIb, IVb and V identified above
c) optionally isolating said mogroside.

The invention provides methods of producing mogrosides, wherein the method may comprise the steps of
a) providing mogrol
b) performing step V identified above
c) optionally isolating said mogroside.

The invention provides methods of producing mogrol, wherein the method may comprise the steps of
a) providing dioxido-squalene
b) performing steps IIb, IIb and IVb identified above
c) optionally isolating said mogrol.

In general, the method may be performed either in vitro or in vivo. It is also comprised within the invention that some steps are performed in vitro, whereas others may be performed in vivo. Thus, for example the first steps may be performed in vitro and where after an intermediate product may be fed to recombinant host cells, capable of performing the remaining steps of the method. Alternatively, the first steps may be performed in vivo and where after an intermediate product may be used as substrate for the subsequent step(s) performed in vitro. Other combinations can also be envisaged.

When said methods are performed in vitro each of the steps of the methods may be performed separately. Alternatively, one or more of the steps may be performed within the same mixture. In embodiments wherein some or all of the steps of the methods are performed separately, then the intermediate product of each of the steps may be purified or partly purified before performing the next step.

When said methods are performed in vivo, the methods employ use of a recombinant host expressing one or more of said enzymes or the methods may employ use of several recombinant hosts expressing one or more of said enzymes. The methods may also employ a mixture of recombinant and non-recombinant host. If more than one host is used then the hosts may be co-cultivated, or they may be cultured separately. If the hosts are cultivated separately the intermediate products may be recovered and optionally purified and partially purified and fed to recombinant hosts using the intermediate products as substrates. Useful recombinant hosts to be used with the invention are described herein below.

Said oxido-squalene, dioxido-squalene, cucurbitadienol, 24,25 epoxy cucurbitadienol or mogrol may be provided in any suitable manner. For example said oxido-squalene, dioxido-squalene, cucurbitadienol, 24,25 epoxy cucurbitadienol or mogrol may be provided in isolated form or as part of a composition or an extract. In embodiments of the invention, wherein the methods are performed in vivo, said oxido-squalene, dioxido-squalene, cucurbitadienol, 24,25 epoxy cucurbitadienol or mogrol may be added to the cultivation medium. It is also comprised within the invention that a recombinant host is used, which endogenously expresses oxido-squalene, dioxido-squalene, cucurbitadienol, 24,25 epoxy cucurbitadienol or mogrol.

Recombinant hosts described herein below can be used in methods to produce mogroside compounds. For example, if the recombinant host is a microorganism, the method can include growing the recombinant microorganism in a culture medium under conditions in which one or more of the enzymes catalyzing step(s) of the methods of the invention, e.g. synthases, hydrolases, CYP450s and/or UGTs are expressed. The recombinant microorganism may be grown in a fed batch or continuous process. Typically, the recombinant microorganism is grown in a fermenter at a defined temperature(s) for a desired period of time.

A cell lysate can be prepared from the recombinant host expressing one or more enzymes and be used to contact a substrate, such that mogroside compounds can be produced. For example, a cell lysate can be prepared from the recombinant host expressing one or more UGTs and used to contact mogrol, such that mogroside compounds can be produced.

In some embodiments, mogroside compounds can be produced using whole cells that are fed raw materials that contain precursor molecules, e.g., mogrol. The raw materials may be fed during cell growth or after cell growth. The whole cells may be in suspension or immobilized. The whole cells may be in fermentation broth or in a reaction buffer. In some embodiments a permeabilizing agent may be required for efficient transfer of substrate into the cells.

Levels of products, substrates and intermediates can be determined by extracting samples from culture media for analysis according to published methods. Mogroside compounds can be recovered from the culture or culture medium using various techniques known in the art.

Recombinant Host

This document also feature recombinant hosts. As used herein, the term recombinant host is intended to refer to a host, the genome of which has been augmented by at least one incorporated DNA sequence. Said incorporated DNA sequence may be a heterologous nucleic acid encoding one or more polypeptides. Such DNA sequences include but are not limited to genes that are not naturally present, DNA sequences that are not normally transcribed into RNA or translated into a protein ("expressed"), and other genes or DNA sequences which one desires to introduce into the non-recombinant host. It will be appreciated that typically the genome of a recombinant host described herein is augmented through the stable introduction of one or more recombinant genes. Said recombinant gene may also be a heterologous nucleic acid encoding one or more polypeptides. Generally, the introduced DNA or heterologous nucleic acid is not originally resident in the host that is the recipient of the DNA, but it is within the scope of the invention to isolate a DNA segment from a given host, and to subsequently introduce one or more additional copies of that DNA into the same host, e.g., to enhance production of the product of a gene or alter the expression pattern of a gene. In some instances, the introduced DNA or heterologous nucleic acid will modify or even replace an endogenous gene or DNA sequence by, e.g., homologous recombination or site-directed mutagenesis.

In particular, the recombinant host according to the present invention comprises one or more of the following heterologous nucleic acids:

IIa. Heterologous nucleic acid(s) encoding an enzyme or mixture of enzymes capable of catalysing Step IIa (Oxido-squalene→cucurbitadienol)

IIb. Heterologous nucleic acid(s) encoding an enzyme or mixture of enzymes capable of catalysing Step IIb (Dioxido-squalene→24,25 epoxy cucurbitadienol)

IIIa. Heterologous nucleic acid(s) encoding an enzyme or mixture of enzymes capable of catalysing Step IIIa (Cucurbitadienol→11-hydroxy-cucurbitadienol)

IIIb. Heterologous nucleic acid(s) encoding an enzyme or mixture of enzymes capable of catalysing Step IIIb (24,25 epoxy cucurbitadienol→11-hydroxy-24,25 epoxy cucurbitadienol)

IVa. Heterologous nucleic acid(s) encoding an enzyme or mixture of enzymes capable of catalysing Step IVa (11-hydroxy-cucurbitadienol→mogrol) IVb. Heterologous nucleic acid(s) encoding an enzyme or mixture of enzymes capable of catalysing Step IVb (11-hydroxy-24,25 epoxy cucurbitadienol→mogrol)

V. Heterologous nucleic acid(s) encoding an enzyme or mixture of enzymes capable of catalysing Step V (mogrol→mogroside)

In addition to the heterologous nucleic acids, said recombinant host may have been modified to achieve Step Ia and/or Step Ib.

Enzymes capable of catalysing each of these steps are described herein below in more detail.

In one embodiment of the invention, the recombinant host according to the present invention may comprise the following heterologous nucleic acids:

IIa. Heterologous nucleic acid(s) encoding an enzyme or mixture of enzymes capable of catalysing Step IIa (Oxido-squalene→cucurbitadienol)

IIIa. Heterologous nucleic acid(s) encoding an enzyme or mixture of enzymes capable of catalysing Step IIIa (Cucurbitadienol→11-hydroxy-cucurbitadienol)

IVa. Heterologous nucleic acid(s) encoding an enzyme or mixture of enzymes capable of catalysing Step IVa (11-hydroxy-cucurbitadienol→mogrol)

V. Heterologous nucleic acid(s) encoding an enzyme or mixture of enzymes capable of catalysing Step V (mogrol→mogroside)

and optionally said recombinant host may further have been modified to achieve Step Ia.

Said recombinant host cell is in particular useful in methods for producing mogrosides.

In one embodiment of the invention, the recombinant host according to the present invention may comprise the following heterologous nucleic acids:

IIIa. Heterologous nucleic acid(s) encoding an enzyme or mixture of enzymes capable of catalysing Step IIIa (Cucurbitadienol→11-hydroxy-cucurbitadienol)

IVa. Heterologous nucleic acid(s) encoding an enzyme or mixture of enzymes capable of catalysing Step IVa (11-hydroxy-cucurbitadienol→mogrol)

V. Heterologous nucleic acid(s) encoding an enzyme or mixture of enzymes capable of catalysing Step V (mogrol→mogroside)

Said recombinant host cell is in particular useful in methods for producing mogrosides comprising a step of providing curcubutadienol.

In one embodiment of the invention, the recombinant host according to the present invention may comprise the following heterologous nucleic acids:

V Heterologous nucleic acid(s) encoding an enzyme or mixture of enzymes capable of catalysing Step V (mogrol→mogroside)

Said recombinant host cell is in particular useful in methods for producing mogrosides comprising a step of providing mogrol.

In one embodiment of the invention, the recombinant host according to the present invention may comprise the following heterologous nucleic acids:

IIb. Heterologous nucleic acid(s) encoding an enzyme or mixture of enzymes capable of catalysing Step IIb (Dioxido-squalene→24,25 epoxy cucurbitadienol)

IIIb. Heterologous nucleic acid(s) encoding an enzyme or mixture of enzymes capable of catalysing Step IIIb (24,25 epoxy cucurbitadienol→11-hydroxy-24,25 epoxy cucurbitadienol)

IVb. Heterologous nucleic acid(s) encoding an enzyme or mixture of enzymes capable of catalysing Step IVb (11-hydroxy-24,25 epoxy cucurbitadienol→mogrol)

V. Heterologous nucleic acid(s) encoding an enzyme or mixture of enzymes capable of catalysing Step V (mogrol→mogroside)

And optionally said recombinant host may have been modified to achieve Step Ib.

Said recombinant host cell is in particular useful in methods for producing mogrosides.

In one embodiment of the invention, the recombinant host according to the present invention may comprise the following heterologous nucleic acids:

IIIb. Heterologous nucleic acid(s) encoding an enzyme or mixture of enzymes capable of catalysing Step IIIb (24,25 epoxy cucurbitadienol→11-hydroxy-24,25 epoxy cucurbitadienol)

IVb. Heterologous nucleic acid(s) encoding an enzyme or mixture of enzymes capable of catalysing Step IVb (11-hydroxy-24,25 epoxy cucurbitadienol→mogrol)

V. Heterologous nucleic acid(s) encoding an enzyme or mixture of enzymes capable of catalysing Step V (mogrol→mogroside)

Said recombinant host cell is in particular useful in methods for producing mogrosides comprising a step of providing 24,25 epoxy cucurbitadienol.

In one embodiment of the invention, the recombinant host according to the present invention may comprise the following heterologous nucleic acids:

IIb. Heterologous nucleic acid(s) encoding an enzyme or mixture of enzymes capable of catalysing Step IIb (Dioxido-squalene→24,25 epoxy cucurbitadienol)

IIIb. Heterologous nucleic acid(s) encoding an enzyme or mixture of enzymes capable of catalysing Step IIIb (24,25 epoxy cucurbitadienol→11-hydroxy-24,25 epoxy cucurbitadienol)

IVb. Heterologous nucleic acid(s) encoding an enzyme or mixture of enzymes capable of catalysing Step IVb (11-hydroxy-24,25 epoxy cucurbitadienol→mogrol)

and optionally said recombinant host may have been modified to achieve Step Ib.

Said recombinant host cell is in particular useful in methods for producing mogrol.

Suitable recombinant hosts include microorganisms, plant cells, and plants.

Thus, in one embodiment, a recombinant host that produces a mogroside compound can include a recombinant gene encoding at least a first UGT selected from the group consisting of 73C3, 73C6, 85C2, 73C5, and 73E1, and a recombinant gene encoding at least a second UGT selected from the group consisting of UGT98, UGT1495, UGT1817, UGT5914, UGT8468 and UGT10391. For example, a recombinant host can include a recombinant gene encoding at least one UGT selected from 73C3, 73C6, 85C2, and 73E1; a recombinant gene encoding 73C5; and a recombinant gene encoding at least one UGT selected from the group consisting of UGT98, UGT1495, UGT1817, UGT5914, UGT8468 and UGT10391. One or more of the following also can be included in a recombinant host: a recombinant gene encoding a cucurbitadienol synthase (e.g., from *Cucurbita pepo* or monk fruit); a recombinant gene encoding a cytochrome P450 polypeptide selected from the group CYP533, CYP937, CYP1798, CYP1994, CYP2048, CYP2740, CYP3404, CYP3968, CYP4112, CYP4149, CYP4491, CYP5491, CYP6479, CYP7604, CYP8224, CYP8728, CYP10020, and CYP10285 (SEQ ID NOs:3-20, respectively); and a recombinant gene encoding a squalene synthase (e.g., from *Gynostemma pentaphyllum* or *Arabidopsis thaliana*). CYP5491 has previously also been referred to as CYP87.

At least one of the genes in the recombinant host is a recombinant gene, the particular recombinant gene(s) depending on the species or strain selected for use. Additional genes or biosynthetic modules can be included in order to increase yield of mogrol and mogrosides, improve efficiency with which energy and carbon sources are converted to mogrol and mogrosides, and/or to enhance productivity from the cell culture or plant.

The recombinant host further can include a recombinant gene encoding a cucurbitadienol synthase and/or a recombinant gene encoding a cytochrome P450 polypeptide (e.g., CYP533, CYP937, CYP1798, CYP1994, CYP2048, CYP2740, CYP3404, CYP3968, CYP4112, CYP4149, CYP4491, CYP5491, CYP6479, CYP7604, CYP8224, CYP8728, CYP10020, or CYP10285) and/or a recombinant gene encoding a squalene synthase.

It is also comprised within the invention that the recombinant host may be modified in order to reduce glucanase activity, in particular glucanase activity, which may result in deglucosylation of mogrosides. Thus, the recombinant host may for example be modified to reduce of even abolish exo-1,3-beta-Glucanase activity. In embodiments of the invention when the recombinant host is yeast, this may be accomplished by deletion of the EXG1 gene and/or of the EXG2 gene, both of which are encoding an exo-1,3-beta-Glucanase.

The term "recombinant gene" refers to a gene or DNA sequence that is introduced into a recipient host, regardless of whether the same or a similar gene or DNA sequence may already be present in such a host. The term "heterologous nucleic acid" refers to a nucleic acid that is introduced into a recipient host, wherein said host does not endogenously comprise said nucleic acid. "Introduced," or "augmented" in this context, is known in the art to mean introduced or augmented by the hand of man. Thus, a recombinant gene may be a DNA sequence from another species, or may be a DNA sequence that originated from or is present in the same species, but has been incorporated into a host by recombinant methods to form a recombinant host. It will be appreciated that a recombinant gene that is introduced into a host can be identical to a DNA sequence that is normally present in the host being transformed, and is introduced to provide one or more additional copies of the DNA to thereby permit overexpression or modified expression of the gene product of that DNA.

A recombinant gene encoding a polypeptide described herein comprises the coding sequence for that polypeptide, operably linked in sense orientation to one or more regulatory regions suitable for expressing the polypeptide. Because many microorganisms are capable of expressing multiple gene products from a polycistronic mRNA, multiple polypeptides can be expressed under the control of a single regulatory region for those microorganisms, if desired. A coding sequence and a regulatory region are considered to be operably linked when the regulatory region and coding sequence are positioned so that the regulatory region is effective for regulating transcription or translation of the sequence. Typically, the translation initiation site of the translational reading frame of the coding sequence is positioned between one and about fifty nucleotides downstream of the regulatory region for a monocistronic gene. In many cases, the coding sequence for a polypeptide described herein is identified in a species other than the recombinant host, i.e., is a heterologous nucleic acid. Thus, if the recombinant host is a microorganism, the coding sequence can be from other prokaryotic or eukaryotic microorganisms, from plants or from animals. In some case, however, the coding sequence is a sequence that is native to the host and is being reintroduced into that organism. A native sequence can often be distinguished from the naturally occurring sequence by the presence of non-natural sequences linked to the exogenous nucleic acid, e.g., non-native regulatory sequences flanking a native sequence in a recombinant nucleic acid construct. Such sequences may then also be considered heterologous nucleic acids. In addition, stably transformed exogenous nucleic acids typically are integrated at positions other than the position where the native sequence is found.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). A regulatory region is operably linked to a coding sequence by positioning the regulatory region and the coding sequence so that the regulatory region is effective for regulating transcription or translation of the sequence. For example, to operably link a coding sequence and a promoter sequence, the translation initiation site of the translational reading frame of the coding sequence is typically positioned between one and about fifty nucleotides downstream of the promoter. A regulatory region can, however, be positioned at further distance, for example as much as about 5,000 nucleotides upstream of the translation initiation site, or about 2,000 nucleotides upstream of the transcription start site.

The choice of regulatory regions to be included depends upon several factors, including, but not limited to, efficiency, selectability, inducibility, desired expression level, and preferential expression during certain culture stages. It is a routine matter for one of skill in the art to modulate the expression of a coding sequence by appropriately selecting and positioning regulatory regions relative to the coding sequence. It will be understood that more than one regulatory region may be present, e.g., introns, enhancers, upstream activation regions, transcription terminators, and inducible elements. One or more genes can be combined in a recombinant nucleic acid construct in "modules" useful for a discrete aspect of mogroside production. Combining a plurality of genes in a module, particularly a polycistronic module, facilitates the use of the module in a variety of species. In addition to genes useful for mogroside production, a recombinant construct typically also contains an origin of replication, and one or more selectable markers for maintenance of the construct in appropriate species.

It will be appreciated that because of the degeneracy of the genetic code, a number of nucleic acids can encode a particular polypeptide; i.e., for many amino acids, there is more than one nucleotide triplet that serves as the codon for the amino acid. Thus, codons in the coding sequence for a given polypeptide can be modified such that optimal expression in a particular host is obtained, using appropriate codon bias tables for that host (e.g., microorganism). Nucleic acids may also be optimized to a GC-content preferable to a particular host, and/or to reduce the number of repeat sequences. As isolated nucleic acids, these modified sequences can exist as purified molecules and can be incorporated into a vector or a virus for use in constructing modules for recombinant nucleic acid constructs.

A number of prokaryotes and eukaryotes are suitable for use as recombinant hosts with the present invention. Thus, the recombinant host may e.g. be selected from the group consisting of gram-negative bacteria, yeast and fungi. A species and strain selected for use as a mogroside production strain is first analyzed to determine which production genes are endogenous to the strain and which genes are not present. Genes for which an endogenous counterpart is not present in the strain are assembled in one or more recombinant constructs, which are then transformed into the strain in order to supply the missing function(s). Thus, it may be analysed which of steps IIa, IIIa, IVa and V are already performed by the host, and then said host may be modified by introduction of heterologous nucleic acids encoding enzymes catalyzing the remaining steps. Similarly, it may be analysed which of steps IIb, IIIb, IVb and V are already performed by the host, and then said host may be modified by introduction of heterologous nucleic acids encoding enzymes catalyzing the remaining steps. As mentioned before the recombinant host may also be modified to increase levels of oxido-squalene and/or dioxido-squalene.

Exemplary prokaryotic and eukaryotic species useful as recombinant with the present invention are described in more detail below. However, it will be appreciated that other species may be suitable. For example, the recombinant host may be in a genus selected from the group consisting of *Agaricus*, *Aspergillus*, *Bacillus*, *Candida*, *Corynebacterium*, *Escherichia*, *Fusarium/Gibberella*, *Kluyveromyces*, *Laetiporus*, *Lentinus*, *Phaffia*, *Phanerochaete*, *Pichia*, *Physcomitrella*, *Rhodoturula*, *Saccharomyces*, *Schizosaccharomyces*, *Sphaceloma*, *Xanthophyllomyces* and *Yarrowia*. Exemplary species from such genera useful as recombinant hosts include *Lentinus tigrinus*, *Laetiporus sulphureus*, *Phanerochaete chrysosporium*, *Pichia pastoris*, *Physcomitrella patens*, *Rhodoturula glutinis*, *Rhodoturula mucilaginosa*, *Phaffia rhodozyma*, *Xanthophyllomyces dendrorhous*, *Fusarium fujikuroi/Gibberella fujikuroi*, *Candida utilis* and *Yarrowia lipolytica*. In some embodiments, a recombinant host may be a microorganism, for example an Ascomycete such as *Gibberella fujikuroi*, *Kluyveromyces lactis*, *Schizosaccharomyces pombe*, *Aspergillus niger*, or *Saccharomyces cerevisiae*. In some embodiments, a recombinant host may be a microorganism for example a prokaryote such as *Escherichia coli*, *Rhodobacter sphaeroides*, or *Rhodobacter capsulatus*. It will be appreciated that certain microorganisms can be used to screen and test genes of interest in a high throughput manner, while other microorganisms with desired productivity or growth characteristics can be used for large-scale production of mogroside compounds. In particular, food grade microorganisms may be useful for large-scale production purposes.

*Saccharomyces cerevisiae*

As described above the recombinant host may for example be *Saccharomyces cerevisiae*. *Saccharomyces cerevisiae* is a widely used chassis organism in synthetic biology, and can be used as the recombinant microorganism platform. There are libraries of mutants, plasmids, detailed computer models of metabolism and other information available for *S. cerevisiae*, allowing for rational design of various modules to enhance product yield. Methods are known for making recombinant microorganisms. The VG4 strain of *S. cerevisiae* from Brochado et al. 2010 (Microb Cell Fact. 9:84) may be particularly useful. VG4 has the genotype of pdc1Δgdh1Δ↑GDH2. Another very useful strain of *S. cerevisiae* is BY4742 described herein below in Example 9, or the yeast strain described in Kirby, J et al in FEBS Journal 275 (2008) 1852-1859.

*Aspergillus* spp.

The recombinant host may also be a *Aspergillus* species such as *A. oryzae*, *A. niger* and *A. sojae*. *Aspergillus* spp, such as the aforementioned are widely used microorganisms in food production, and can also be used as the recombinant microorganism platform. Nucleotide sequences are available for genomes of *A. nidulans*, *A. fumigatus*, *A. oryzae*, *A. clavatus*, *A. flavus*, *A. niger*, and A. ferrous, allowing rational design and modification of endogenous pathways to enhance flux and increase product yield. Any of these may be used recombinant hosts. Metabolic models have been developed for *Aspergillus*, as well as transcriptomic studies and proteomics studies. *A. niger* is cultured for the industrial production of a number of food ingredients such as citric acid and gluconic acid, and thus species such as *A. niger* are generally suitable for the production of food ingredients.

*Escherichia coli*

The recombinant host may also be *Escherichia coli*, which is another widely used platform organism in synthetic biology. Similar to *Saccharomyces*, there are libraries of mutants, plasmids, detailed computer models of metabolism and other information available for *E. coli*, allowing for rational design of various modules to enhance product yield. Methods similar to those described above for *Saccharomyces* can be used to make recombinant *E. coli* microorganisms.

*Rhodobacter* spp.

The recombinant host may also be *Rhodobacter*. Similar to *E. coli*, there are libraries of mutants available as well as suitable plasmid vectors, allowing for rational design of various modules to enhance product yield. Methods similar to those described above for *E. coli* can be used to make recombinant *Rhodobacter* microorganisms.

*Physcomitrella* spp.

The recombinant host may also be *Physcomitrella* mosses. *Physcomitrella* mosses, when grown in suspension culture, have characteristics similar to yeast or other fungal cultures. This genera is becoming an important type of cell for production of plant secondary metabolites, which can be difficult to produce in other types of cells.

Step Ia—Enhancing Levels of Oxido-Squalene

As described herein above the methods of the invention may comprise a step of enhancing the levels of oxido-squalene. This is in particular relevant in methods comprising step IIa, wherein step IIa is performed in vivo. Step Ia may in particular be performed by modifying the recombinant host to be used with the methods in a manner enhancing the levels of oxido-squalene in said recombinant host. The invention also relates to recombinant hosts modified to enhance the levels of oxido-squalene.

Figure 3:
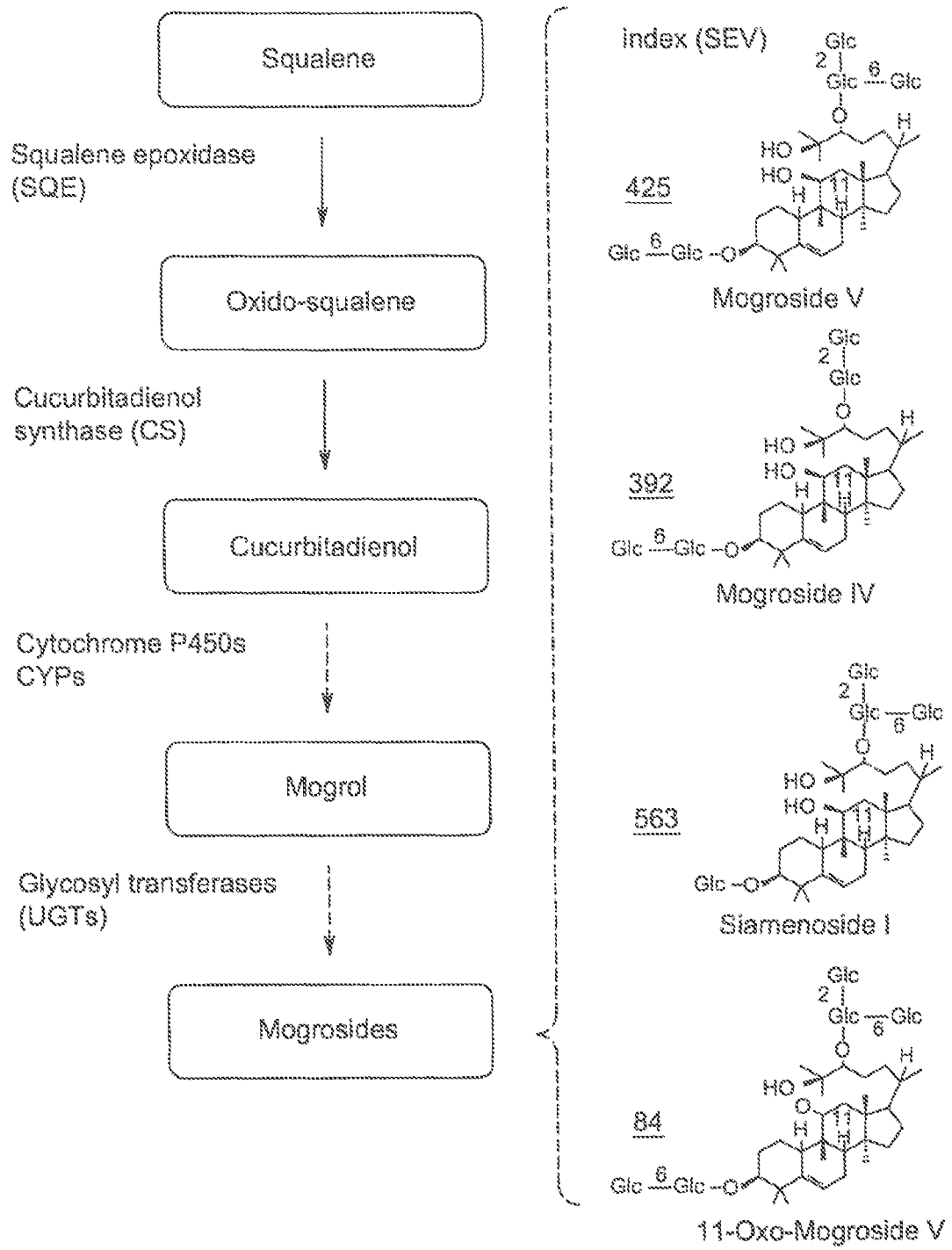
FIG. 3 is a schematic of the production of mogrol glycosides (mogrosides) from squalene.

Thus, the methods may also comprise one or more steps leading to formation of oxido-squalene, in particular to the formation of 2,3-oxido-squalene. Said steps are preferably performed prior to step IIa described below, or simultaneously herewith. FIG. 3 provides a schematic of the pathway from squalene to mogrosides.

One step in the production of oxido-squalene may be production of squalene from farnesyl pyrophosphate. One enzyme that catalyzes the production of squalene from farnesyl pyrophosphate is squalene synthase (also referred to as squalene synthase). Said squalene synthase may be any enzyme classified under EC 2.5.1.21. The reaction is typically thought to proceed using NADPH as a cosubstrate. Accordingly, the method may comprise a step of production of squalene from farnesyl pyrophosphate catalyzed by a squalene synthase in the presence of NADPH. In embodiments of the invention wherein the methods are performed in vivo, the recombinant host may thus comprise a heterologous nucleic acid encoding a squalene synthase. Some recombinant hosts may comprise an endogenous squalene synthase in which case the endogenous enzyme may suffice. Endogenous squalene production pathways exist in yeast metabolism, and accordingly, if the recombinant host is yeast, then said step may be endogenous to the recombinant host.

The squalene synthase may be any useful squalene synthase. For example the squalene synthase may be squalene synthase from *Gynostemma pentaphyllum* (protein accession number C4P9M2), another cucurbitaceae family plant. The squalene synthase may also be selected from the groups consisting of squalene synthase of *Arabidopsis thaliana* (protein accession number C4P9M3), *Brassica napus, Citrus macrophylla, Euphorbia tirucalli* (protein accession number B9WZW7), *Glycine max, Glycyrrhiza glabra* (protein accession number Q42760, Q42761), *Glycrrhiza uralensis* (protein accession number D6QX40, D6QX41, D6QX42, D6QX43, D6QX44, D6QX45, D6QX47, D6QX39, D6QX55, D6QX38, D6QX53, D6QX37, D6QX35, B5AID5, B5AID4, B5AID3, C7EDD0, C6KE07, C6KE08, C7EDC9), *Lotusjaponicas* (protein accession number Q84LE3), *Medicago truncatula* (protein accession number Q8GSL6), *Pisum sativum, Ricinus communis* (protein accession number B9RHC3), and *Prunus mume* and functional homologues of any of the aforementioned sharing at least at least 70%, such as at least 80%, for example at least 90%, such as at least 95%, for example at least 98% sequence identity therewith. Increased copy numbers, heterologous nucleic acids encoding squalene synthase, or increased expression of the native squalene synthase may improve levels of mogrosides produced in a recombinant host.

Another step in the production of oxido-squalene may be production of oxido-squalene from squalene. One enzyme that catalyzes the production of oxido-squalene from squalene is squalene epoxidase (also referred to as squalene monoxygenase). Said squalene epoxidase may be any enzyme classified under EC 1.4.99.7. The reaction is typically thought to proceed using NADPH as a cosubstrate. Accordingly, the method may comprise a step of production of oxido-squalene from squalene catalyzed by a squalene epoxidase in the presence of NADPH. In embodiments of the invention wherein the methods are performed in vivo, the recombinant host may thus comprise a heterologous nucleic acid encoding a squalene epoxidase. Some recombinant hosts may comprise an endogenous squalene epoxidase, in which case the endogenous enzyme may suffice. Endogenous oxido-squalene production pathways exist in yeast metabolism, and accordingly, if the recombinant host is yeast, then said step may be endogenous to the recombinant host. However, in order to enhance the level of oxido-squalene it may never-the-less be advantageous to express addition squalene epoxidase.

The squalene epoxidase may be any useful squalene epoxidase. The squalene epoxidase may for example be squalene epoxidase from *Gynostemma pentaphyllum* (protein accession number C4P9M2), a cucurbitaceae family plant. The squalene epoxidase may also be selected from the group consisting of squalene epoxidase of *Arabidopsis thaliana* (protein accession number Q9SM02, O65403, O65402, O65404, O81000, or Q9T064), *Brassica napus* (protein accession number O65727, O65726), *Euphorbia tirucalli* (protein accession number A7VJN1), *Medicago truncatula* (protein accession number Q8GSM8, Q8GSM9), *Pisum sativum*, and *Ricinus communis* (protein accession number B9R6V0, B9S7W5, B9S6Y2, B9T0Y3, B9S7T0, B9SX91) and functional homologues of any of the aforementioned sharing at least 70%, such as at least 80%, for example at least 90%, such as at least 95%, for example at least 98% sequence identity therewith. Increased copy numbers, heterologous nucleic acids encoding squalene epoxidase, or increased expression of the native squalene epoxidase may improve levels of mogrosides produced in a recombinant host.

The squalene epoxidase may also be the product of the ERG1 gene of *S. cerevisiae*. Thus, the squalene epoxidase may be a polypeptide of SEQ ID NO:54 or a functional homologues thereof sharing at least 70%, such as at least 80%, for example at least 90%, such as at least 95%, for example at least 98% sequence identity therewith.

In one embodiment the recombinant host comprises a heterologous nucleic acid encoding a squalene epoxidase operably linked to sequence directing high expression of said squalene epoxidase in said host cell. Thus, the squalene epoxidase may be endogenous to the recombinant host, but the expression level may be increased by additional copies of nucleic acids encoding the squalene epoxidase and/or by use of stronger promoters.

Oxido-squalene serves as a substrate for production of lanosterol. Thus, in one embodiment the level of oxido-squalene may be increased by reducing the activity of lanosterol synthase. In recombinant hosts expressing an endogenous lanosterol synthase, this may be achieved by substituting the endogenous promoter directed expression of lanosterol synthase with a weaker promoter directing expression of a lower level of lanosterol synthase. In yeast the ERG7 gene encodes lanosterol synthase. Thus, when the recombinant host is yeast, then the promoter of the ERG7 gene may be substituted for another promoter, which directs a level of expression, which is lower than the endogenous expression level of ERG7. The lanosterol synthase may thus be the product of the ERG7 gene of *S. cerevisiae*, the sequence of which is provided herein as SEQ ID NO:55 or a functional homologues thereof sharing at least 70%, such as at least 80%, for example at least 90%, such as at least 95%, for example at least 98% sequence identity therewith.

Examples of useful weak promoters include the methionine-repressible promoter of the MET3 gene or the CUP1 cupper inducible promoter. Non-limiting examples of how to reduce the activity of lanosterol synthase are described in Example 9 herein below or in Kirby et al., 2008 (vide supra) both of which are incorporated by reference herein. The sequence of *S. cerevisiae* lanosterol synthase is provided as SEQ ID NO:55. Thus, when the recombinant host is *S. cerevisiae*, then it is preferred that the polypeptide of SEQ ID NO:55 is expressed at a lower level than the level of said polypeptide in wild type *S. cerevisiae*. Similarly, when the recombinant host expresses a polypeptide similar to the polypeptide of SEQ ID NO:55 (e.g. at least 70% identical to SEQ ID NO:55), then it is preferred that said polypeptide at least 70% identical to SEQ ID NO:55 is expressed at a lower level than the level of said polypeptide in the wild type host.

In addition, expression of a truncated form of the enzyme 3-hydroxy-3-methylglutaryl-CoA reductase (tHMG1) may also lead enhanced levels of oxido-squalene. A useful truncated form of yeast HMG reductase (tHMG1) is described in Donald et al., 1997, Appl. Environ. Microbiol. 63, 3341-3344.

Step Ib—Enhancing Levels of Dioxido-Squalene

As described herein above the methods of the invention may comprise a step of enhancing the levels of dioxido-squalene. This is in particular relevant in methods comprising step IIb, wherein step IIb is performed in vivo. Step Ib may in particular be performed by modifying the recombinant host to be used with the methods in a manner enhancing the levels of dioxido-squalene in said recombinant host. The invention also relates to recombinant hosts modified to enhance the levels of dioxido-squalene.

Thus, the methods may also comprise one or more steps leading to enhanced levels of dioxido-squalene. Said steps are preferably performed prior to step IIb described below, or simultaneously herewith.

The present invention describes that the levels of dioxido-squalene in particular may be enhanced by high expression of a squalene epoxidase. Said squalene epoxidase may be any of the squalene epoxidase described herein above in the section "Step Ia—Enhancing levels of oxido-squalene". In particular, the squalene epoxidase may be the product of the ERG1 gene of *S. cerevisiae*. Thus, the squalene epoxidase may be a polypeptide of SEQ ID NO:54 or a functional homologues thereof sharing at least 70%, such as at least 80%, for example at least 90%, such as at least 95%, for example at least 98% sequence identity therewith. High expression level may be achieved by introducing a heterologous nucleic acid encoding a squalene epoxidase into the host cell operably linked to sequence directing high expression of said squalene epoxidase in said host cell. Thus, the squalene epoxidase may be endogenous to the recombinant host, but the expression level may be increased by additional copies of nucleic acids encoding the squalene epoxidase and/or by use of stronger promoters.

The levels of dioxido-squalene may also be enhanced by reducing the activity of lanosterol synthase. The activity of lanosterol synthase may be reduced by any of the methods described herein above in the section "Step Ia—Enhancing levels of oxido-squalene".

The levels of dioxido-squalene may also be enhanced by expression of a truncated form of the enzyme 3-hydroxy-3-methylglutaryl-CoA reductase (tHMG1) may also lead enhanced levels of oxido-squalene. A useful truncated form of yeast HMG reductase (tHMG1) is described in Donald et al., 1997, Appl. Environ. Microbiol. 63, 3341-3344.

Step IIa—Oxido-Squalene→Cucurbitadienol

As described herein above the methods of the invention may comprise a step of producing cucurbitadienol from oxido-squalene, and in particular from 2,3-oxido-squalene using an enzyme or mixture of enzymes capable of catalysing conversion of oxido-squalene to form cucurbitadienol. The invention also relates to recombinant hosts comprising a heterologous nucleic acid encoding an enzyme capable of catalysing conversion of oxido-squalene to cucurbitadienol.

The step may be performed in vitro by incubating a composition comprising oxido-squalene with said enzyme or a mixture of enzymes capable of catalyzing conversion of oxido-squalene to form cucurbitadienol.

The step may also be performed in vivo in a recombinant host comprising heterologous nucleic acid(s) encoding an enzyme or a mixture of enzymes capable of catalyzing conversion of oxido-squalene to form cucurbitadienol. Said recombinant host may be capable of producing oxido-squalene, for example because the recombinant host expresses one or more enzymes of the oxido-squalene biosynthesis pathway.

Alternatively, oxido-squalene may be provided to said recombinant host for example in the cultivation medium.

Said enzyme or mixture of enzyme capable of catalyzing conversion of oxido-squalene to form cucurbitadienol preferably comprises or consists of a cucurbitadienol synthase.

Said cucurbitadienol synthase may be any useful cucurbitadienol synthase, for example a cucurbitadienol synthase, which has been classified as an oxidosqualene cyclase, such as the oxidosqualene cyclase described by Shibuya, *Tetrahedron*, Vol 60: pp. 6995-7003 (2004).

The amino acid sequence of a cucurbitadienol synthase from *Cucurbita pepo* is provided herein as SEQ ID NO:1 and also is provided in GenBank® under Protein Accession No. BAD34645.1. In one embodiment of the invention the cucurbitadienol synthase is a polypeptide of SEQ ID NO:1 or a functional homologue thereof sharing at least 70%, such as at least 80%, for example at least 90%, such as at least 95%, for example at least 98% sequence identity therewith.

As described in Example 5, the cucurbitadienol synthase from monk fruit was identified and the sequence of the C-terminal portion of the polypeptide determined. The amino acid sequence of the C-terminal portion of the monk fruit polypeptide is provided herein as SEQ ID NO:2. SEQ ID NO:2 is 97.5% identical to residues 515 to 764 of the *C. pepo* polypeptide set forth in SEQ ID NO:1. Thus, in one embodiment of the invention the cucurbitadienol synthase is a polypeptide comprising the amino acid sequence set forth in SEQ ID NO:2.

In a preferred embodiment the cucurbitadienol synthase is the polypeptide of SEQ ID NO:43 or a functional homologue thereof sharing at least 70%, such as at least 80%, for example at least 90%, such as at least 95%, for example at least 98% sequence identity therewith.

Other homologous proteins can be found of similar length and having approximately 70% homology or higher to SEQ ID NO:1. Such homologs include the polypeptides from *Lotus japonicas* (BAE53431), *Populus trichocarpa* (XP_002310905), *Actaea racemosa* (ADC84219), *Betula platyphylla* (BAB83085), *Glycyrrhiza glabra* (BAA76902), *Vitis vinifera* (XP_002264289), *Centella asiatica* (AAS01524), *Panax ginseng* (BAA33460), and *Betula platyphylla* (BAB83086). The cucurbitadienol synthase may be any of the aforementioned or a functional homologue thereof sharing at least 70%, such as at least 80%, for example at least 90%, such as at least 95%, for example at least 98% sequence identity therewith.

Step IIb—Dioxido-Squalene→24,25 Epoxy Cucurbitadienol

As described herein above the methods of the invention may comprise a step of producing 24,25 epoxy cucurbitadienol from dioxido-squalene using an enzyme or mixture of enzymes capable of catalysing conversion of oxido-squalene to form cucurbitadienol. The invention also relates to recombinant hosts comprising a heterologous nucleic acid encoding an enzyme capable of catalysing conversion of dioxido-squalene to 24,25 epoxy cucurbitadienol.

The step may be performed in vitro by incubating a composition comprising dioxido-squalene with said enzyme or a mixture of enzymes capable of catalyzing conversion of dioxido-squalene to form 24,25 epoxy cucurbitadienol.

The step may also be performed in vivo in a recombinant host comprising heterologous nucleic acid(s) encoding an enzyme or a mixture of enzymes capable of catalyzing conversion of dioxido-squalene to 24,25 epoxy cucurbitadienol. Said recombinant host may be capable of producing dioxido-squalene, for example because the recombinant host expresses one or more enzymes of the dioxido-squalene biosynthesis pathway. However, it is preferred that said recombinant host has been modified to enhance levels of dioxido-squalene in any of the manners described herein above in the section "Step Ib Enhancing levels of dioxido-squalene". Alternatively, dioxido-squalene may be provided to said recombinant host for example in the cultivation medium.

Said enzyme or mixture of enzyme capable of catalyzing conversion of dioxido-squalene to 24,25 epoxy cucurbitadienol preferably comprises or consists of a cucurbitadienol synthase.

Said cucurbitadienol synthase may be any useful cucurbitadienol synthase, for example a cucurbitadienol synthase, which has been classified as an oxidosqualene cyclase, such as the oxidosqualene cyclase described by Shibuya, *Tetrahedron*, Vol 60: pp. 6995-7003 (2004). In one embodiment of the invention the cucurbitadienol synthase is a polypeptide of SEQ ID NO:1 or a functional homologue thereof sharing at least 70%, such as at least 80%, for example at least 90%, such as at least 95%, for example at least 98% sequence identity therewith.

In a preferred embodiment the cucurbitadienol synthase is the polypeptide of SEQ ID NO:43 or a functional homologue thereof sharing at least 70%, such as at least 80%, for example at least 90%, such as at least 95%, for example at least 98% sequence identity therewith.

Other homologous proteins can be found of similar length and having approximately 70% homology or higher to SEQ ID NO:1. Such homologs include the polypeptides from *Lotus japonicas* (BAE53431), *Populus trichocarpa* (XP_002310905), *Actaea racemosa* (ADC84219), *Betula platyphylla* (BAB83085), *Glycyrrhiza glabra* (BAA76902), *Vitis vinifera* (XP_002264289), *Centella asiatica* (AAS01524), *Panax ginseng* (BAA33460), and *Betula platyphylla* (BAB83086). The cucurbitadienol synthase may be any of the aforementioned or a functional homologue thereof sharing at least 70%, such as at least 80%, for example at least 90%, such as at least 95%, for example at least 98% sequence identity therewith.

Step IIIa—Cucurbitadienol→11-Hydroxy-Cucurbitadienol

As described herein above the methods of the invention may comprise a step of producing 11-hydroxy-cucurbitadienol from cucurbitadienol using an enzyme or a mixture of enzymes capable of catalysing hydroxylation of cucurbitadienol to form 11-hydroxy-cucurbitadienol.

The step may be performed in vitro by incubating a composition comprising cucurbitadienol with said enzyme capable of catalyzing hydroxylation of cucurbitadienol to form 11-hydroxy-cucurbitadienol.

The step may also be performed in vivo in a recombinant host comprising heterologous nucleic acid(s) encoding an enzyme capable of catalyzing hydroxylation of cucurbitadienol to form 11-hydroxy-cucurbitadienol. Said recombinant host may be capable of producing cucurbitadienol, for example because the recombinant host expresses one or more enzymes of the cucurbitadienol biosynthesis pathway. Alternatively, cucurbitadienol may be provided to said recombinant host for example in the cultivation medium.

Said enzyme capable of catalyzing hydroxylation of cucurbitadienol to form 11-hydroxy-cucurbitadienol preferably is selected from the group of cytochrome P450 enzymes.

As indicated in Example 7, one or more of CYP533, CYP937, CYP1798, CYP1994, CYP2048, CYP2740, CYP3404, CYP3968, CYP4112, CYP4149, CYP4491, CYP5491, CYP6479, CYP7604, CYP8224, CYP8728, CYP10020, and CYP10285 (encoded by SEQ ID NOs: 3-20, respectively) can be used to produce mogrol. eYAC technology can be used to assess activity of the cytochrome P450 enzymes as set forth in Example 8. Alternatively, an in vitro reaction can be used to assess the activity. Thus, in one embodiment of the invention at least one cytochrome P450 enzyme is selected from the group consisting of polypeptides encoding by the nucleic acid sequence SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20 or a or a functional homologue thereof sharing at least 70%, such as at least 80%, for example at least 90%, such as at least 95%, for example at least 98% sequence identity therewith at the amino acid level.

In a preferred embodiment of the invention the enzyme capable of catalyzing hydroxylation of cucurbitadienol to form 11-hydroxy-cucurbitadienol is CYP5491. Thus, the enzyme catalyzing hydroxylation of cucurbitadienol to form 11-hydroxy-cucurbitadienol may be a polypeptide of SEQ ID NO:44 or a functional homologue thereof sharing at least 70%, such as at least 80%, for example at least 90%, such as at least 95%, for example at least 98% sequence identity therewith.

In one embodiment of the invention this step may be aided by at least one CYP activator. This step of the methods of the invention may thus comprise use of a cytochrome P450 enzyme as described above in combination with at least one CYP activator. Thus, the recombinant host may in addition to containing heterologous nucleic acids encoding the cytochrome P450 enzymes described herein above also contain a heterologous nucleic acid encoding a CYP activator. Said CYP activator may be any useful CYP activator, for example it may be a polypeptide be a polypeptide of SEQ ID NO:46 or a functional homologue thereof sharing at least 70%, such as at least 80%, for example at least 90%, such as at least 95%, for example at least 98% sequence identity therewith.

Step IIIb 24,25 Epoxy Cucurbitadienol→11-Hydroxy-24,25 Epoxy Cucurbitadienol

As described herein above the methods of the invention may comprise a step of producing 11-hydroxy-24,25 epoxy cucurbitadienol from 24,25 epoxy cucurbitadienol using an enzyme capable of catalysing hydroxylation of 24,25 epoxy cucurbitadienol to form 11-hydroxy-24,25 epoxy cucurbitadienol.

The step may be performed in vitro by incubating a composition comprising 24,25 epoxy cucurbitadienol with said enzyme capable of catalyzing hydroxylation of 24,25 epoxy cucurbitadienol to form 11-hydroxy-24,25 epoxy cucurbitadienol.

The step may also be performed in vivo in a recombinant host comprising heterologous nucleic acid(s) encoding an enzyme capable of catalyzing hydroxylation of 24,25 epoxy cucurbitadienol to form 11-hydroxy-24,25 epoxy cucurbitadienol. Said recombinant host may be capable of producing 24,25 epoxy cucurbitadienol, for example because the recombinant host expresses one or more enzymes of the 24,25 epoxy cucurbitadienol biosynthesis pathway, e.g. cucurbitadienol synthase. Alternatively, 24,25 epoxy cucurbitadienol may be provided to said recombinant host for example in the cultivation medium.

Said enzyme capable of catalyzing hydroxylation of cucurbitadienol to form 11-hydroxy-cucurbitadienol preferably is selected from the group of cytochrome P450 enzymes.

In a preferred embodiment of the invention the enzyme capable of catalyzing hydroxylation of 24,25 epoxy cucurbitadienol to form 11-hydroxy-24,25 epoxy cucurbitadienol is CYP5491. Thus, the enzyme catalyzing hydroxylation of 24,25 epoxy cucurbitadienol to form 11-hydroxy-24,25 epoxy cucurbitadienol may be a polypeptide of SEQ ID NO:44 or a functional homologue thereof sharing at least 70%, such as at least 80%, for example at least 90%, such as at least 95%, for example at least 98% sequence identity therewith.

In one embodiment of the invention this step may be aided by at least one CYP activator. This step of the methods of the invention may thus comprise use of a cytochrome P450 enzyme as described above in combination with at least one CYP activator. Thus, the recombinant host may in addition to containing heterologous nucleic acids encoding the cytochrome P450 enzymes described herein above also contain a heterologous nucleic acid encoding a CYP activator. Said CYP activator may be any useful CYP activator, for example it may be a polypeptide be a polypeptide of SEQ ID NO:46 or a functional homologue thereof sharing at least 70%, such as at least 80%, for example at least 90%, such as at least 95%, for example at least 98% sequence identity therewith.

Step IVa—11-Hydroxy-Cucurbitadienol→Mogrol

As described herein above the methods of the invention may comprise a step of producing mogrol from 11-hydroxy-cucurbitadienol using an enzyme or a mixture of enzymes capable of catalysing conversion of 11-hydroxy-cucurbitadienol to form mogrol.

The step may be performed in vitro by incubating a composition comprising 11-hydroxy-cucurbitadienol with said enzyme or mixture of enzymes capable of catalyzing conversion of 11-hydroxy-cucurbitadienol to form mogrol.

The step may also be performed in vivo in a recombinant host comprising heterologous nucleic acid(s) encoding an enzyme or mixture of enzymes capable of catalyzing conversion of 11-hydroxy-cucurbitadienol to form mogrol. Said recombinant host may be capable of producing 11-hydroxy-cucurbitadienol, for example because the recombinant host expresses one or more enzymes of the 11-hydroxy-cucurbitadienol biosynthesis pathway. Alternatively, 11-hydroxy-cucurbitadienol may be provided to said recombinant host for example in the cultivation medium.

Said enzyme or mixture of enzymes capable of catalyzing conversion of 11-hydroxy-cucurbitadienol to form mogrol preferably comprises one or more enzymes with together has CYP450 activity and epoxide hydrolase activity.

Enzymes with CYP450 include for example the polypeptides encoding by the nucleic acid sequence SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20 or a or a functional homologue thereof sharing at least 70%, such as at least 80%, for example at least 90%, such as at least 95%, for example at least 98% sequence identity therewith at the amino acid level.

Another enzyme with CYP450 activity is CYP5491. Thus, the enzyme with CYP450 activity may be a polypeptide of SEQ ID NO:44 or a functional homologue thereof sharing at least 70%, such as at least 80%, for example at least 90%, such as at least 95%, for example at least 98% sequence identity therewith.

In one embodiment of the invention this step may be aided by at least one CYP activator. This step of the methods of the invention may thus comprise use of a cytochrome P450 enzyme as described above in combination with at least one CYP activator. Thus, the recombinant host may in addition to containing heterologous nucleic acids encoding the cytochrome P450 enzymes described herein above also contain a heterologous nucleic acid encoding a CYP activator. Said CYP activator may be any useful CYP activator, for example it may be a polypeptide be a polypeptide of SEQ ID NO:46 or a functional homologue thereof sharing at least 70%, such as at least 80%, for example at least 90%, such as at least 95%, for example at least 98% sequence identity therewith.

The enzyme having epoxide hydrolase activity may for example be an enzyme classified under EC 3.3._._. Said epoxide hydrolase preferably catalyses the following reaction:

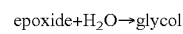

epoxide+$H_2O$→glycol

Examples of enzymes with epoxide hydrolase activity includes S. grosvenorii Epoxide hydrolase 1 and S. grosvenorii Epoxide hydrolase 2. Thus, the enzyme with epoxide hydrolase activity may be selected from the group consisting of polypeptides of SEQ ID NO:38, SEQ ID NO:40 and functional homologue thereof sharing at least 70%, such as at least 80%, for example at least 90%, such as at least 95%, for example at least 98% sequence identity therewith.

Step IVa—11-Hydroxy-24,25 Epoxy Cucurbitadienol-→Mogrol

As described herein above the methods of the invention may comprise a step of producing mogrol from 11-hydroxy-24,25 epoxy cucurbitadienol using an enzyme or a mixture of enzymes capable of catalysing conversion of 11-hydroxy-24,25 epoxy cucurbitadienol to form mogrol.

The step may be performed in vitro by incubating a composition comprising 11-hydroxy-24,25 epoxy cucurbitadienol with said enzyme or mixture of enzymes capable of catalyzing conversion of 11-hydroxy-24,25 epoxy cucurbitadienol to form mogrol.

The step may also be performed in vivo in a recombinant host comprising heterologous nucleic acid(s) encoding an enzyme or mixture of enzymes capable of catalyzing conversion of 11-hydroxy-24,25 epoxy cucurbitadienol to form mogrol. Said recombinant host may be capable of producing 11-hydroxy-24,25 epoxy cucurbitadienol, for example because the recombinant host expresses one or more enzymes of the 11-hydroxy-24,25 epoxy cucurbitadienol biosynthesis pathway. Alternatively, 11-hydroxy-24,25 epoxy cucurbitadienol may be provided to said recombinant host for example in the cultivation medium.

Said enzyme or mixture of enzymes capable of catalyzing conversion of 11-hydroxy-24,25 epoxy cucurbitadienol to form mogrol preferably comprises an enzyme with epoxide hydrolase activity.

The enzyme having epoxide hydrolase activity may for example be an enzyme classified under EC 3.3._._. Said epoxide hydrolase preferably catalyses the following reaction:

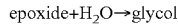

Examples of enzymes with epoxide hydrolase activity includes *S. grosvenorii* Epoxide hydrolase 1 and *S. grosvenorii* Epoxide hydrolase 2. Thus, the enzyme with epoxide hydrolase activity may be selected from the group consisting of polypeptides of SEQ ID NO:38, SEQ ID NO:40 and functional homologue thereof sharing at least 70%, such as at least 80%, for example at least 90%, such as at least 95%, for example at least 98% sequence identity therewith.

Step V—Mogrol→Mogroside

The methods of invention may involve a step of glycosylating mogrol to form mogroside. This step is in general accomplished with the aid of an enzyme or a mixture of enzymes capable of catalyzing glycosylation of mogrol and/or of glycosylated mogrol.

The mogroside may be any of the mogrosides described herein below in the section "Mogrosides".

Step V may be performed in vitro by incubating a composition comprising mogrol with said enzyme or a mixture of enzymes capable of catalyzing glycosylation of mogrol. The step may also be divided into separate steps, wherein each step involves glycosylation of mogrol or glycosylated mogrol.

The step may also be performed in vivo in a recombinant host comprising heterologous nucleic acid(s) encoding an enzyme or a mixture of enzymes capable of catalyzing glycosylation of mogrol and optionally also of glycosylated mogrol. Said recombinant host may be capable of producing mogrol, for example because the recombinant host expresses one or more enzymes of the mogrol biosynthesis pathway. Alternatively, mogrol may be provided to said recombinant host for example in the cultivation medium.

Said enzyme or mixture of enzyme capable of catalyzing glycosylation of mogrol preferably comprises a Uridine-5'-diphospho (UDP) dependent glucosyltransferase (UGT). In particular, it is preferred that step V comprises use of a UGT.

Thus, step V may include incubating mogrol with at least one Uridine-5'-diphospho (UDP) dependent glucosyltransferase (UGT) to produce a mogroside compound (e.g., mogroside I E1, mogroside I A1, mogroside II E, mogroside III A2, mogroside III, mogroside IV, mogroside V, or a mogroside compound glycosylated at C24-OH).

The UGT may for example be selected from the group consisting of 73C3, 73C6, 85C2, 73C5, and 73E1. The UGT may also be UGT73C3 of SEQ ID NO:21, UGT73C6 of SEQ ID NO:23, UGT85C2 of SEQ ID NO:25, UGT73C5 of SEQ ID NO: 22, UGT73E1 of SEQ ID NO:24 or a functional homologue of any of the aforementioned sharing at least 70%, such as at least 80%, for example at least 90%, such as at least 95%, for example at least 98% sequence identity therewith.

The UGT may also be selected from the group consisting of UGT98, UGT1495, UGT1817, UGT5914, UGT8468 and UGT10391. The UGT may also be UGT98 of SEQ ID NO:53, UGT1495 encoded by SEQ ID NO:27, UGT1817 encoded by SEQ ID NO:28, UGT5914 encoded by SEQ ID NO:30, UGT8468 encoded by SEQ ID NO:31 and UGT10391 encoded by SEQ ID NO:32 or a functional homologue of any of the aforementioned sharing at least 70%, such as at least 80%, for example at least 90%, such as at least 95%, for example at least 98% sequence identity therewith at the amino acid level.

When the methods are performed in vitro the UGTs can for example be recombinantly produced or can be in a cell lysate of a recombinant host. This document also features a method of producing a mogroside compound, wherein the method includes contacting mogrol with a cell lysate prepared from a recombinant host expressing a UGT to produce a mogroside compound (e.g., mogroside I E1, mogroside I A1, mogroside II E, mogroside III A2, mogroside III, mogroside IV, mogroside V, or a mogroside compound glycosylated at C24-OH). The UGT can be any of the above mentioned UGTs.

This document provides methods and materials for glycosylating mogrol using one or more Uridine-5'-diphospho (UDP) dependent glucosyltransferases (UGTs). As indicated below, at least five UGTs have been identified that glycosylate the aglycone mogrol. Each of the UGTs identified herein are in glycosyltransferase family I. Thus, in one preferred embodiment the UGT is a UGT in glycosyltransferase family I.

Figure 4:
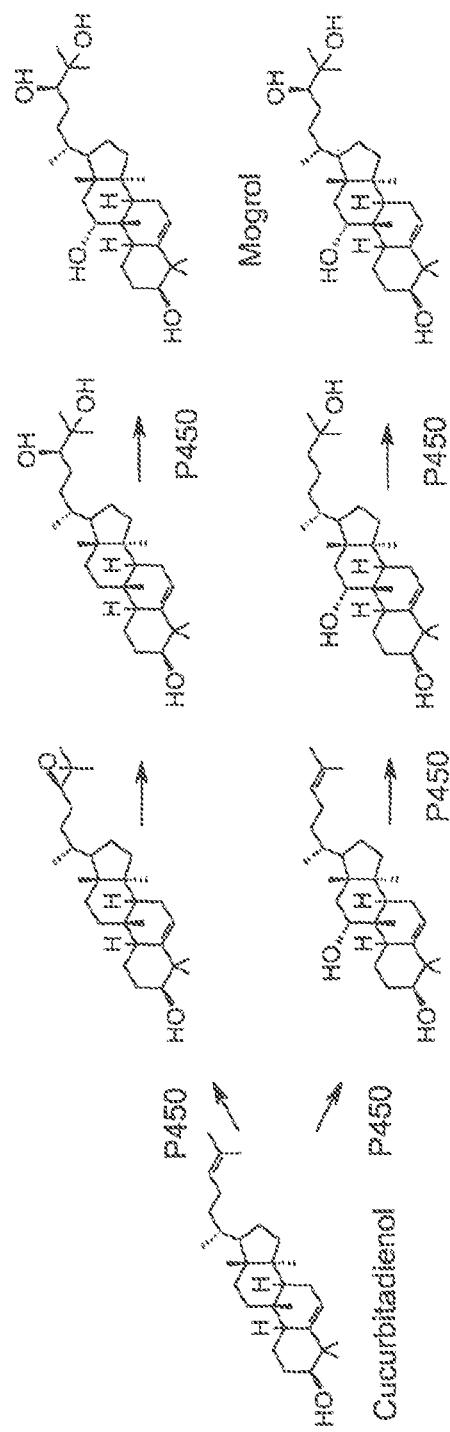
FIG. 4 is a schematic of the pathway proposed herein by the inventors (top) and published (bottom) of a P450 pathway for formation of mogrol from cucurbitadienol.
Figure 5:
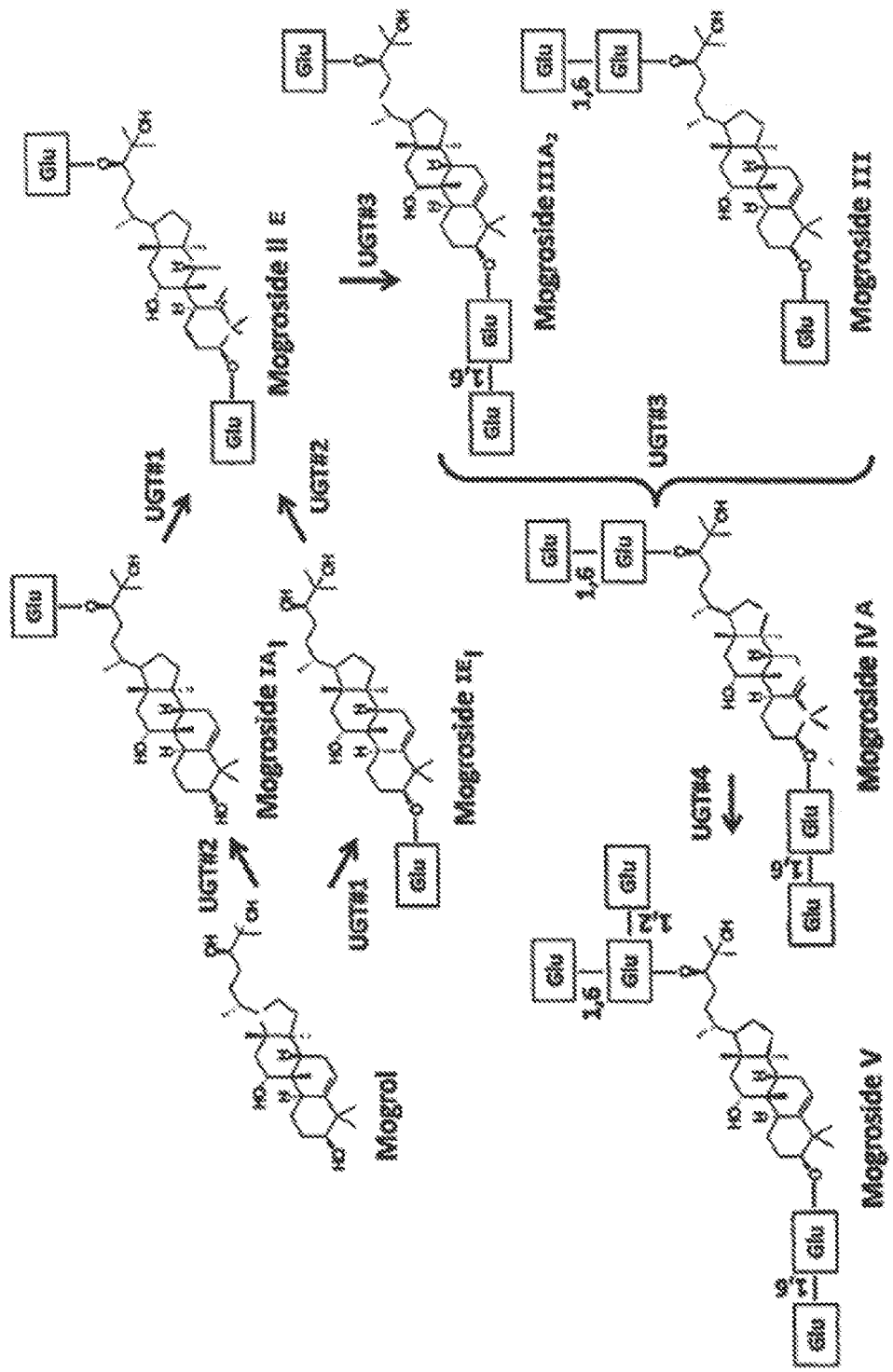
FIG. 5 is a depiction of the biosynthesis of mogroside I E1, mogroside I A1, mogroside II E, mogroside III A2, mogroside III, mogroside IV, and mogroside V from mogrol using UGTs.

UGTs 73C3, 73C6, 85C2 and 73E1 are capable of catalyzing glycosylation at the C24-OH position of mogrol or mogroside (UGT #2 in FIG. 4). Accordingly, in methods of the invention wherein the mogroside to be produced comprises a glycosylation at the O24-OH position then at least one UGT may be UGT73C3 of SEQ ID NO:21, UGT73C6 of SEQ ID NO:23, UGT85C2 of SEQ ID NO:25 or UGT73E1 of SEQ ID NO:24 or a or a functional homologue of any of the aforementioned sharing at least 70%, such as at least 80%, for example at least 90%, such as at least 95%, for example at least 98% sequence identity therewith.

UGT73C5 is capable of catalyzing glycosylation at both the O3-OH of mogrol and mogroside (UGT #1 in FIG. 4) and C24-OH position (UGT #2). Accordingly, in methods of the invention wherein the mogroside to be produced comprises a glycosylation at the C24-OH position and/or a glycosylation at the O3-OH position, then at least one UGT may be UGT73C5 of SEQ ID NO:22 or a functional homologue of any of the aforementioned sharing at least 70%, such as at least 80%, for example at least 90%, such as at least 95%, for example at least 98% sequence identity therewith.

UGTs 73C3, 73C5, and 73C6 are from *Arabidopsis thaliana*. UGT 73E1 and 85C2 are from *Stevia rebaudiana*. The amino acid sequences of UGTs 73C3, 73C5, 73C6, 73E1, and 85C2 are provided herein as SEQ ID NOs: 21-25, respectively). Thus, UGTs 73C3, 73C6, 85C2, or 73E1 can be used to produce mogroside I E1 from mogrol, and UGT73C5 can be used to produce mogroside I A1 from mogrol. Mogroside I E1 can be converted to mogroside II E using UGT73C5. Mogroside I A1 can be converted to mogroside II E using UGTs 73C3, 73C6, 85C2, or 73E1.

In one preferred embodiment of the invention at least one UGT is UGT1576 of SEQ ID NO:48 or a functional homologue of any of the aforementioned sharing at least 70%, such as at least 80%, for example at least 90%, such as at least 95%, for example at least 98% sequence identity therewith. This is in particular the case in embodiments of the invention, wherein the mogroside to be produced comprises a glycosylation at the 24-OH position, because UGT1576 is a glycosyltransferase with mogrol 24-OH UDP-glycosyltransferase activity.

In one preferred embodiment of the invention at least one UGT is UGT98 of SEQ ID NO:53 or a functional homologue thereof sharing at least 70%, such as at least 80%, for example at least 90%, such as at least 95%, for example at least 98% sequence identity therewith. This is in particular the case in embodiments of the invention, wherein the mogroside to be produced comprises a 1,2 glucosylation and a 1,6 glycosylation of the glucose at position C-24 to form mogroside III A1.

In one preferred embodiment of the invention at least one UGT is UGT SK98 of SEQ ID NO:50 or a functional homologue of any of the aforementioned sharing at least 70%, such as at least 80%, for example at least 90%, such as at least 95%, for example at least 98% sequence identity therewith. This is in particular the case in embodiments of the invention, wherein the mogroside to be produced comprise a 1,2 glycosylation of the glucose at position C-24 to form mogroside II A.

As shown in FIG. 4, three enzymatic glycosylations convert mogroside II E into mogroside V or 11-Oxo-mogroside V. First, two glucoses are attached with 1,6-bonds to the two glucose molecules already present in mogroside II E. Second, another glucose is added to the C24-bound glucose, with a 1,2 bond. Mogroside IV is an intermediate in which the 1,2-bound glucose is missing at the C24-bound glucose. In siamenoside this glucose is present, but the 1,6-bound glucose at the C3-bound glucose is missing. 11-Oxo-mogroside V is identical to mogroside V, only the 11-OH is oxidized. One or more of the following UGTs can be used to convert mogroside II E to mogroside IV, mogroside V, 11-oxo-mogroside V, and siamenoside I: UGT98, UGT1495, UGT1817, UGT3494, UGT5914, UGT8468, UGT10391, UGT11789, UGT11999, UGT13679 and UGT15423 (SEQ ID NOs: 26-36, respectively) or functional. For example, one or more of UGT98, UGT1495, UGT1817, UGT5914, UGT8468 and UGT10391 can be used to produce mogroside IV, mogroside V, 11-oxo-mogroside V, or siamenoside I.

In one embodiment of the invention step V comprises one or more of the following steps:
a) Glucosylation of mogrol at C24 to form mogroside I A1
b) 1,6 glucosylation of the C24 bound glucose of mogroside I A1 to form mogroside II A
c) 1,2 glucosylation of the C24 bound glucose of mogroside IIa to form mogroside III A1
d) Glucosylation of mogroside III A1 at the C3 to form siamenoside 1
e) 1,6 glucosylation of the C3 bound glucose of siamenoside 1 to form mogroside V These steps may each be catalyzed by a UGT capable of catalyzing said step. Thus, for example step a) may for example be catalyzed by UGT1576 of SEQ ID NO:48 or a functional homologue of any of the aforementioned sharing at least 70%, such as at least 80%, for example at least 90%, such as at least 95%, for example at least 98% sequence identity therewith. Step b) may for example be catalyzed by UGT98 of SEQ ID NO:53 or a functional homologue thereof sharing at least 70%, such as at least 80%, for example at least 90%, such as at least 95%, for example at least 98% sequence identity therewith. Step c) may for example be catalyzed by UGT98 of SEQ ID NO:53, UGT SK98 of SEQ ID NO:50 or a functional homologue of any of the aforementioned sharing at least 70%, such as at least 80%, for example at least 90%, such as at least 95%, for example at least 98% sequence identity therewith. Step d) may for example be catalyzed by UGT73C5 of SEQ ID NO:22 or a functional homologue thereof sharing at least 70%, such as at least 80%, for example at least 90%, such as at least 95%, for example at least 98% sequence identity therewith. Step e) may for example be catalyzed by UGT of the UGT91 family. For example step e9 may be catalyzed by UGT98 of SEQ ID NO:53 or a functional homologue thereof sharing at least 70%, such as at least 80%, for example at least 90%, such as at least 95%, for example at least 98% sequence identity therewith.

Activity of the UGTs can be assessed in vitro. For example, an in vitro UGT reaction mixture can include UGT enzyme, 4× Tris buffer, substrate (250 μM), UDPglucose (750 μM) and 1% alkaline phosphatase, in a total reaction volume of about 50 μl. The reactions can be performed in sterilized 96 well plates, and incubated overnight at 30° C. After the incubation, 25 μL of DMSO can be added to each reaction and the reaction plates centrifuged for 5 min. Samples can be taken from each well, filtered, and then analyzed via LC-MS.

Production of Polypeptides

As described herein above, the methods of the invention may be performed in in vitro or in vivo. In embodiments of the invention where the methods are performed in vitro one or more of the enzymes to be used in the methods may be prepared using any conventional method for producing polypeptides.

Thus, enzymes, such as synthases, hydrolyases, UGTs and CYP450 polypeptides described herein can be produced using any method. For example, enzymes, such as synthases, hydrolyases, UGT or CYP450 polypeptides can be produced by chemical synthesis. Alternatively, enzymes, such as synthases, hydrolyases, UGT or CYP450 polypeptides described herein can be produced by standard recombinant technology using heterologous expression vectors encoding enzymes, such as synthases, hydrolyases, UGT or CYP450 polypeptides. Expression vectors can be introduced into host cells (e.g., by transformation or transfection) for expression of the encoded polypeptide, which then optionally can be purified or partly purified. Crude extracts comprising the enzymes may also be used with the methods of the invention. Expression systems that can be used for small or large scale production of enzymes, such as synthases, hydrolyases, UGT and CYP450 polypeptides include, without limitation, microorganisms such as bacteria (e.g., *E. coli* and *B. subtilis*) transformed with recombinant DNA, such as bacteriophage DNA, plasmid DNA, or cosmid DNA expression vectors containing the nucleic acid molecules described herein, or yeast (e.g., *S. cerevisiae* or *S. pombe*) transformed with recombinant yeast expression vectors containing the nucleic acid molecules described herein. Useful expression systems also include insect cell systems infected with recombinant virus expression vectors (e.g., baculovirus) containing the nucleic acid molecules described herein, or plant cell systems infected with recombinant virus expression vectors (e.g., tobacco mosaic virus) or transformed with recombinant plasmid expression vectors (e.g., Ti plasmid) containing the nucleic acid molecules described herein. Enzymes, such as synthases, hydrolyases, UGT or CYP450 polypeptides also can be produced using mammalian expression system harboring recombinant expression constructs containing promoters derived from the genome of mammalian cells (e.g., the metallothionein promoter) or from mammalian viruses (e.g., the adenovirus late promoter and the cytomegalovirus promoter), along with the nucleic acids described herein. Enzymes, such as synthases, hydrolyases, UGT or CYP450 polypeptides to be used with the methods of the invention may have an N-terminal or C-terminal tag as discussed below.

This document also provides isolated nucleic acids encoding the enzymes to be used in each of steps Ia, Ib, IIa, IIb, IIIa, IIIb, Iva, IVb and V described herein above, such as synthases, hydrolyases, UGT or CYP450 polypeptides. An "isolated nucleic acid" refers to a nucleic acid that is separated from other nucleic acid molecules that are present in a genome, including nucleic acids that normally flank one or both sides of the nucleic acid in a genome. The term "isolated" as used herein with respect to nucleic acids also includes any non-naturally-occurring nucleic acid sequence, since such non-naturally-occurring sequences are not found in nature and do not have immediately contiguous sequences in a naturally-occurring genome. Thus, the isolated nucleic acid may be cDNA encoding any of the enzymes to be used with the methods of the invention.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., any paramyxovirus, retrovirus, lentivirus, adenovirus, or herpes virus), or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not considered an isolated nucleic acid.

In some embodiments, a nucleic acid sequence encoding an enzyme to be used with the methods of the invention, such as synthases, hydrolyases, UGT or CYP450 polypeptides can include a tag sequence that encodes a "tag" designed to facilitate subsequent manipulation (e.g., to facilitate purification or detection), secretion, or localization of the encoded polypeptide. Tag sequences can be inserted in the nucleic acid sequence encoding the enzyme, such that the encoded tag is located at either the carboxyl or amino terminus of the enzyme. Non-limiting examples of encoded tags include green fluorescent protein (GFP), glutathione S transferase (GST), HIS tag, and Flag™ tag (Kodak, New Haven, Conn.). Other examples of tags include a chloroplast transit peptide, a mitochondrial transit peptide, an amyloplast peptide, signal peptide, or a secretion tag.

Functional Homologs

Functional homologs of the polypeptides described above are also suitable for use in the methods and recombinant hosts described herein. A functional homolog is a polypeptide that has sequence similarity to a reference polypeptide, and that carries out one or more of the biochemical or physiological function(s) of the reference polypeptide. Thus, functional homologues of the enzymes described herein are polypeptides that have sequence similarity to the reference enzyme, and which are capable of catalyzing the same step or part of a step of the methods of the invention as the reference enzyme.

In general it is preferred that functional homologues share at least some degree of sequence identity with the reference polypeptide. Thus, it is preferred that a functional homologues of any of the polypeptides described herein shares at least 70%, such as at least 75%, such as at least 80%, for example at least 85%, such as at least 90%, such as at least 95%, for example at least 98% sequence identity therewith.

Amino acid sequence identity requires identical amino acid sequences between two aligned sequences. Thus, a candidate sequence sharing 80% amino acid identity with a reference sequence, requires that, following alignment, 80% of the amino acids in the candidate sequence are identical to the corresponding amino acids in the reference sequence. Identity according to the present invention is determined by aid of computer analysis, such as, without limitations, the ClustalW computer alignment program (Higgins D., Thompson J., Gibson T., Thompson J. D., Higgins D. G., Gibson T. J., 1994. CLUSTAL W: improving the sensitivity of progressive multiple sequence alignment through sequence weighting, position-specific gap penalties and weight matrix choice. Nucleic Acids Res. 22:4673-4680), and the default parameters suggested therein. The ClustalW software is available as a ClustalW WWW Service at the European Bioinformatics Institute. Using this program with its default settings, the mature (bioactive) part of a query and a reference polypeptide are aligned. The number of fully conserved residues are counted and divided by the length of the reference polypeptide. The sequence identity is determined over the entire length of the reference polypeptide.

A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for a polypeptide, or by combining domains from the coding sequences for different naturally-occurring polypeptides ("domain swapping"). Techniques for modifying genes encoding functional homologues of an enzyme to be used with the methods of the invention, such as synthases, hydrolyases, UGT or CYP450 polypeptides described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide:polypeptide interactions in a desired manner. Such modified polypeptides are considered functional homologs. The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of enzymes to be used with the methods of the invention, such as synthases, hydrolyases, UGT or CYP450 polypeptides. Sequence analysis can involve BLAST, Reciprocal BLAST, or PSI-BLAST analysis of nonredundant databases using one of the sequences identified herein encoding an enzyme to be used with the methods of the invention, such as synthases, hydrolyases, UGT amino acid sequence as the reference sequence. Amino acid sequence is, in some instances, deduced from the nucleotide sequence. Those polypeptides in the database that have greater than 40% sequence identity are candidates for further evaluation for suitability as synthases, hydrolyases, UGT or CYP450 polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in enzymes to be used with the methods of the invention, such as synthases, hydrolyases, UGT or CYP450 polypeptides, e.g., conserved functional domains. Conserved regions can be identified by locating a region within the primary amino acid sequence of a polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/ and pfam.janelia.org/. The information included at the Pfam database is described in Sonnhammer et al., Nucl. Acids Res., 26:320-322 (1998); Sonnhammer et al., Proteins, 28:405-420 (1997); and Bateman et al., Nucl. Acids Res., 27:260-262 (1999). Conserved regions also can be determined by aligning sequences of the same or related polypeptides from closely related species. Closely related species preferably are from the same family. In some embodiments, alignment of sequences from two different species is adequate. Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity. Sequence identity can be determined as set forth above.

Mogrosides

The present invention relates to methods for producing mogrosides and materials for use in such methods. The term "mogroside" as used herein refers to mogrol glycosylated at one or more positions. In particular, mogrosides according to the present invention may be mogrol glycosylated with one or more glucose residues at the positions 3 and/or 24. It is less preferred that mogrosides are glycosylated at the 11 and 25 positions. Mogrol is a compound of formula I provided below, wherein both $R_1$ and $R_2$ are —H.

It is preferred that the mogroside is a compound of the following formula I:

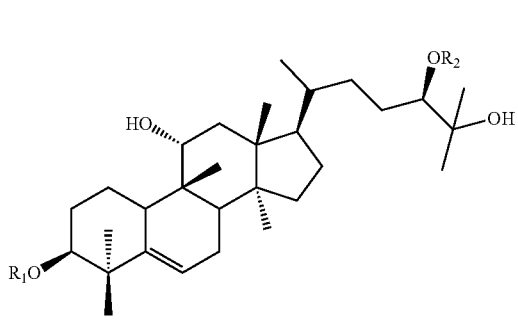

(I)

wherein $R_1$ and $R_2$ independently are —H, mono-glucoside, di-glucoside, tri-glucoside, and at least one of $R_1$ and $R_2$ is not —H.

In particular the mogroside may be one the mogrosides described in Table 1 herein below.

TABLE 1

Mogrosides of formula I

| Name | $R_1$ | $R_2$ |
|---|---|---|
| mogroside V | Glc6-Glc- | Glc6-Glc2-Glc |
| siamenoside I | Glc- | Glc6-Glc2-Glc- |
| mogroside IV | Glc6-Glc- | Glc2-Glc- |
| mogroside IV A | Glc6-Glc- | Glc6-Glc- |
| mogroside III | Glc- | Glc6-Glc- |
| mogroside III A1 | H | Glc6-Glc2-Glc- |
| mogroside III A2 | Glc6-Glc- | Glc- |
| mogroside III E | Glc- | Glc2-Glc- |
| mogroside II A | H | Glc2-Glc- |
| mogroside II A1 | H | Glc6-Glc- |
| mogroside II A2 | Glc6-Glc- | H |
| mogroside II E | Glc- | Glc- |
| mogroside I A1 | H | Glc- |
| mogroside I E1 | Glc- | H |

Glc = glucose

Mogroside I A1 may sometimes be referred to as mogroside Ib. Mogroside I E1 may sometimes be referred to as mogroside Ia. Mogroside II E may sometimes be referred to as mogroside II. Mogroside III A2 may sometimes be referred to as mogroside IIIa.

Mogroside III may sometimes be referred to as mogroside IIIb. This alternative nomenclature is for example used in U.S. Ser. No. 61/733,220.

The invention will be further described in the following examples, which do not limit the scope of the invention described in the claims.

SEQUENCE LISTING

SEQ ID NO: 1    Amino acid sequence of *C. pepo* cucurbitadienol synthase
SEQ ID NO: 2    Amino acid sequence of C-terminal portion of *Siraitia grosvenorii* cucurbitadienol synthase
SEQ ID NO: 3    DNA sequence encoding CYP533 (nucleotide sequence of CYP533 gene)
SEQ ID NO: 4    DNA sequence encoding CYP937 (nucleotide sequence of CYP937 gene)
SEQ ID NO: 5    DNA sequence encoding CYP1798 (nucleotide sequence of CYP1798 gene)
SEQ ID NO: 6    DNA sequence encoding CYP1994 (nucleotide sequence of CYP1994 gene)
SEQ ID NO: 7    DNA sequence encoding CYP2048 (nucleotide sequence of CYP2048 gene)
SEQ ID NO: 8    DNA sequence encoding CYP2740 (nucleotide sequence of CYP2740 gene)
SEQ ID NO: 9    DNA sequence encoding CYP3404 (nucleotide sequence of CYP3404 gene)
SEQ ID NO: 10   DNA sequence encoding CYP3968 (nucleotide sequence of CYP3968 gene)
SEQ ID NO: 11   DNA sequence encoding CYP4112 (nucleotide sequence of CYP4112 gene)
SEQ ID NO: 12   DNA sequence encoding CYP4149 (nucleotide sequence of CYP4149 gene)
SEQ ID NO: 13   DNA sequence encoding CYP4491 (nucleotide sequence of CYP4491 gene)
SEQ ID NO: 14   DNA sequence encoding CYP5491 (nucleotide sequence of CYP5491 gene)
SEQ ID NO: 15   DNA sequence encoding CYP6479 (nucleotide sequence of CYP6479 gene)
SEQ ID NO: 16   DNA sequence encoding CYP7604 (nucleotide sequence of CYP7604 gene)
SEQ ID NO: 17   DNA sequence encoding CYP8224 (nucleotide sequence of CYP8224 gene)
SEQ ID NO: 18   DNA sequence encoding CYP8728 (nucleotide sequence of CYP8728 gene)
SEQ ID NO: 19   DNA sequence encoding CYP10020 (nucleotide sequence of CYP10020 gene)

| | |
|---|---|
| SEQ ID NO: 20 | DNA sequence encoding CYP10285 (nucleotide sequence of CYP10285 gene) |
| SEQ ID NO: 21 | Amino acid sequence of UGT73C3 |
| SEQ ID NO: 22 | Amino acid sequence of UGT73C5 |
| SEQ ID NO: 23 | Amino acid sequence of UGT73C6 |
| SEQ ID NO: 24 | Amino acid sequence of UGT73E1 |
| SEQ ID NO: 25 | Amino acid sequence of UGT85C2 |
| SEQ ID NO: 26 | Nucleotide sequence encoding *Siraitia grosvenorii* UGT98 |
| SEQ ID NO: 27 | Nucleotide sequence encoding *Siraitia grosvenorii* UGT1495 |
| SEQ ID NO: 28 | Nucleotide sequence encoding *Siraitia grosvenorii* UGT1817 |
| SEQ ID NO: 29 | Partial gene sequence - nucleotide sequence encoding fragment of *Siraitia grosvenorii* UGT3494 |
| SEQ ID NO: 30 | Nucleotide sequence encoding *Siraitia grosvenorii* UGT5914 |
| SEQ ID NO: 31 | Nucleotide sequence encoding *Siraitia grosvenorii* UGT8468 |
| SEQ ID NO: 32 | Nucleotide sequence encoding *Siraitia grosvenorii* UGT10391 |
| SEQ ID NO: 33 | Partial gene sequence - nucleotide sequence encoding fragment of *Siraitia grosvenorii* UGT11789 |
| SEQ ID NO: 34 | Partial gene sequence - nucleotide sequence encoding fragment of *Siraitia grosvenorii* UGT11999 |
| SEQ ID NO: 35 | Partial gene sequence - Nucleotide sequence encoding fragment of *Siraitia grosvenorii* UGT13679 |
| SEQ ID NO: 36 | Partial gene sequence - Nucleotide sequence encoding fragment of *Siraitia grosvenorii* UGT15423 |
| SEQ ID NO: 37 | DNA sequence encoding *S. grosvenorii* Epoxide hydrolase 1 codon optimised for expression in *S. cerevisiae* |
| SEQ ID NO: 38 | Amino acid sequence of *S. grosvenorii* Epoxide hydrolase 1 |
| SEQ ID NO: 39 | DNA sequence encoding *S. grosvenorii* Epoxide hydrolase 2 codon optimised for expression in *S. cerevisiae* |
| SEQ ID NO: 40 | Amino acid sequence of *S. grosvenorii* Epoxide hydrolase 2 |
| SEQ ID NO: 41 | DNA sequence encoding CYP10969 (nucleotide sequence of CYP10969 gene) |
| SEQ ID NO: 42 | DNA sequence encoding *Siraitia grosvenorii* cucurbitadienol synthase codon optimized for expression in *S. cerevisiae* |
| SEQ ID NO: 43 | Amino acid sequence of *Siraitia grosvenorii* cucurbitadienol synthase |
| SEQ ID NO: 44 | Amino acid sequence of *S. grosvenorii* CYP5491 |
| SEQ ID NO: 45 | DNA sequence encoding *S. grosvenorii* CPR4497 |
| SEQ ID NO: 46 | Amino acid sequence of *S. grosvenorii* CPR4497 |
| SEQ ID NO: 47 | DNA sequence encoding *S. grosvenorii* UGT1576 |
| SEQ ID NO: 48 | Amino acid sequence of *S. grosvenorii* UGT1576 |
| SEQ ID NO: 49 | DNA sequence encoding *S. grosvenorii* UGT SK98 |
| SEQ ID NO: 50 | Amino acid sequence of *S. grosvenorii* UGT SK98 |
| SEQ ID NO: 51 | DNA sequence encoding *S. grosvenorii* UGT98 |
| SEQ ID NO: 52 | DNA sequence encoding *S. grosvenorii* UGT98 codon optimised for expression in *S. cerevisiae* |
| SEQ ID NO: 53 | Amino acid sequence of *S. grosvenorii* UGT98 |
| SEQ ID NO: 54 | Amino acid sequence of *S. cerevisiae* squalene epoxidase encoded by the ERG1 gene |
| SEQ ID NO: 55 | Amino acid sequence of *S. cerevisiae* lanosterol synthase encoded by the ERG7 gene |

EXAMPLES

Example 1—Purification of Mogroside V

Mogroside V was purified from commercially available monk fruit extracts (PureLo®, Swanson) as follows. Three bottles of PureLo® (240 grams) were dissolved in water (900 mL), then loaded on a column of HP-20 resin (400 gram resin). The column was washed with water (2.5 liters); then further washed with 20% methanol-water. The product was eluted with methanol. After evaporation of solvents and drying under high vacuum, mogroside V (2.5 grams, ~80% purity, 11-oxomogroside V was the major impurity) was obtained.

Example 2—Enzymatic Synthesis of Mogrol from Mogroside V

Figure 6:
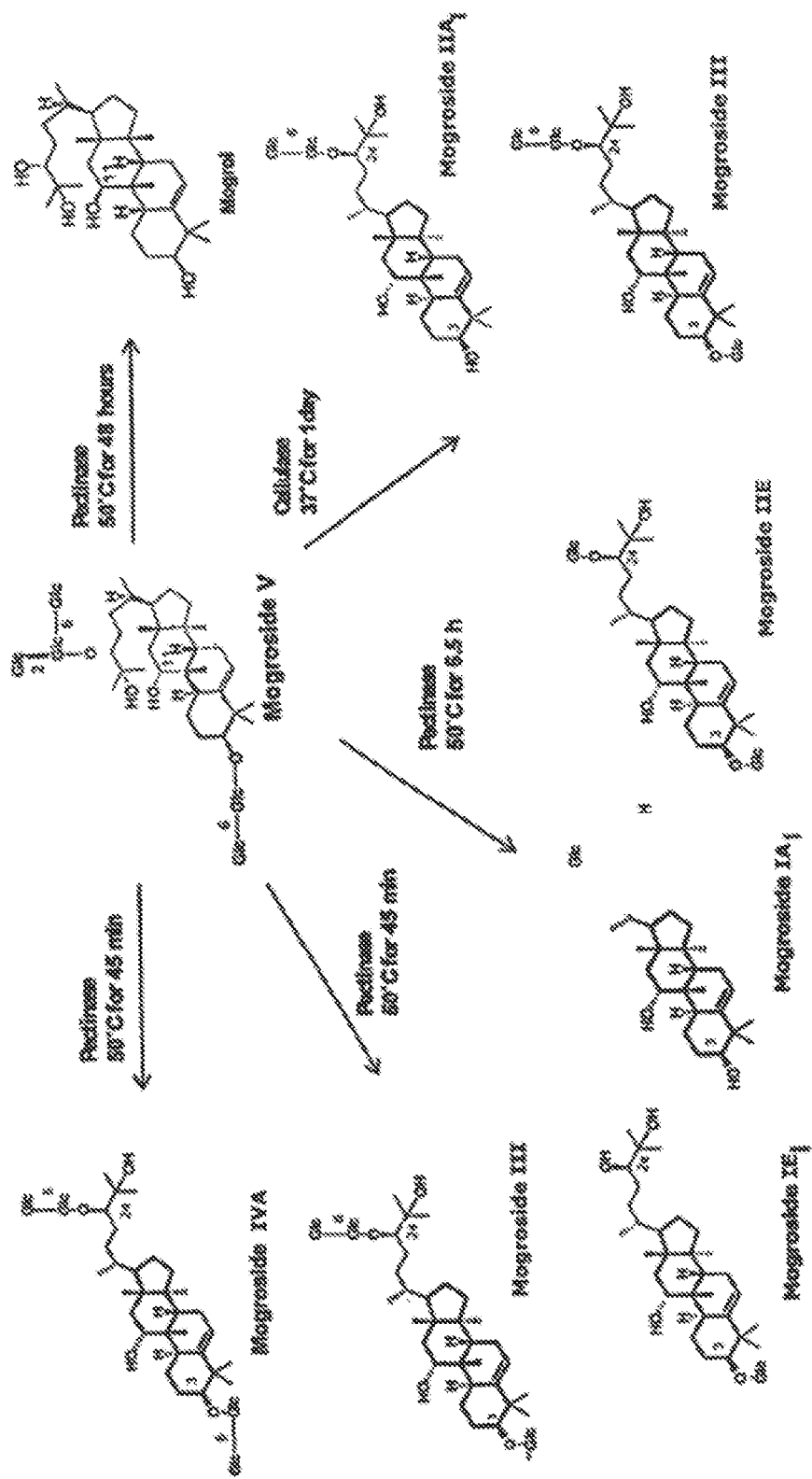
FIG. 6 is a schematic of the products obtained from mogroside V after incubation with a pectinase and/or a cellulase.

Mogroside V (300 mg) was dissolved in 0.1M sodium acetate buffer (pH 4.5, 100 mL), and crude pectinase from *Aspergillus niger* (25 mL, Sigma P2736) was added. The mixture was stirred at 50° C. for 48 hours. The reaction mixture was extracted with ethyl acetate (2×100 ml). The organic extract was dried under vacuum then purified with preparative HPLC. Pure mogrol (40 mg) was obtained and its structure confirmed by NMR and mass spectroscopy. See FIG. 6.

Example 3—Enzymatic Synthesis of Mogrol 3-O-glucoside (mogroside I E1) and Mogrol 24-O-glucoside (Mogroside I A1) from Mogroside V Mogroside V (300 mg) was dissolved in 0.1M sodium acetate buffer (pH 4.5, 100 ml), and crude pectinase from *Aspergillus niger* (25 ml, Sigma P2736) was added. The mixture was stirred at 50° C. for 6.5 hours. The reaction mixture was extracted with ethyl acetate (2×100 ml). The organic extract was dried under vacuum then purified with preparative HPLC. Pure mogroside I E1 (11.0 mg) and mogroside I A1 (8.0 mg) were obtained. Their structures were confirmed by NMR and mass spectroscopy. See FIG. 6.

Example 4—In Vitro UGT Screening and Reactions

In vitro reactions of mogrol with a panel of 230 UGT enzymes were performed and the products were analyzed with LC-MS. The in vitro UGT reaction mixtures included 4× Tris buffer, mogrol (250 μM), UDP-glucose (750 μM) and 1% alkaline phosphatase. Five μl of each partially purified UGT enzyme or crude enzyme extract was added to the reaction, and the reaction volume brought to 50 μl with water. The reactions were incubated overnight at 30° C. and performed in sterilized 96 well plates. After the incubation, 25 μL of DMSO were added into each reaction and the reaction plates were centrifuged for 5 min. Forty μL samples were taken from each well and filtered, and were used for LC-MS analysis. UGTs 73C3, 73C6 and 85C2 were found to convert all the mogrol substrate to mogroside I A1. UGT 73C5 makes both mogroside I E1 and I A1. In the reaction with UGT 20 73E1, although the reaction was not complete, mogroside I A1 was found as the major product, together with a new glycosylated mogrol (neither mogroside I E1 nor I A1; exact mass shown as a mogroside I, presumably caused by a glycosylation event on C11-OH).

Example 5 Identifying the Monk Fruit Cucurbitadienol Synthase

The gene in monk fruit that codes for cucurbitadienol synthase is CirCS, and the partial gene sequence covering 338 of the supposedly 764 amino acids was identified by doing a tBLASTn analysis of the assembled data with a query cucurbitadienol synthase from *Cucurbita pepo* (accession number BAD34645.1, SEQ ID NO:1). The partial CirCS is 97.5% identical to the *C. pepo* gene at the protein level (SEQ ID NO:2; from residues 515 to 764 of SEQ ID NO:1).

Figure 10A:
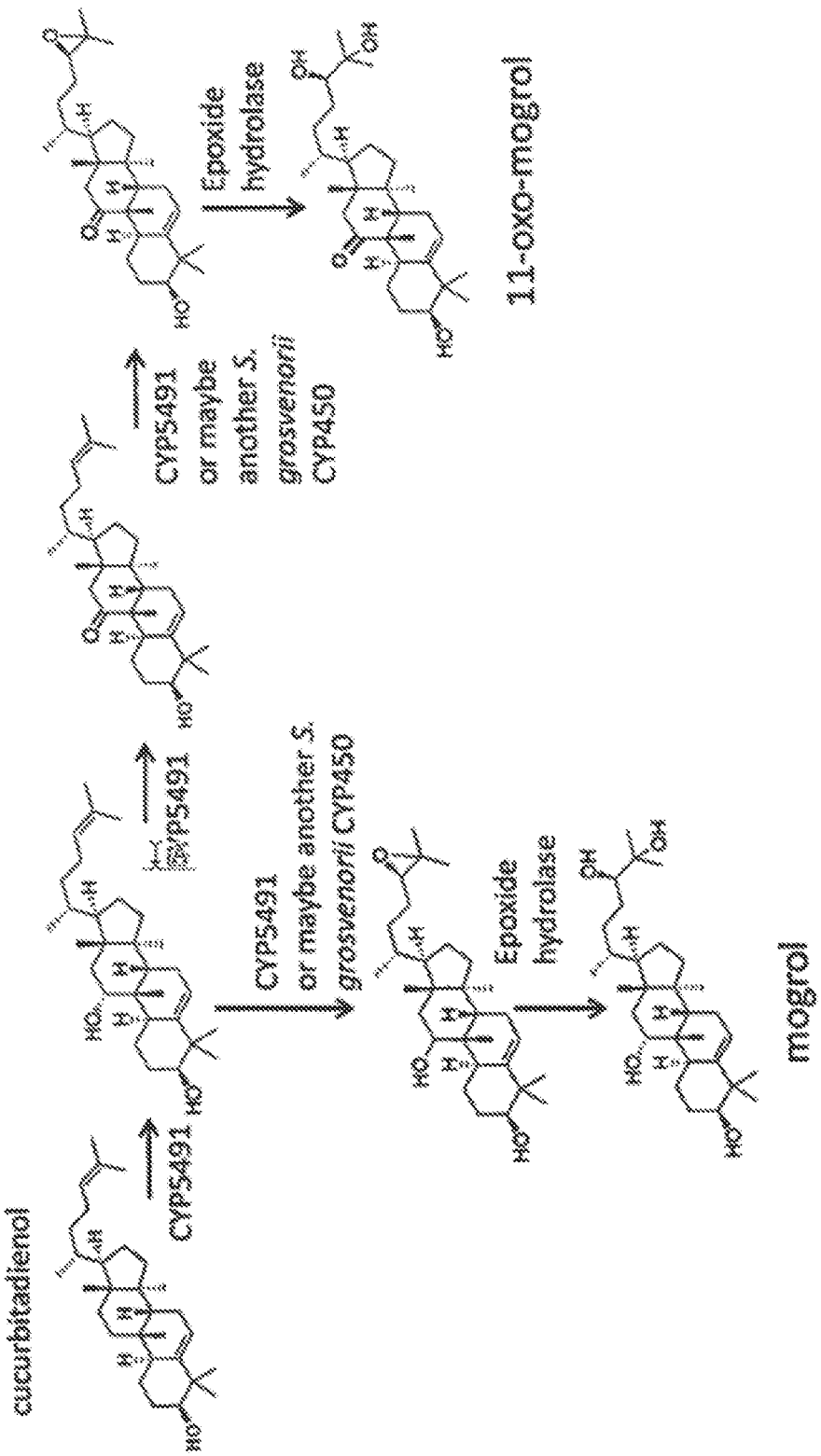
FIG. 10A shows a route from oxido-squalene to mogrol and 11-oxo-mogrol proposed by the present invention.
Figure 10B:
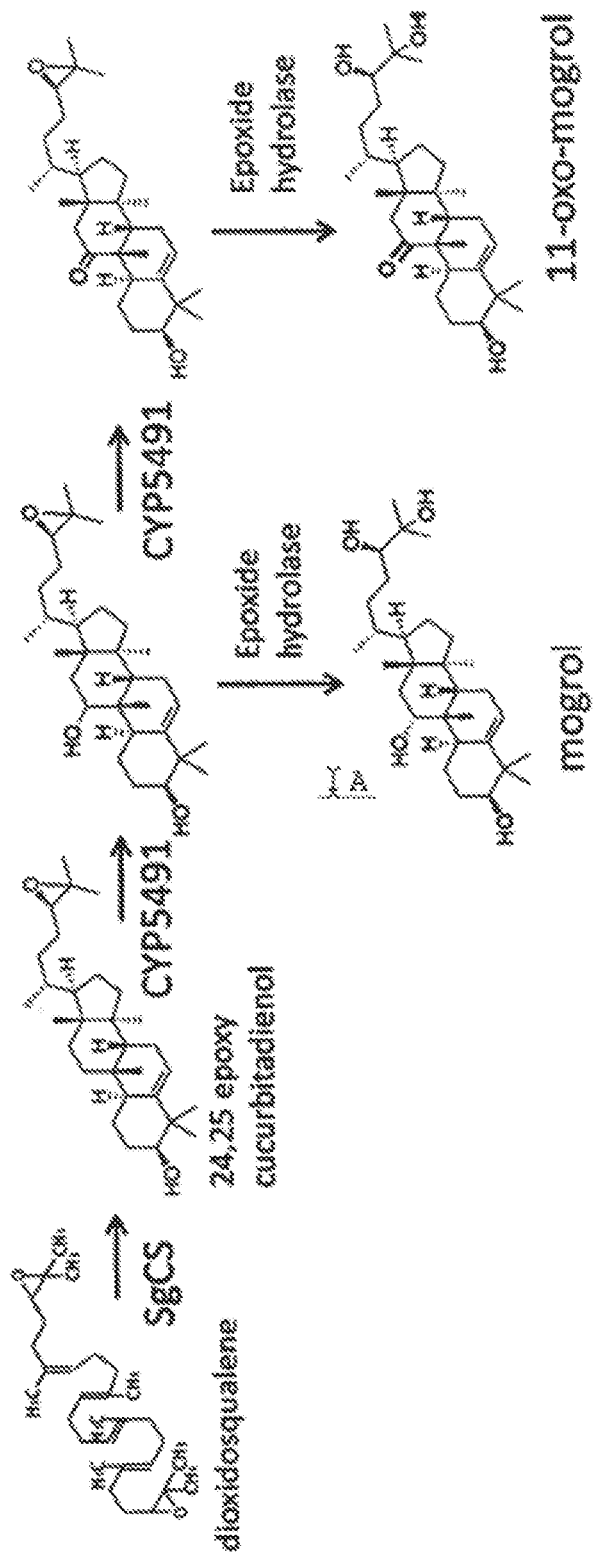
FIG. 10B shows a route from dioxido-squalene to mogrol and 11-oxo-mogrol proposed by the present invention.

Example 6 Identifying Monk Fruit Candidate Genes for P450 Enzymes Catalyzing Formation of Mogrol from Cucurbitadienol A pathway from cucurbitadienol to mogrol has been proposed by Tang et al., *BMC Genomics,* 12, 343 (2011). The intermediates cucurbitadienol and mogrol exist in the fruit as they have been isolated as minor products. See Ukiya, et al., *J. Agric. Food Chem.* 50, 6710-6715 (2002). Glycoside intermediates exist in both 11-hydroxy and 11-oxo series, and gradually change from mogroside I to mogroside V as fruits ripen, which indicates that the triterpene core is fully oxidized by P450 enzymes before the subsequent glycosylations. According to the scheme proposed by Tang et al., three independent cytochrome P450 enzyme-catalyzed oxidations results in mogrol formation from cucurbitadienol (lower route in FIG. 4). The present inventors have found that the proposed primary reaction is highly unlikely. It is therefore submitted that the route may involve epoxidation by one cytochrome P450 enzyme, followed by a spontaneous or enzyme catalyzed hydration, and another P450 enzyme-catalyzed oxidation (visualized in the upper route in FIG. 4), or the route may comprise similar steps in another order as shown in FIG. 10A. The present inventors also propose another route starting from dioxidosqualene, which is shown in FIG. 10B.

To identify the most likely candidate P450 genes from monk fruit, a BLAST database was made consisting of the polypeptide sequences of the 239 public domain *Arabidopsis thaliana* cytochrome P450 enzymes, representing most known enzyme subfamilies and variations. The sequences were used in a tBLASTn (translated nucleotide database) analysis of the assembled monk fruit transcriptome data to identify all sequences with a homology to any of the database query sequences with an E value of 10E-10 or lower. Seventy-two sequences were identified. Typically, the ability to assemble full or long gene lengths of expressed sequence tags in a transcriptome study means that many sequence tags of the gene in question were present. In the current experiment, this indicates that the gene was highly expressed in the monk fruit tissue and thus has a high probability of being a candidate for one of the two P450 enzymes of interest. Of the 72 sequences, 18 were full length or almost full length. The assembled genes were designated CYP533, CYP937, CYP1798, CYP1994, CYP2048, CYP2740, CYP3404, CYP3968, CYP4112, CYP4149, CYP4491, CYP5491, CYP6479, CYP7604, CYP8224, CYP8728, CYP10020, and CYP10285.

These are candidate genes for two P450 enzymes involved in catalyzing conversion of cucurbitadienol into mogrol. Full length gene sequences were amplified by PCR for the gene contigs CYP533, CYP937, CYP1798, CYP1994, CYP2740, CYP4112, CYP4149, CYP4491, CYP5491, CYP7604, CYP8224, and CYP10285, using monk fruit leaf genomic DNA or root cDNA and sequence overlap extension technology to remove resident intron sequences. The nucleotide sequences of CYP533, CYP937, CYP1798, CYP1994, CYP2048, CYP2740, CYP3404, CYP3968, CYP4112, CYP4149, CYP4491, CYP5491, CYP6479, CYP7604, CYP8224, CYP8728, CYP10020, and CYP10285 are provided as SEQ ID NOs: 3-20, respectively.

Figure 1:
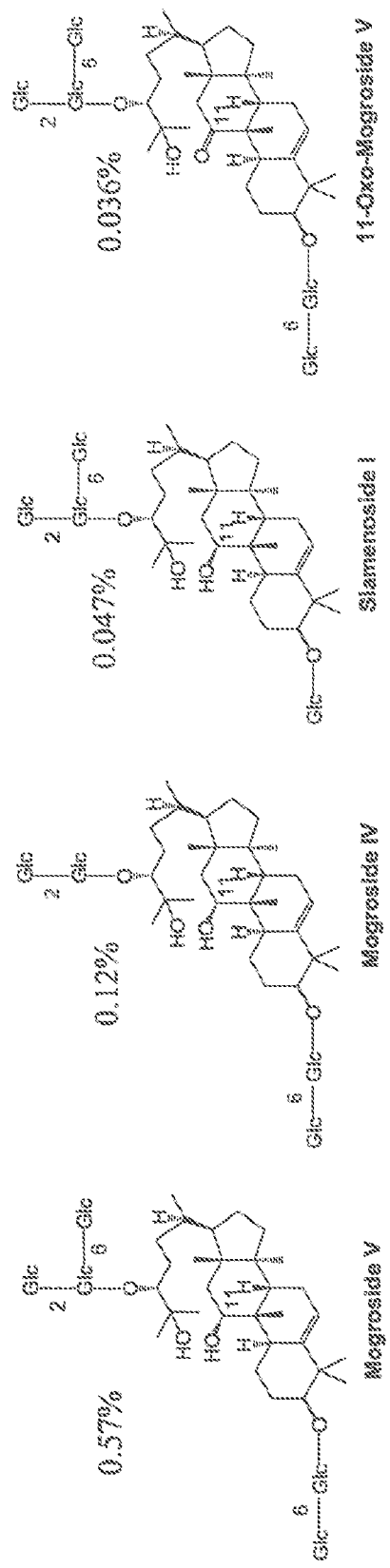
FIG. 1 contains the chemical structure of Mogroside V, Mogroside IV, Siamenoside I, and 11-Oxomogroside V.

Example 7—Identifying Monk Fruit Candidate Genes for Glycosyltransferase Enzymes Catalyzing Formation of Mogroside V, 11-Oxo-Mogroside V, Mogroside IV, Mogrosides III A2 and b and Siamenoside from Mogroside II E Three enzymatic glycosylations are needed to convert mogroside II E into mogroside V or 11-Oxo-mogroside V. Two glucoses are attached with 1,6-bonds to the two glucose molecules already present in mogroside II E. This may be done by one UGT enzyme. Another glucose is added to the C24-bound glucose, with a 1,2 bond. Mogroside IV is an intermediate in which the 1,6-bound glucose is missing at the C24-bound glucose. In siamenoside this glucose is present, but the 1,6-bound glucose at the C3-bound glucose is missing. 11-Oxo-mogroside V is identical to mogroside V, only the 11-OH is oxidized. See, FIG. 1 for the structures of mogroside IV, mogroside V, 11-Oxo-mogroside V, and siamenoside.

To identify all possible UGT genes in the assembled monk fruit transcriptome data, a database was assembled consisting of the polypeptide sequences of glycosyltransferases (UGTs) of all known sub-families, a total of 160 sequences. A tBLASTn analysis was performed between this database and the assembled monk fruit data. UGTs performing di-glycosylation (i.e., attaching a sugar to another sugar which in turn resides on an aglycon) invariably come from Family 1 UGT sub-families 76, 79, 91 or 94 (with the latter three forming the "orthology group 8"). While sub-family 76 enzymes usually make 1,3 bonds, orthology group 8 UGTs always make 1,2 or 1,6 bonds.

Sequences were identified that showed more homology to orthology group 8 enzymes than to any other UGT enzymes or any non-UGT genes. Thus 11 contigs were identified as likely candidates to encode the two glycosyltransferase genes needed to turn mogroside II E into mogroside V: UGT98, UGT1495, UGT1817, UGT3494, UGT5914, UGT8468, UGT10391, UGT11789, UGT11999, UGT13679 and UGT15423 (SEQ ID NOs: 26-36, respectively). Of these we were able to amplify by PCR UGT98, UGT1495, UGT1817, UGT5914, UGT8468 and UGT10391, using monk fruit leaf genomic DNA or root cDNA. The amplified genes were inserted into *E. coli* expression plasmid vectors.

The enzymes are expressed and purified on nickel columns. In vitro reactions of mogroside I A1, I E1 and II E with the panel of 6 purified UGT enzymes are performed and the products analyzed with LC-MS. The in vitro UGT reaction mixtures include 4× Tris buffer, substrate (250 µM), UDP-glucose (750 µM) and 1% alkaline phosphatase.

Five µl of each partially purified UGT enzyme are added to the reaction, and the reaction volume brought to 50 µl with water. The reactions are incubated overnight at 30° C. and performed in sterilized 96 well plates. After the incubation, 25 µL of DMSO are added into each reaction and the reaction plates are centrifuged for 5 min. Forty µL samples are taken from each well and filtered, and then analyzed via LC-MS. The UGT catalyzing the 1,6-bond formation as well as the enzyme catalyzing the 1,2-bond formation are identified based on the LC-MS analysis.

Example 8 Using eYAC Technology to Identify the Cytochrome P450 Enzymes Responsible for Turning Cucurbitadienol into Mogrol eYAC gene expression technology was used to identify the active cytochrome P450 enzymes within a collection of candidate genes. The following genes were inserted into "Entry vectors" (a collection of plasmid vectors containing gene promoter and terminator sequences which have different nucleotide sequence but which are all 30 repressible by the addition of the amino acid methionine): the *Cucurbita pepo* cucurbitadienol synthase gene, CYP533 (SEQ ID NO:3), CYP937 (SEQ ID NO:4), CYP1798 (SEQ ID NO:5), CYP1994 (SEQ ID NO:6), CYP2740 (SEQ ID NO:8), CYP4112 (SEQ ID NO:11), CYP4149 (SEQ ID NO:12), CYP4491 (SEQ ID NO:13), CYP5491 (SEQ ID NO:14), CYP7604 (SEQ ID NO:16), CYP8224 (SEQ ID NO:17), and CYP10285 (SEQ ID NO:20), the two cytochrome P450 oxidoreductase (CPR) genes from *Arabidopsis thaliana* (ATR1 and ATR2), a CPR from *Stevia rebaudiana* (CPR8), a CPR isolated from monk fruit, and the glycosyltransferases UGT73C5 (SEQ ID NO: 22) and UGT73C6 (SEQ ID NO:23) from *A. thaliana* and UGT85C2 (SEQ ID NO:25) from *S. rebaudiana*.

The expression cassettes from these 17 plasmids are excised after an AscI+SrfI digestion, purified and then randomly concatenated in ligation reactions to create artificial yeast chromosomes ("eYACs"). From 30 to 200 ug of DNA are prepared from 10 each of the cassette-containing entry vectors and the cassettes are randomly concatenated into eYACs by ligation with T4 ligase in a 3 hour reaction. The success of the concatenation reaction is assessed by the viscosity of the reaction mixture, since concatenated DNA is highly viscous. DNA fragments ("arms") containing a centromere, two telomeres and the LEU2 and TRP1 selection markers are added to the end of the 15 concatenated expression cassettes, thereby creating functional eYACs. The eYACs are transformed into transformation-competent spheroplasts of yeast strain erg7 by zymolyase digestion of the yeast cell wall, followed by treatment with a $CaCl_2$)/PEG buffer, making the spheroplasts permeable to large molecules such as eYACs. After transformation, the yeast spheroplasts are embedded in a "noble agar" based solid growth medium, in which regeneration of the cell wall can take place. Colonies appear from 4-8 days after inoculation. The regeneration medium lacks the amino acids leucine and tryptophan, thus selecting for the presence of double-armed eYACs in the yeast cells. One hundred transformants are selected and analyzed for production of mogrosides I E1, I A1 and II E, LC-MS (Liquid Chromatography-coupled Mass Spectrometry (Triple Quadropole)).

Each transformant is re-streaked and tested for yeast strain markers and the genetic presence of both arms of the eYAC, i.e., the LEU2 and TRP1 markers. More than 95% of the transformants has the correct genotype. Each transformant is given a CEY designation number. Initially, 48 CEYs are grown in 50 ml of Synthetic Complete medium (SC) in 100 ml Ehrlenmeyer flasks, without methionine, so as to induce gene expression from the eYACs, and without tryptophan, leucine and histidine, so as to counter-select for loss of eYACs. The cultures have a start density corresponding to an OD600 of 0.25, and they are inoculated for 48 h at 30 C, with slow shaking (150 rpm). After 24 hours, 1 ml supernatant from each culture is collected and subjected to LC-MS analysis. Positive CEYs (i.e., those producing any of the mogrosides assayed for) are subjected to PCR analysis in order to assess which CYP genes are present on the harbored eYAC and thus identifying the mogrol pathway P450 enzymes.

Example 9

Boosting Mogrol Pathway Precursor Availability

The background strain used in this study is the BY4742 strain deleted for the TRP1 gene. This strain is called EFSC301. To increase the availability of oxidosqualene and dioxidosqualene in this laboratory yeast strain, the promoter of the endogenous ERG7 gene was displaced by a PCR fragment consisting of the Nurseothricin marker (NatMX) and the CUP1 cupper inducible promoter. This displacement gives low transcription and thereby low expression of ERG7 when the yeast strain is grown in normal growth medium like Synthetic Complete medium (SC medium). ERG7 encode the lanosterol synthase and lowered expression is known to result in accumulation of oxidosqualene and dioxidosqualene in baker's yeast. Oxidosqualene is generally the precursor of triterpenoids and possibly a precursor of the mogrol pathway. To further increase oxidosqualene and dioxidosqualene availability the squalene epoxidase encoded by ERG1 was overexpressed by a GPD1 promoter from a gene copy integrated into the genome. The sequence of the squalene epoxidase encoded by ERG1 is provided herein as SEQ ID NO:54. Furthermore a truncated copy of the yeast HMG reductase (tHMG1) was expressed from a genomically integrated gene copy, with expression from a GPD1 promoter. The resulting strain is called EFSC3027.

Figure 7:
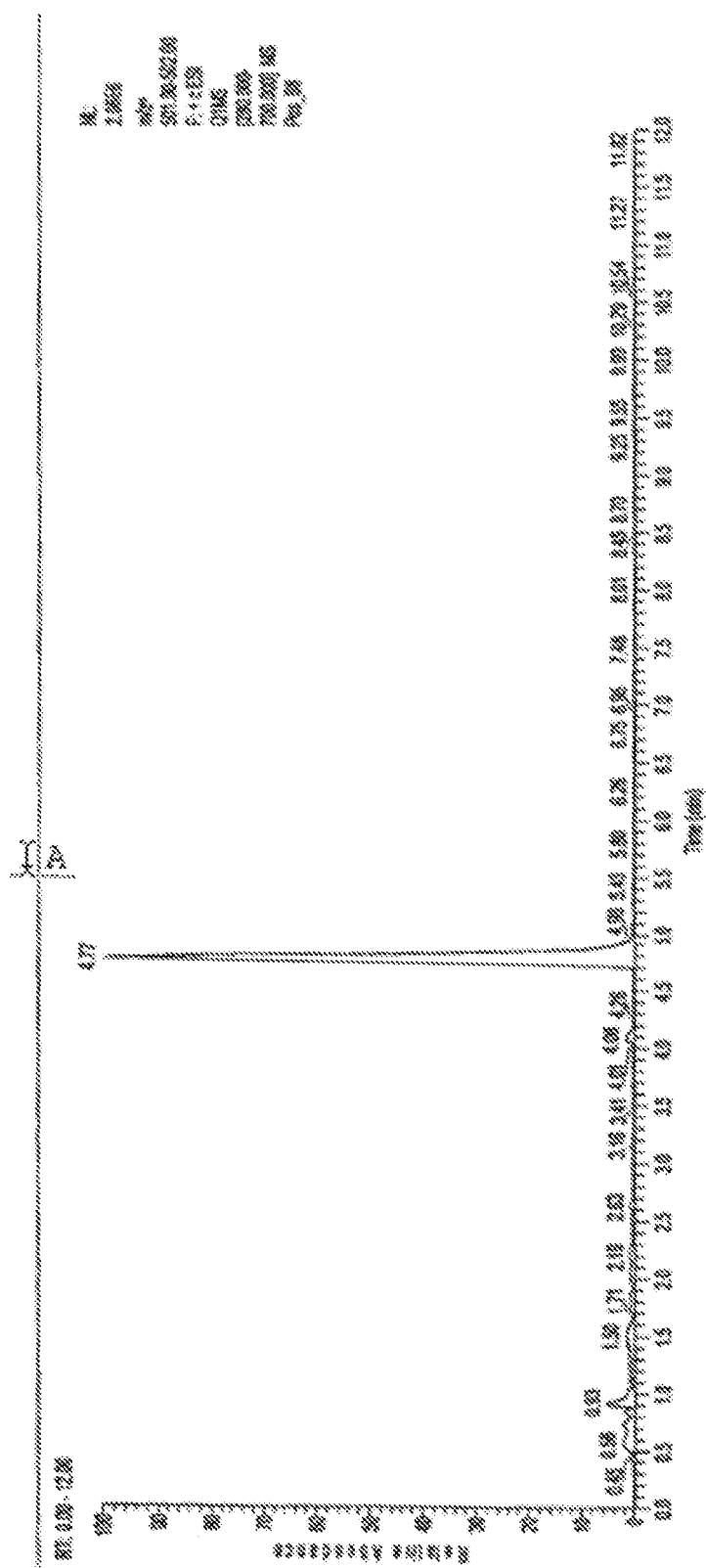
FIG. 7 shows the LC-MS mass peak 501 corresponding to the proton plus Na+ adduct of tetrahydroxysqualene in a sample from yeast strain EFSC3027 transformed with a plasmid expressing S. grosvenorii Epoxide hydrolase 2.

The successful boosting of oxidosqualene and dioxidosquale production in the strain EFSC3027 was demonstrated by production of tetrahydroxysqualene when either one of two soluble *S. grosvenorii* epoxide hydrolases was expressed in this strain. One epoxide hydrolase was *S. grosvenorii* Epoxide hydrolase 1 of SEQ ID NO:38. In order to prepare yeast expressing this a *S. cerevisiae* codon optimized *S. grosvenorii* Epoxide hydrolase 1 gene sequence of SEQ ID NO:37 was introduced in the yeast strain EFSC3027. The other epoxide hydrolase was *S. grosvenorii* Epoxide hydrolase 2 of SEQ ID NO:40. In order to prepare yeast expressing this a *S. cerevisiae* codon optimized *S. grosvenorii* Epoxide hydrolase 1 gene sequence of SEQ ID NO:39 was introduced in the yeast strain EFSC3027. FIG. 7 shows the LC-MS mass peak 501 corresponding to the proton plus Na+ adduct of tetrahydroxysqualene in a sample from yeast strain EFSC3027 transformed with a plasmid expressing *S. grosvenorii* Epoxide hydrolase 2. Tetrahydroxysqualene is made by the hydrolysis of 2,3 and 22,23 epoxide bonds of dioxidosqualene. No accumulation of tetrahydroxy squalene was detected in the EFSC301 background strain. Samples were made by boiling culture aliquots in 50% DMSO and then pelleting of cell material by centrifugation. Supernatants were then measured by ESI LC-MS.

A similar system for boosting oxidosqualene availability for β-amyrin production was described by Kirby, J et al in FEBS Journal 275 (2008) 1852-1859

Example 10

Production of Cucurbitadienol in Yeast Strain EFSC3027

Figure 8:
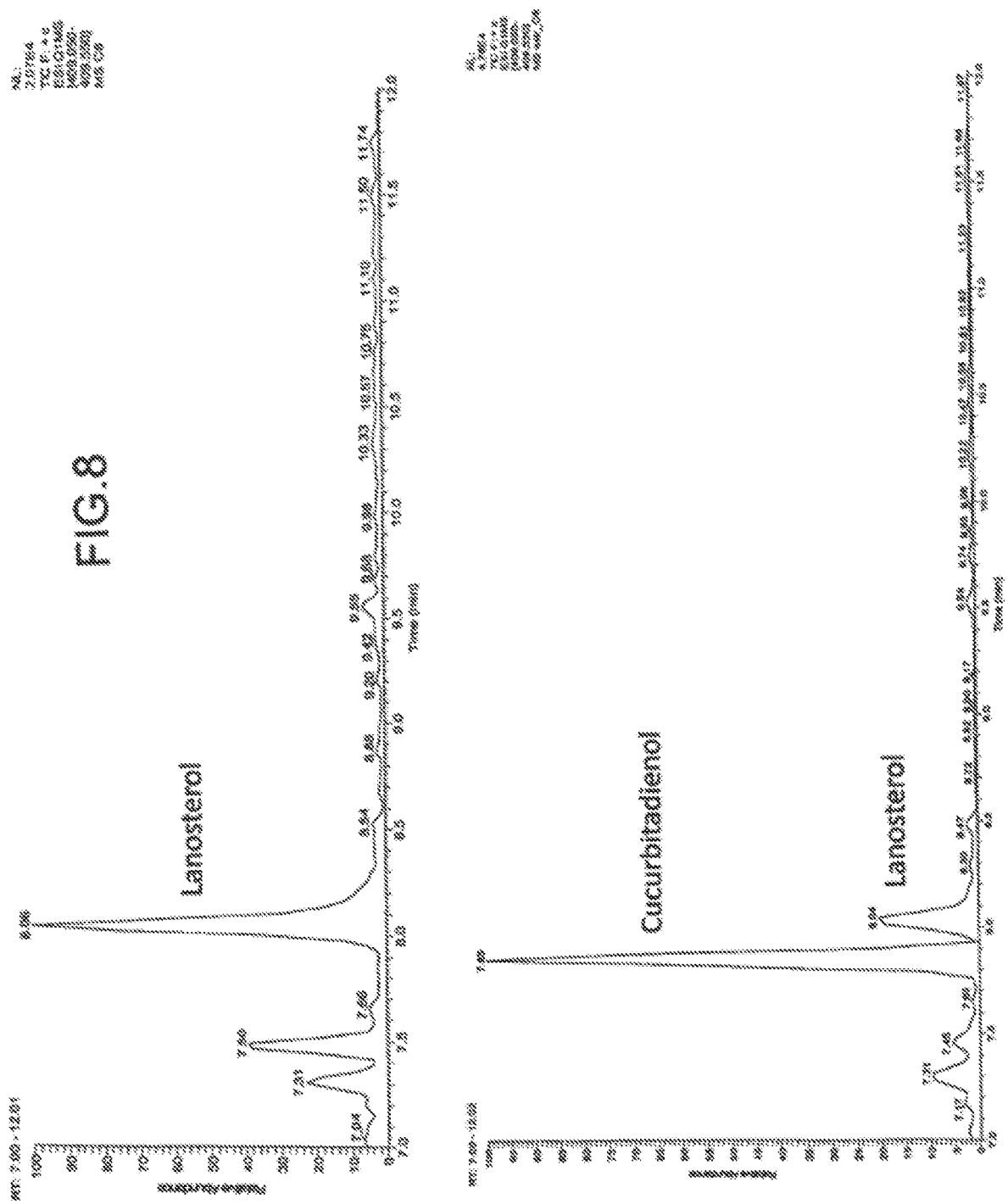
FIG. 8 shows the LC-MS chromatogram peak of lanosterol in yeast strain (upper panel) and LC-MS chromatogram peaks of cucurbitadienol and lanosterol in yeast strain EFSC3498, which expresses cucurbitadienol synthase (lower panel).

When a *S. cerevisiae* codon optimized gene copy of the *Siraitia grosvenorii* cucurbitadienol synthase of Accession No HQ128567 (sequence provided herein as SEQ ID NO:42) is integrated into the genome of yeast strain EFSC3027 and transcription of this gene is driven by the GPD1 promoter, the expression of the cucurbitadienol synthase results in production of cucurbitadienol in the yeast strain in amounts that are easily detectable by ESI LC-MS (see FIG. 8). The amino acid sequence of *Siraitia grosvenorii* cucurbitadienol synthase is provided herein as SEQ ID NO:43. The strain comprising SEQ ID NO:42 producing cucurbitadienol is called EFSC3498. Yeast strains were grown at 30° C. for 5 days in synthetic complete medium containing 2% glucose, and cucurbitadienol was extracted by boiling a culture sample in 50% ethanol/20% KOH for 5 minutes followed by extraction with an equal volume of hexane and then evaporation of hexane and resuspension of dried extract in methanol. FIG. 8 shows the LC-MS chromatogram peak of lanosterol in EFSC3027 (upper frame) and the LC-MS chromatogram peaks of cucurbitadienol and lanosterol in EFSC3498 (lower frame). The peak corresponding to lanosterol shows a retention time of ~8.05 whereas the peak corresponding to cucurbitadienol has a retention time of 7.85. Both lanosterol and cucurbitadienol shows a mass in the LC-MS chromatogram of 409.4 (proton adduct minus one $H_2O$)

Example 11

Figure 9:
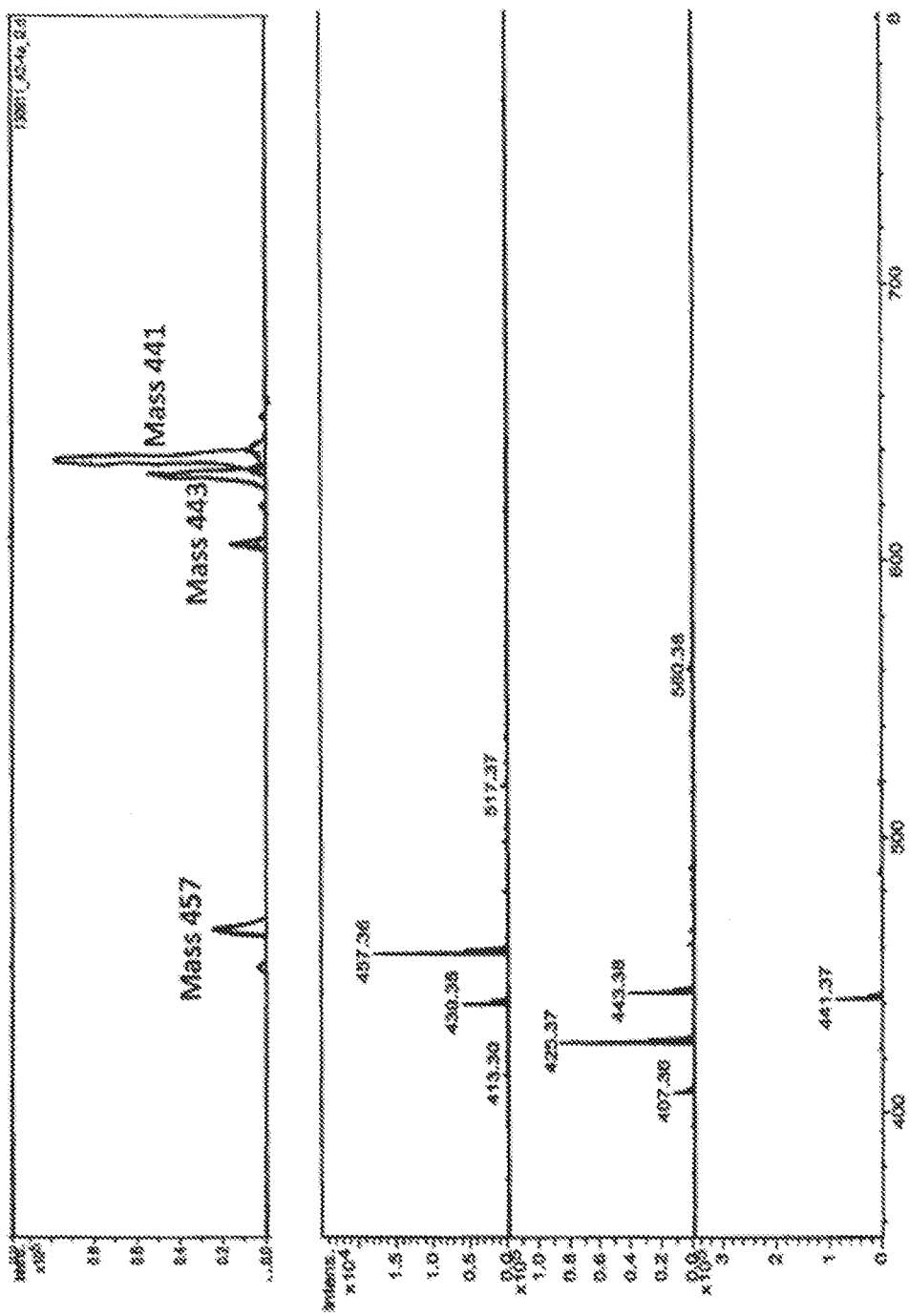
FIG. 9 shows the LC-MS chromatogram with the three peaks made when CYP5491 and CPR4497 are expressed in yeast strain EFSC3498 (upper panel), while the three lower panels show the fragmentation spectrum of these three peaks. The masses of the 3 peaks (443.38, 441.37 and 457.36) correspond in weight to proton adducts of hydroxylated cucurbitadienol, oxo cucurbitadienol and hydroxy plus oxo cucurbitadienol respectively.

Production of oxo and hydroxy cucurbitadienol in *S. cerevisiae* When the cucurbitadienol producing yeast strain EFSC3498 (prepared as described in Example 10) is transformed with two plasmids, one expressing the *S. grosvenorii* CYP5491 from a TEF1 promoter, the other expressing the *S. grosvenorii* CPR4497 also from a TEF1 promoter (DNA sequence encoding CPR4497 provided as SEQ ID NO:14) three conspicuous peaks emerge (see FIG. 9 for LC-MS chromatogram peaks). The amino acid sequence of *S. grosvenorii* CYP5491 is provided herein as SEQ ID NO:44 and the DNA sequence encoding *S. grosvenorii* CYP5491 is provided as SEQ ID NO:14. The amino acid sequence of *S. grosvenorii* CPR4497 is provided herein as SEQ ID NO:46 and the DNA sequence encoding *S. grosvenorii* CPR4497 is provided as SEQ ID NO:45. The upper frame in FIG. 9 shows the LC-MS chromatogram with the three peaks made when CYP5491 and CPR4497 are expressed in EFSC3498, while the three lower frames show the fragmentation spectrum of these three peaks. CYP5491 is 99% identical to acc. no. HQ128570 and HQ128571 at both the amino acid and nucleotide sequence level. The masses of the 3 peaks (443.38, 441.37 and 457.36) correspond in weight to proton adducts of hydroxylated cucurbitadienol, oxo cucurbitadienol and hydroxy plus oxo cucurbitadienol respectively. Without being bound by theory it is believed that the hydroxylated cucurbitadienol (protonated mass 443.38) and oxidated cucurbitadienol (protonated mass 441.37) is 11-hydroxy-cucurbitadienol and 11-oxo-cucurbitadienol, respectively. The peak that corresponds to both oxo plus hydroxy cucurbitadienol (protonated mass 457.36) could be 11-oxo-24,25 epoxy cucurbitadienol, formed, either from cyclization of dioxidosqualene by the cucurbitadienol synthase and 11 hydroxylation by CYP5491 (FIG. 10B) or by CYP5491 being multifunctional, making both the 11-oxidation and the 24,25-epoxidation (FIG. 10A).

Example 12

Figure 11A:
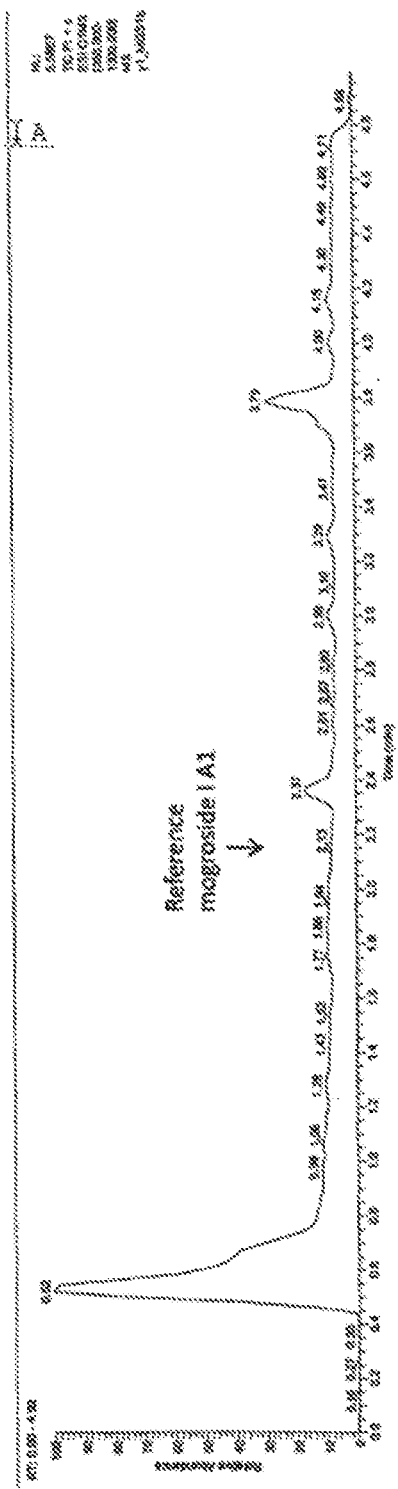
Figure 11B:
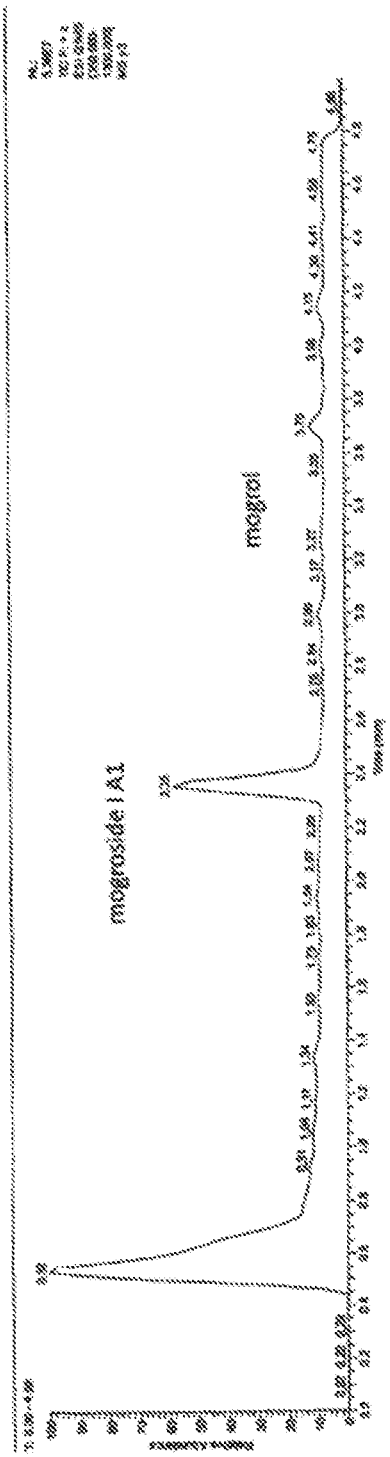
FIG. 11B shows the LC-MS chromatogram of a sample of yeast strain EFSC1563 expressing UGT1576 in a culture fed 50 uM mogrol.

Glycosylation of Mogrol in *S. cerevisiae* by Expression of *S. grosvenorii* UGTs UGTs 98, SK98 and 1576 were cloned from *S. grosvenorii* leaf and root cDNA by primers designed from fruit gene contigs assembled from illumina sequencing data. *S. grosvenorii* was purchased from Horizon Herbs, LLC, United States. The DNA sequence and protein sequence of UGT98 are provided herein as SEQ ID NO:51 and 53, respectively, whereas a SEQ ID NO:52 provides a DNA sequence encoding UGT98 codon optimised for expression in *S. cerevisiae*. The DNA sequence and protein sequence of UGTSK98 are provided herein as SEQ ID NO:49 and 50, respectively, The DNA sequence and protein sequence of UGT1576 are provided herein as SEQ ID NO:47 and 48, respectively. Yeast strain EFSC1563 has a deletion of the EXG1 gene and of the EXG2 gene both encoding and exo-1,3-beta-Glucanase. When yeast strain EFSC1563 (EFSC301 exg1 exg2) is transformed with a plasmid expressing UGT1576 driven by a GPD1 promoter and fed mogrol to a concentration in the growth medium of 10-100 uM, a clear formation of mogroside I A1 is detected by LC-MS (FIG. 11B). The produced mogroside I A1 shows the same retention time as the reference mogroside I A1 in the LC-MS analysis. FIG. 11A shows the LC-MS chromatogram of reference mogroside I A1, while 11B shows the peak from a sample of EFSC1563 expressing UGT1576 in a culture fed 50 uM mogrol. These data show that the UGT1576 gene encodes a glycosyltransferase with mogrol 24-OH UDP-glycosyltransferase activity. Samples were made by mixing culture aliquot 1:1 with DMSO followed by boiling (80° C.) for 5 minutes and pelleting by centrifugation. Supernatants were then subjected to ESI LC-MS.

Figure 12A:
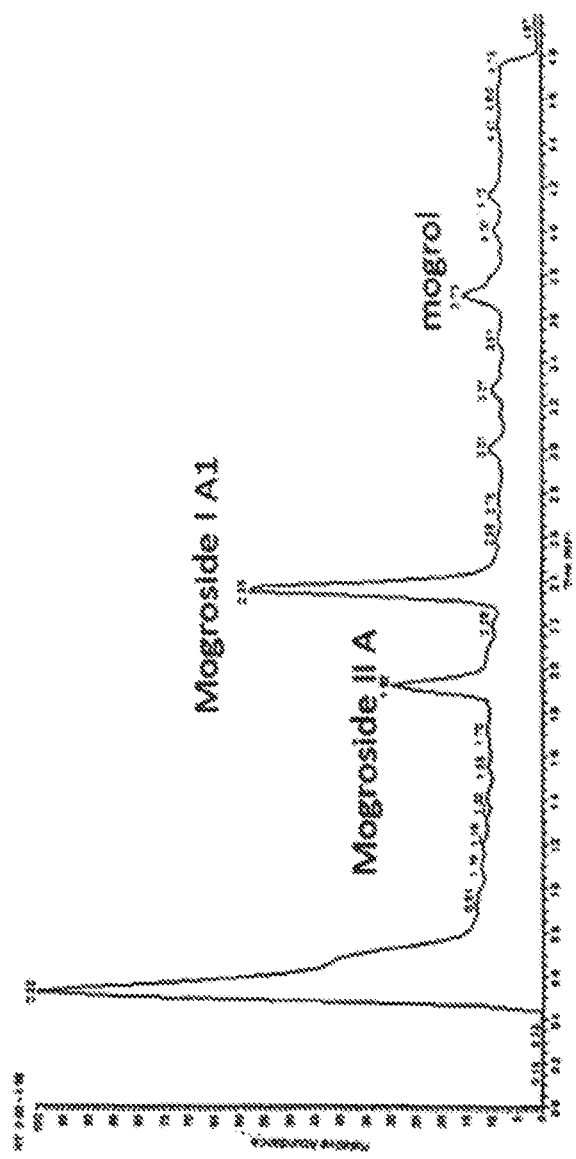
FIG. 12A shows the LC-MS chromatograms of samples from yeast strain EFSC1563 co-expressing UGT SK98 with UGT1576 showing production of di-glycosylated mogrol (mogroside II A).
Figure 12B:
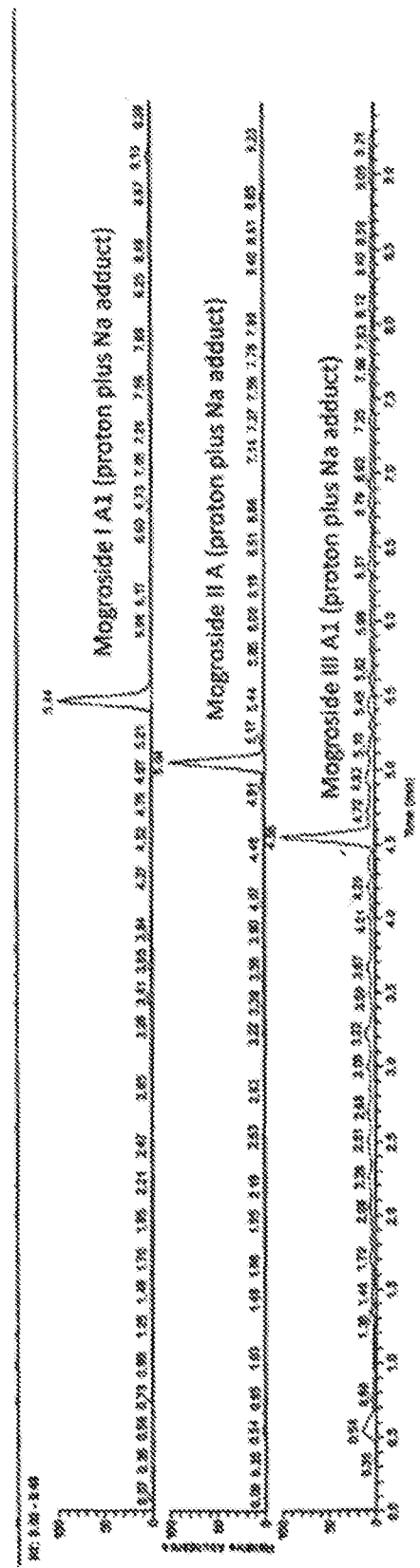
FIG. 12B shows LC-MS chromatograms of samples from yeast strain EFSC1563 co-expressing UGT98 with UGT1576 showing production of di and tri-glycosylated mogrol (middle and lower frames).

When UGTs 98 and SK98 cloned into yeast expression plasmids with expression from GPD1 promoters are transformed into EFSC1563 without co-transformation of a UGT1576 expression plasmid, no conversion of fed mogrol is detected. In contrast, co-expression of UGT98 or UGT SK98 with UGT1576 in EFSC1563 fed with mogrol results in further glycosylation of mogroside I A1. UGT SK98 co-expressed with UGT1576 results in production of di-glycosylated mogrol (mogroside II A, FIG. 12A), while co-expression with UGT98 results in di and tri-glycosylated mogrol (middle and lower frames, FIG. 12B). The di-glycosylated mogrol that is formed by both UGT98 and UGT SK98 has a different retention time than mogroside II E and mogroside II A1 during LC-MS, making it likely that it is mogroside II A. This means that both UGT98 and UGT SK98 can catalyse a 1,2 glucosylation of the glucose of mogroside I A1. UGT98 appears to be multifunctional, catalysing 1,2 glycosylation of mogroside I A1 resulting in production of mogroside II A, followed by what may be a 1,6 glycosylation of mogroside II A to form mogroside III A1 (FIG. 12B). We believe that UGT98 catalyses 1,6 glycosylation of mogroside II because mogrol itself is not glycosylated by the UGT98. It is therefore likely that the UGT98 is multifunctional, being both a 1,2 and 1,6 UDP-glucose glycosyl transferase of the 24-glucose moiety of mogrosides. UGTs 98 and SK98 belong to the UGT91 family of UDP-glucose glycosyltransferases and members of this family are known to be 1,2 and 1,6 glycosyltransferases.

Figure 13:
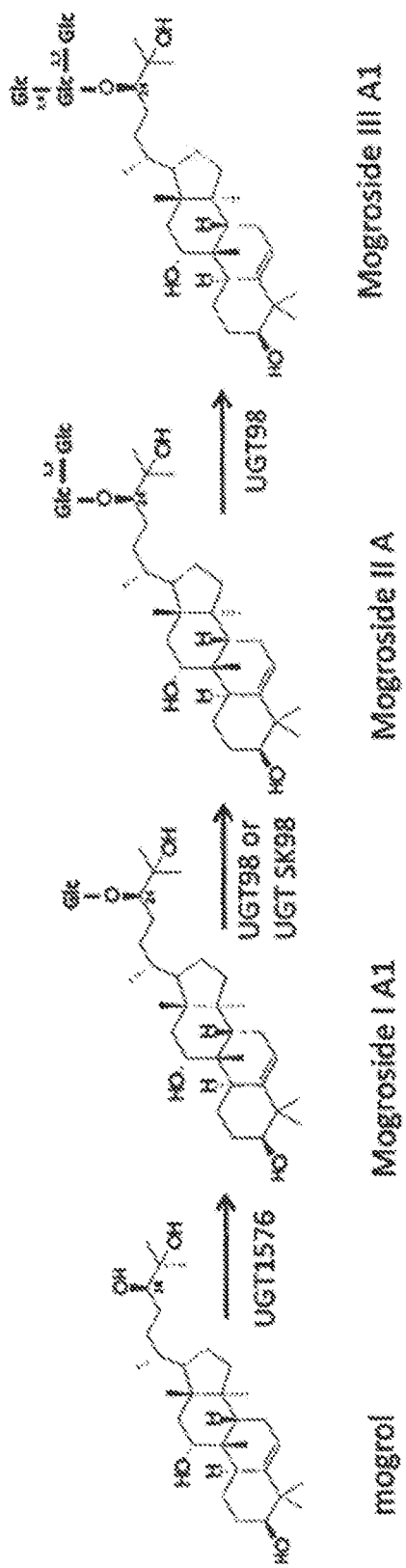
FIG. 13 shows a route from mogrol to Mogroside III A1 proposed by the present invention.

FIG. 13 schematically summarizes the glycosylation reactions from mogrol to mogroside Ill A1

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of producing a mogrol precursor, a mogroside precursor, and/or a mogroside compound in a recombinant host cell, comprising:
(a) a gene encoding a polypeptide capable of catalyzing conversion of oxido-squalene to produce cucurbitadienol;
wherein the polypeptide comprises a polypeptide having at least 90% sequence identity to the amino acid sequence set forth in SEQ ID NO:1;
(b) a gene encoding a polypeptide capable of catalyzing conversion of dioxido-squalene to produce 24,25 epoxy cucurbitadienol;
wherein the polypeptide comprises a polypeptide having at least 90% sequence identity to the amino acid sequence set forth in SEQ ID NO:1;
(c) a gene encoding a polypeptide capable of catalyzing hydroxylation of cucurbitadienol to produce 11-hydroxy-cucurbitadienol;
wherein the polypeptide comprises a polypeptide having at least 90% sequence identity to the amino acid sequence encoded by a nucleotide sequence set forth in SEQ ID NO:14;
(d) a gene encoding a polypeptide capable of catalyzing conversion of 11-hydroxy-cucurbitadienol to produce mogrol;
wherein the polypeptide comprises a polypeptide having at least 90% sequence identity to the amino acid sequence encoded by a nucleotide sequence set forth in SEQ ID NO:5;
(e) a gene encoding a polypeptide capable of catalyzing epoxidation of 11-hydroxy-cucurbitadienol to produce 11-hydroxy-24,25 epoxy cucurbitadienol;
wherein the polypeptide comprises a polypeptide having at least 90% sequence identity to the amino acid sequence encoded by a nucleotide sequence set forth in SEQ ID NO:5;
(f) a gene encoding a polypeptide capable of catalyzing conversion of 11-hydroxy-24,25 epoxy cucurbitadienol to produce mogrol;
wherein the polypeptide comprises a polypeptide having at least 90% sequence identity to the amino acid sequence encoded by a nucleotide sequence set forth in SEQ ID NO:5;
(g) a gene encoding a polypeptide capable of catalyzing epoxidation of cucurbitadienol to produce 24,25 epoxy cucurbitadienol;
wherein the polypeptide comprises a polypeptide having at least 90% sequence identity to the amino acid sequence encoded by a nucleotide sequence set forth in SEQ ID NO:5;
(h) a gene encoding a polypeptide capable of catalyzing hydroxylation of 24,25 epoxy cucurbitadienol to produce 11-hydroxy-24,25 epoxy cucurbitadienol;
wherein the polypeptide comprises a polypeptide having at least 90% sequence identity to the amino acid sequence encoded by a nucleotide sequence set forth in SEQ ID NO:14; and/or
(i) a gene encoding a polypeptide capable of beta-1,6-glycosylation of the C2' position of the 24-O-glucose and/or beta-1,2-glycosylation of the C6' position of the 3-O-glucose and/or the 24-O-glucose of the glycosylated mogroside compound;
wherein the one or more polypeptides comprises a polypeptide having at least 90% sequence identity to the amino acid sequence encoded by the nucleotide sequence set forth in SEQ ID NO:26;
wherein at least one of the genes is a recombinant gene;
comprising growing the recombinant host cell in a culture medium, under conditions in which the genes are expressed; and
thereby producing the mogrol precursor, the mogroside precursor, and/or the mogroside compound in the recombinant host cell.

2. The method of claim 1, wherein the recombinant host cell comprises genes recited in items (a), (c), (d), and (i).

3. The method of claim 1, wherein the recombinant host cell comprises genes recited in items (a), (c), (e), (f), and (i).

4. The method of claim 1, wherein the recombinant host cell comprises genes recited in items (a), (g), (h), (f), and (i).

5. The method of claim 1, wherein the recombinant host cell comprises genes recited in items (c), (d), and (i).

6. The method of claim 1, wherein the recombinant host cell comprises genes recited in items (b), (f), (h), and (i).

7. The method of claim 1, wherein the recombinant host cell comprises genes recited in items (f), (h), and (i).

8. The method of claim 1, wherein the recombinant host cell comprises genes recited in item (i).

9. The method of claim 1, further comprising isolating the produced mogrol precursor, the mogroside precursor, and/or the mogroside compound.

10. The method of claim 1, wherein the mogrol precursor is oxidosqualene.

11. The method of claim 1, wherein the mogroside precursor is a tri-glycosylated mogrol.

12. The method of claim 1, wherein the mogroside compound is a mogroside compound di-glycosylated at C3' position and tri-glycosylated at C24'.

13. The method of claim 12, wherein
the mogroside compound di-glycosylated at C3' position and tri-glycosylated at C24' position is mogroside V.

14. An in vivo method for transferring a sugar moiety to a mogrol, a glycosylated mogroside compound, or both the mogrol and the glycosylated mogroside compound, comprising contacting the mogrol, the glycosylated mogroside compound, or both the mogrol and the glycosylated mogroside compound with one or more recombinant polypeptides capable of beta 1,6-glycosylation of the C2' position of the 24-O-glucose and/or beta-1,2-glycosylation of the C6' position of the 3-O-glucose and/or the 24-O-glucose of the glycosylated mogroside compound and one or more UDP-sugars, under suitable reaction conditions for the transfer of one or more sugar moieties from the one or more UDP-sugars to the mogrol, the glycosylated mogroside compound, or both the mogrol and the glycosylated mogroside compound;

the method comprising growing a recombinant host cell comprising a gene encoding a polypeptide capable of beta-1,6-glycosylation of the C2' position of the 24-O-glucose and/or beta-1,2-glycosylation of the C6' position of the 3-O-glucose and/or the 24-O-glucose of the glycosylated mogroside compound;

wherein the one or more polypeptides comprises a polypeptide having at least 90% sequence identity to the amino acid sequence encoded by the nucleotide sequence set forth in SEQ ID NO:26;

wherein at least one of the genes is a recombinant gene, under conditions in which one or more of the genes are expressed;

wherein contacting the mogrol, the mogroside compound glycosylated at C3' position and tri-glycosylated at C24' position with the polypeptide comprises contacting the mogroside compound glycosylated at C3' position and tri-glycosylated at C24' position with the polypeptide produced by the recombinant host cell;

wherein the recombinant host cell is a microorganism that is a plant cell, a mammalian cell, an insect cell, a fungal cell, an algal cell, or a bacterial cell; and wherein a mogroside compound is produced in a cell culture broth upon transfer of the sugar moiety.

15. The method of claim 14, wherein
the UDP-sugar is UDP-glucose, and the mogroside compound di-glycosylated at C3' position and tri-glycosylated at C24' position is produced upon transfer of the glucose moiety to the C6' position of the 3-0-glucose of the mogroside compound glycosylated at C3' position and tri-glycosylated at C24' position.

16. The method of claim 14, wherein the one or more UDP-sugar comprises UDP-glucose.

17. The method of claim 14, wherein the mogrol is a plant-derived mogrol.

18. A method of producing a mogrol precursor, a mogroside precursor, and/or a mogroside compound, comprising whole cell bioconversion of a plant-derived or a synthetic mogrol precursor or a mogroside precursor in a cell culture medium of a recombinant host cell comprising:

(a) a gene encoding a polypeptide capable of catalyzing conversion of oxido-squalene to produce cucurbitadienol;
wherein the polypeptide comprises a polypeptide having at least 90% sequence identity to the amino acid sequence set forth in SEQ ID NO:1;

(b) a gene encoding a polypeptide capable of catalyzing conversion of dioxido-squalene to produce 24,25 epoxy cucurbitadienol;
wherein the polypeptide comprises a polypeptide having at least 90% sequence identity to the amino acid sequence set forth in SEQ ID NO:1;

(c) a gene encoding a polypeptide capable of catalyzing hydroxylation of cucurbitadienol to produce 11-hydroxy-cucurbitadienol;
wherein the polypeptide comprises a polypeptide having at least 90% sequence identity to the amino acid sequence encoded by a nucleotide sequence set forth in SEQ ID NO:14;

(d) a gene encoding a polypeptide capable of catalyzing conversion of 11-hydroxy-cucurbitadienol to produce mogrol;
wherein the polypeptide comprises a polypeptide having at least 90% sequence identity to the amino acid sequence encoded by a nucleotide sequence set forth in SEQ ID NO:5;

(e) a gene encoding a polypeptide capable of catalyzing epoxidation of 11-hydroxy-cucurbitadienol to produce 11-hydroxy-24,25 epoxy cucurbitadienol;
wherein the polypeptide comprises a polypeptide having at least 90% sequence identity to the amino acid sequence encoded by a nucleotide sequence set forth in SEQ ID NO:5;

(f) a gene encoding a polypeptide capable of catalyzing conversion of 11-hydroxy-24,25 epoxy cucurbitadienol to produce mogrol;
wherein the polypeptide comprises a polypeptide having at least 90% sequence identity to the amino acid sequence encoded by a nucleotide sequence set forth in SEQ ID NO:5;

(g) a gene encoding a polypeptide capable of catalyzing epoxidation of cucurbitadienol to produce 24,25 epoxy cucurbitadienol;
wherein the polypeptide comprises a polypeptide having at least 90% sequence identity to the amino acid sequence encoded by a nucleotide sequence set forth in SEQ ID NO:5;

(h) a gene encoding a polypeptide capable of catalyzing hydroxylation of 24,25 epoxy cucurbitadienol to produce 11-hydroxy-24,25 epoxy cucurbitadienol;
wherein the polypeptide comprises a polypeptide having at least 90% sequence identity to the amino acid sequence encoded by a nucleotide sequence set forth in SEQ ID NO:14; and/or (i) a gene encoding a polypeptide capable of beta 1,6-glycosylation of the C2' position of the 24-O-glucose, and/or beta-1,2-glycosilation of the C6' position of the 3-O-glucose and/or the 24-O-glucose of the glycosylated mogroside compound;
wherein the one or more polypeptides comprises a polypeptide having at least 90% sequence identity to the amino acid sequence encoded by the nucleotide sequence set forth in SEQ ID NO:26;

wherein at least one of the genes is a recombinant gene;
wherein at least one of the polypeptides is a recombinant polypeptide expressed in the recombinant host cell;
wherein the recombinant host cell is a microorganism that is a plant cell, a mammalian cell, an insect cell, a fungal cell, an algal cell, or a bacterial cell;
and producing the mogrol precursor, the mogroside precursor, and/or the mogroside compound thereby.

19. The method of claim 1, wherein the recombinant host cell is a microorganism that is a plant cell, a mammalian cell, an insect cell, a fungal cell, an algal cell, or a bacterial cell.

* * * * *

SEQUENCE LISTING

```
<160> NUMBER OF SEQ ID NOS: 41

<210> SEQ ID NO 1
<211> LENGTH: 764
<212> TYPE: PRT
<213> ORGANISM: Cucurbita pepo
```

```
<400> SEQUENCE: 1

Met Trp Arg Leu Lys Val Gly Ala Glu Ser Val Gly Glu Glu Asp Glu
1               5                   10                  15

Lys Trp Val Lys Ser Val Ser Asn His Leu Gly Arg Gln Val Trp Glu
            20                  25                  30

Phe Cys Ala Asp Ala Ala Ala Asp Thr Pro His Gln Leu Leu Gln Ile
        35                  40                  45

Gln Asn Ala Arg Asn His Phe His His Asn Arg Phe His Arg Lys Gln
    50                  55                  60

Ser Ser Asp Leu Phe Leu Ala Ile Gln Tyr Glu Lys Glu Ile Ala Lys
65                  70                  75                  80

Gly Ala Lys Gly Gly Ala Val Lys Val Lys Glu Gly Glu Glu Val Gly
                85                  90                  95

Lys Glu Ala Val Lys Ser Thr Leu Glu Arg Ala Leu Gly Phe Tyr Ser
            100                 105                 110

Ala Val Gln Thr Arg Asp Gly Asn Trp Ala Ser Asp Leu Gly Gly Pro
        115                 120                 125

Leu Phe Leu Leu Pro Gly Leu Val Ile Ala Leu His Val Thr Gly Val
130                 135                 140

Leu Asn Ser Val Leu Ser Lys His His Arg Val Glu Met Cys Arg Tyr
145                 150                 155                 160

Leu Tyr Asn His Gln Asn Glu Asp Gly Gly Trp Gly Leu His Ile Glu
                165                 170                 175

Gly Thr Ser Thr Met Phe Gly Ser Ala Leu Asn Tyr Val Ala Leu Arg
            180                 185                 190

Leu Leu Gly Glu Asp Ala Asp Gly Gly Asp Gly Gly Ala Met Thr Lys
        195                 200                 205

Ala Arg Ala Trp Ile Leu Glu Arg Gly Gly Ala Thr Ala Ile Thr Ser
210                 215                 220

Trp Gly Lys Leu Trp Leu Ser Val Leu Gly Val Tyr Glu Trp Ser Gly
225                 230                 235                 240

Asn Asn Pro Leu Pro Pro Glu Phe Trp Leu Leu Pro Tyr Ser Leu Pro
                245                 250                 255

Phe His Pro Gly Arg Met Trp Cys His Cys Arg Met Val Tyr Leu Pro
            260                 265                 270

Met Ser Tyr Leu Tyr Gly Lys Arg Phe Val Gly Pro Ile Thr Pro Lys
        275                 280                 285

Val Leu Ser Leu Arg Gln Glu Leu Tyr Thr Ile Pro Tyr His Glu Ile
290                 295                 300

Asp Trp Asn Lys Ser Arg Asn Thr Cys Ala Lys Glu Asp Leu Tyr Tyr
305                 310                 315                 320

Pro His Pro Lys Met Gln Asp Ile Leu Trp Gly Ser Ile Tyr His Val
                325                 330                 335

Tyr Glu Pro Leu Phe Thr Arg Trp Pro Gly Lys Arg Leu Arg Glu Lys
            340                 345                 350

Ala Leu Gln Ala Ala Met Lys His Ile His Tyr Glu Asp Glu Asn Ser
        355                 360                 365

Arg Tyr Ile Cys Leu Gly Pro Val Asn Lys Val Leu Asn Met Leu Cys
370                 375                 380

Cys Trp Val Glu Asp Pro Tyr Ser Asp Ala Phe Lys Leu His Leu Gln
385                 390                 395                 400

Arg Val His Asp Tyr Leu Trp Val Ala Glu Asp Gly Met Arg Met Gln
```

Gly Tyr Asn Gly Ser Gln Leu Trp Asp Thr Ala Phe Ser Ile Gln Ala
            405                 410                 415
                420                 425                 430

Ile Val Ala Thr Lys Leu Val Asp Ser Tyr Ala Pro Thr Leu Arg Lys
                435                 440                 445

Ala His Asp Phe Val Lys Asp Ser Gln Ile Gln Glu Asp Cys Pro Gly
            450                 455                 460

Asp Pro Asn Val Trp Phe Arg His Ile His Lys Gly Ala Trp Pro Leu
465                 470                 475                 480

Ser Thr Arg Asp His Gly Trp Leu Ile Ser Asp Cys Thr Ala Glu Gly
                485                 490                 495

Leu Lys Ala Ser Leu Met Leu Ser Lys Leu Pro Ser Thr Met Val Gly
            500                 505                 510

Glu Pro Leu Glu Lys Asn Arg Leu Cys Asp Ala Val Asn Val Leu Leu
            515                 520                 525

Ser Leu Gln Asn Asp Asn Gly Gly Phe Ala Ser Tyr Glu Leu Thr Arg
            530                 535                 540

Ser Tyr Pro Trp Leu Glu Leu Ile Asn Pro Ala Glu Thr Phe Gly Asp
545                 550                 555                 560

Ile Val Ile Asp Tyr Pro Tyr Val Glu Cys Thr Ala Ala Thr Met Glu
                565                 570                 575

Ala Leu Thr Leu Phe Lys Lys Leu His Pro Gly His Arg Thr Lys Glu
            580                 585                 590

Ile Asp Thr Ala Ile Gly Lys Ala Ala Asn Phe Leu Glu Lys Met Gln
            595                 600                 605

Arg Ala Asp Gly Ser Trp Tyr Gly Cys Trp Gly Val Cys Phe Thr Tyr
            610                 615                 620

Ala Gly Trp Phe Gly Ile Lys Gly Leu Val Ala Ala Gly Arg Thr Tyr
625                 630                 635                 640

Asn Ser Cys Leu Ala Ile Arg Lys Ala Cys Glu Phe Leu Leu Ser Lys
                645                 650                 655

Glu Leu Pro Gly Gly Gly Trp Gly Glu Ser Tyr Leu Ser Cys Gln Asn
            660                 665                 670

Lys Val Tyr Thr Asn Leu Glu Gly Asn Lys Pro His Leu Val Asn Thr
            675                 680                 685

Ala Trp Val Leu Met Ala Leu Ile Glu Ala Gly Gln Gly Glu Arg Asp
            690                 695                 700

Pro Ala Pro Leu His Arg Ala Arg Leu Leu Met Asn Ser Gln Leu
705                 710                 715                 720

Glu Asn Gly Asp Phe Val Gln Gln Glu Ile Met Gly Val Phe Asn Lys
                725                 730                 735

Asn Cys Met Ile Thr Tyr Ala Ala Tyr Arg Asn Ile Phe Pro Ile Trp
            740                 745                 750

Ala Leu Gly Glu Tyr Cys His Arg Val Leu Thr Glu
            755                 760

<210> SEQ ID NO 2
<211> LENGTH: 250
<212> TYPE: PRT
<213> ORGANISM: Siraitia grosvenorii

<400> SEQUENCE: 2

Leu Glu Arg Asn Arg Leu Cys Asp Ala Val Asn Val Leu Leu Ser Leu
1               5                   10                  15

Gln Asn Asp Asn Gly Gly Phe Ala Ser Tyr Glu Leu Thr Arg Ser Tyr
            20                  25                  30

Pro Trp Leu Glu Leu Ile Asn Pro Ala Glu Thr Phe Gly Asp Ile Val
         35                  40                  45

Ile Asp Tyr Pro Tyr Val Glu Cys Thr Ser Ala Thr Met Glu Ala Leu
 50                  55                  60

Thr Leu Phe Lys Lys Leu His Pro Gly His Arg Thr Lys Glu Ile Asp
 65                  70                  75                  80

Thr Ala Ile Val Arg Ala Ala Asn Phe Leu Glu Asn Met Gln Arg Thr
                 85                  90                  95

Asp Gly Ser Trp Tyr Gly Cys Trp Gly Val Cys Phe Thr Tyr Ala Gly
            100                 105                 110

Trp Phe Gly Ile Lys Gly Leu Val Ala Ala Gly Arg Thr Tyr Asn Asn
         115                 120                 125

Cys Leu Ala Ile Arg Lys Ala Cys Asp Phe Leu Leu Ser Lys Glu Leu
 130                 135                 140

Pro Gly Gly Gly Trp Gly Glu Ser Tyr Leu Ser Cys Gln Asn Lys Val
145                 150                 155                 160

Tyr Thr Asn Leu Glu Gly Asn Arg Pro His Leu Val Asn Thr Ala Trp
                 165                 170                 175

Val Leu Met Ala Leu Ile Glu Ala Gly Gln Ala Glu Arg Asp Pro Thr
            180                 185                 190

Pro Leu His Arg Ala Ala Arg Leu Leu Ile Asn Ser Gln Leu Glu Asn
         195                 200                 205

Gly Asp Phe Pro Gln Gln Glu Ile Met Gly Val Phe Asn Lys Asn Cys
 210                 215                 220

Met Ile Thr Tyr Ala Ala Tyr Arg Asn Ile Phe Pro Ile Trp Ala Leu
225                 230                 235                 240

Gly Glu Tyr Cys His Arg Val Leu Thr Glu
                 245                 250

<210> SEQ ID NO 3
<211> LENGTH: 1572
<212> TYPE: DNA
<213> ORGANISM: Siraitia grosvenorii

<400> SEQUENCE: 3
atggaactct ctctctaccaa aactgcagcc gagatcatcg ctgttgtctt gtttttctac      60
gctctcatcc ggctattatc tggaagattc agctctcaac agaagagact gccacctgaa     120
gccggtggcg cctggccact gatcggccat ctccatctcc taggtgggtc ggaacctgca     180
cataaaacct tggcgaacat ggcggacgcc tacggaccag ttttacgtt gaaactgggc      240 atgcatacag ctttggttat gagcagttgg gaaatagcga gagtgctt tactaaaaac      300 gacagaatct ttgcctcccg ccccatagtc actgcctcaa agcttctcac ctataaccat     360
accatgtttg ggtcagcca atatggtcca ttctggcgcc atatgcgcaa aatagccacg     420
cttcaactcc tctcaaacca ccgcctcgag cagctccaac acatcagaat atcggaggtc     480
cagacttcga ttaagaaact gtacgagttg tgggtcaaca gcagaaataa tggaggcgag     540
aaagtgttgg tggagatgaa gacgtggttc ggaggcataa ccttgaacac catattcagg     600
atggtggtcg gaaagcgatt ctcgactgct ttcgaaggca gtggtggcga acggtatcgg     660
aaggcgttga gggattctct tgaatggttt ggggcattcg ttccgtcaga ttcattcccg     720
tttttaagat ggttggattt gggaggatat gagaaggcga tgaagaagac ggcgagtgtg     780

```
ctggacgagg tgcttgataa atggctcaaa gagcatcagc agaggagaaa ctccggtgaa      840
ctggagacgg aggagcacga cttcatgcac gtgatgctgt ctattgttaa ggatgatgaa      900
gaactatccg gctacgatgc cgatacagtc acaaaagcta catgtttgaa tttaatagtt      960
ggtggattcg acactacaca agtaactatg acatgggctc tttctttgct tctcaacaat     1020
gaagaggtat taaaaaaggc ccaacttgaa ctagacgaac aagttggaag agagaggttt     1080
gtggaagagt ccgatgttaa aaatctgtta tatctccagg ccatcgtgaa ggaaactttg     1140
cgtttgtacc cttcagcgcc aatctcgaca tttcatgagg ccatggaaga ttgcactgtt     1200
tctggctacc acatctttc agggacgcgt ttgatggtga atcttcaaaa gcttcaaaga      1260
gatccacttg catgggagga tccatgtgac tttcgaccgg agagatttct gacaactcat     1320
aaggatttcg atcttagagg acatagtcct caattgatac catttgggag tggtcgaaga     1380
atatgccctg gcatctcgtt tgccattcaa gttttgcatc ttacgcttgc aaatctactt     1440
catgggtttg acattggaag gccatctcat gaaccaatcg atatgcagga gagtaaagga     1500
ctaacgagta ttaaaacaac tccacttgag gttgttttag ctccacgcct tgctgctcaa     1560
gtttatgagt ga                                                         1572

<210> SEQ ID NO 4
<211> LENGTH: 1497
<212> TYPE: DNA
<213> ORGANISM: Siraitia grosvenorii

<400> SEQUENCE: 4
atgccgatcg cagaaggtgc agtctctgat ttgtttggtc gcccactctt ctttgcacta       60
tatgattggt tcttagagca tggatctgtt tataaacttg cctttggacc aaaagccttt      120
gttgttgtat cagatcccat tgtggcaaga tatattcttc gagaaaatgc atttggttat      180
gacaagggag tgcttgctga tattttagaa ccgataatgg gtaaaggact aataccagct      240
gaccttggca cttggaagca gaggagacga gttattgctc caggattcca tgccttgtac      300
ttggaagcta tgaccaaagt atttgccaat tgttcagaac gatcaatatt gaaattggag      360
aagcttctag agaaggtgaa actacaggag aataaaacca ttgagttgga tatggaagca      420
gagttttcaa gtttggctct tgatatcatt ggactcggtg ttttcaacta tgattttggt      480
tctgtaacca agaatctccc ggtgattaag gctgtatatg ggactctttt tgaagcagag      540
catagatcga ctttctatat cccatattgg aaagtacctt tggcaaggtg atagtccca      600
aggcagcgta attccatgg tgaccttaag gttattaatg agtgtcttga tggcctaata      660
cgcaacgcaa gagaaacccg agacgaaacg gatgttgaga aattgcagca agggactac      720
ttaaatctca aggatgccag tcttttgcgt ttcttagttg atatgcgggg agctgatgtt      780
gatgatcgcc agcttaggga cgatctgatg acgatgctta ttgctggcca tgaaacaact      840
gctgctgtgc ttacatgggc tgtttttttg cttgcacaaa atccttcaaa aatgaaaaaa      900
gcgcaagcag agattgattt ggttcttggc atggggaggc aactttttga atcatttaaa     960
gcattgaagt acatcagact tatcgttgca gagactcttc gtttgtttcc tcagcctcca    1020
ttgctgataa tgagctctc caaatcagat atattaccag aggatacaa tggtgacaaa    1080
actggatatg caattcctgc agggactgac atcttcatct ctgtttacaa tctccacaga    1140
tctccctact tctgggataa tcctcaagaa tttgaaccag agagattcca gtaaagagg    1200
gcaagcgagg gaattgaagg atgggatggt ttcgacccat ctagaagccc tggagctcta    1260
taccgaatg agattgtagc agacttttcc ttcttaccat tggtggagg ccctagaaaa    1320
```

-continued

```
tgtgtgggag atcaatttgc tctaatggag tcaactatag cattggccat gttactgcag    1380
aagtttgatg tggagctaaa aggaagtcca gaatctgtag aactagttac tggagccaca    1440
atacatacca aaagtggggt tgtggtgcaaa ctgagaagaa gatcacaagt aaactga     1497
```

<210> SEQ ID NO 5
<211> LENGTH: 1563
<212> TYPE: DNA
<213> ORGANISM: Siraitia grosvenorii

<400> SEQUENCE: 5

```
atggaaatgt cctcaagtgt cgcagccaca atcagtatct ggatggtcgt cgtatgtatc     60
gtaggtgtag gttggagagt cgtaaattgg gtttggttga gaccaaagaa attggaaaag    120
agattgagag aacaaggttt ggccggtaat tcttacagat tgttgttcgg tgacttgaag    180
gaaagagctg caatggaaga acaagcaaat tcaaagccta taaacttctc ccatgacatc    240
ggtccaagag ttttcccttc aatgtacaag accatccaaa actacggtaa aaactcctac    300
atgtggttag gtccataccc tagagtccac atcatggatc cacaacaatt gaagaccgtt    360
tttactttgg tctacgacat tcaaaagcca aatttgaacc ctttgattaa attcttgtta    420
gatggtatcg ttacacatga aggtgaaaag tgggctaagc acagaaagat tattaaccca    480
gcattccatt tggaaaagtt gaaggatatg atacctgctt tctttcactc atgtaatgaa    540
atcgtcaacg aatgggaaag attgatttca aaagaaggtt cctgcgaatt ggatgtaatg    600
ccttatttgc aaaatttggc cgctgacgcc atttcaagaa ccgctttggg ttcttcatac    660
gaagaaggta aatgatcttc ccaattgttg aaggaattga ctgatttggt tgtcaaggta    720
gcttttggtg tttatattcc aggttggaga ttcttgccta caagagtaa caacaaaatg    780 aaggaaatta atagaaaaat caagtctttg ttgttgggta tcattaacaa gagacaaaag    840
gcaatggaag aaggtgaagc cggtcaatct gatttgttgg gtatattaat ggaaagtaat    900
tctaacgaaa tccaaggtga aggtaataac aaggaagatg catgtctat tgaagacgtc    960 atcgaagagt gtaaggtatt ttatataggt ggtcaagaaa ctacagcaag attattgatc   1020
tggactatga tattgttgtc cagtcataca gaatggcaag aaagagccag aaccgaagtc   1080
ttgaaggtat ttggtaataa gaaaccagat ttcgacggtt tgtcaagatt gaaggtagtt   1140
actatgatct tgaacgaagt tttaagattg tacccacctg cttccatgtt gacaagaatc   1200
atccaaaagg aaacaagagt tggtaaatta accttgccag caggtgttat cttgataatg   1260
cctatcatct tgatacatag agatcacgac ttgtggggtg aagatgctaa cgagtttaaa   1320
ccagaaagat tcagtaaagg tgtttctaag gcagccaaag tccaaccagc cttttttccct   1380 tttggttggg gtcctagaat ttgcatgggt caaaacttcg ctatgatcga agctaagatg   1440
gcattgagtt tgatcttgca aagattttct ttcgaattgt cttcatccta cgttcatgca   1500
ccaactgtcg tcttcactac acaaccacaa cacggtgccc acatcgtttt gagaagtta   1560 tga                                                                1563
```

<210> SEQ ID NO 6
<211> LENGTH: 1602
<212> TYPE: DNA
<213> ORGANISM: Siraitia grosvenorii

<400> SEQUENCE: 6

```
atggaaccac aaccaagtgc ggaattcaac tggaatcaca gcctaagcac cgtcgctatc     60
```

```
ggtgtcattg ccattatttt cttccgtttt ctcgtcaaaa gagtcaccgg cgccggtgag      120
cgaaagggtc cgaagccgcc aaaagtagcc ggagggtggc ctctaattgg ccacctccct      180
ctcctcggag gacctgaact gccccatgtc aaactgggtg gtttggctga taaatatggt      240
ccaatcttct cgatccggct gggtgtccac tccgccgtcg tgataaacag ttgggaggcg      300
gcgaaacagt tattaaccaa ccatgacgtc gccgtctctt cccgccccca aatgctcggc      360
ggaaaactcc tgggctacaa ctacgccgtg tttggtttcg gacccctacgg ctcttactgg      420 cgcaacatgc gcaagataac cacgcaagag cttctatcca atagcagaat ccagctccta      480
agagacgttc gagcgtcaga agtgaaccaa ggcataaaag agctctacca gcactggaaa      540
gaaagaagag acggtcacga ccaagccttg gtggaactgc agcagtgggt cggggacttg      600
actatgaatc tgattctcgg agtcatcgcc gggaaaaggt tctttggagc tgcagcaacg      660
gtagacgagg aagaggcgcg acggagccat aaagcattga aggagttgtt acattatatg      720 gggcttttc tactgggtga tgctgttcca tatctaggat ggttggacgt cggcggccat      780
gtgaaggcga tgaagaaaac ttcaaaagaa ttggaccgta tgttaacaca gtggttggag      840
gagcacaaga aggaaggacc caagaaagat cataaagact tcatggacgt gatgctttca      900
gttctcaatg aaacatccga tgttctttca gataagaccc atggcttcga tgctgatacc      960
atcatcaaag ctacatgtat gacgatggtt ttaggaggga gtgatacgac ggcggtggtt     1020
gtgatatggg caatctcgct gctgctgaat aatcgccctg cgttgagaaa agtgcaagaa     1080
gaactggaag cccatatcgg ccgagacaga gaactggagg aatcggatct cggtaagcta     1140
gtgtatttgc aggcagtcgt gaaggagaca ttgcggctgt acggagccgg aggccttttc     1200
tttcgtgaaa ccacagagga tgtcaccatc gacggattcc atgtcgagaa agggacatgg     1260
ctgttcgtga acgtggggaa gatccacaga gatgggaagg tgtggccgga gccaacggag     1320
ttcaaaccgg agaggtttct gacgacccac aaagattttg atctgaaggg ccagcggttt     1380
gagctcatcc ctttcggggg aggaagaaga tcgtgccctg gaatgtcttt gggctccaa      1440 atgctacagc ttattttggg taaactgctt caggcttttg atatatcgac gccggggac      1500 gccgccgttg atatgaccgg atccattgga ctgacgaaca tgaaagccac tccattggaa     1560
gtgctcatca ccccgcgctt gcctctttcg ctttacgatt ga                         1602

<210> SEQ ID NO 7
<211> LENGTH: 1236
<212> TYPE: DNA
<213> ORGANISM: Siraitia grosvenorii

<400> SEQUENCE: 7
atggagactc ttcttcttca tcttcaatcg ttatttcatc caatttcctt cactggtttc       60
gttgtcctct ttagcttcct gttcctgctc cagaaatggt tactgacacg tccaaaactct     120 tcatcagaag cctcaccccc ttctccacca aagcttccca tcttcggaca ccttctaaac      180
ctgggtctgc atcccacat cacccctcgga gcctacgctc gccgctatgg ccctctcttc      240
ctcctccact tcggcagcaa gcccaccatc gtcgtctctt ctgccgaaat cgctcgcgat      300
atcatgaaga cccacgacct cgtcttcgcc aaccgtccta aatcaagcat cagcgaaaag      360
attctttacg gctccaaaga tttagccgca tctccttacg gcgaatactg gaggcagatg      420
aaaagcgttg gcgtgcttca tcttttgagc aacaaaaggg ttcaatcctt tcgctctgtc      480
agagaagaag aagtcgaact gatgatccag aagatccaac agaacccccct atcagttaat      540 ttaagcgaaa tattctctgg actgacgaac gacatagttt gcagggtggc tttagggaga      600
```

```
aagtatggcg tgggagaaga cggaaagaag ttccggtctc ttctgctgga gtttggggaa      660
gtattgggaa gtttcagtac gagagacttc atcccgtggc tgggttggat tgatcgtatc      720
agtgggctgg acgccaaagc cgagagggta gccaaagagc tcgatgcttt ctttgacaga      780
gtgatcgaag atcacatcca tctaaacaag agagagaata atcccgatga gcagaaggac      840
ttggtggatg tgctgctttg tgtacagaga gaagactcca tcgggtttcc ccttgagatg      900
gatagcataa aagctttaat cttggacatg tttgctgcag gcacagacac gacatacacg      960
gtgttggagt gggcaatgtc ccaactgttg agacacccag aagcgatgaa gaaactgcag     1020
agggaggtca gagaaatagc aggtgagaaa gaacacgtaa gtgaggatga tttagaaaag     1080
atgcattact tgaaggcagt aatcaaagaa acgctgcggc tacacccacc aatcccactc     1140
ctcgtcccca gagaatcaac ccaagacatc aggttgaggg ggtacgatat cagaggcggc     1200
acccgggtta tgatcaatgc atgggccatc ggaaga                              1236

<210> SEQ ID NO 8
<211> LENGTH: 1614
<212> TYPE: DNA
<213> ORGANISM: Siraitia grosvenorii

<400> SEQUENCE: 8
atgtcgatga gtagtgaaat tgaaagcctc tgggttttcg cgctggcttc taaatgctct       60
gctttaacta aagaaaacat cctctggtct ttactcttct ttttcctaat ctgggtttct      120
gtttccattc tccactgggc ccatccgggc ggcccggctt ggggccgcta ctggtggcgc      180
cgccgccgca gcaattccac cgccgctgct attcccggcc cgagaggcct ccccctcgtc      240
ggcagcatgg gcttgatggc cgacttggcc caccaccgga ttgccgccgt ggctgactcc      300
ttaaacgcca cccgcctcat ggccttttcg ctcggcgaca ctcgcgtgat cgtcacatgc      360
aaccccgacg tcgccaaaga gattctcaac agctccctct tcgccgaccg ccccgttaag      420
gagtccgctt actccttgat gttcaaccgc gccattgggt tcgcccccta tggcctttac      480
tggcggaccc tccgccgcat cgcttcccac cacctcttct gccccaagca aatcaagtcc      540
tcccagtccc agcgccgcca aatcgcttcc caaatggtcg caatgttcgc aaaccgcgat      600
gccacacaga gcctctgcgt tcgcgactct ctcaagcggg cttctctcaa caacatgatg      660
ggctctgttt tcgccgagt ttacgacctc tctgactcgg ctaacaatga cgtccaagaa      720
ctccagagcc tcgtcgacga aggctacgac ttgctgggcc tcctcaactg gtccgaccat      780
ctcccatggc tcgccgactt cgactctcag aaaatccggt tcagatgctc ccgactcgtc      840
cccaaggtga accacttcgt cggccggatc atcgccgaac accgcgccaa atccgacaac      900
caagtcctag atttcgtcga cgttttgctc tctctccaag aagccgacaa actctctgac      960
tccgatatga tcgccgttct ttgggaaatg attttttcgtg gaacggacac ggtggcagtt     1020
ttaatcgagt ggatactggc caggatggta cttcacaacg atatccaaag gaaagttcaa     1080
gaggagctag ataacgtggt tgggagtaca cgcgccgtcg cggaatccga cattccgtcg     1140
ctggtgtatc taacggctgt ggttaaggaa gttctgaggt tacatccgcc gggcccactc     1200
ctgtcgtggg cccgcctagc catcactgat acaatcatcg atgggcatca cgtgcccgg     1260 gggaccaccg ctatggttaa catgtggtcg atagcgcggg acccacaggt ctggtcggac     1320
ccactcgaat ttatgcccca gaggtttgtg tccgaccccg tgacgtggat gttctcggtc     1380
atgggttcgg atctccggct ggctccgttc gggtcgggca gaaggacctg ccccgggaag     1440
```

| gccttcgcct | ggacaactgt | caccttctgg | gtggccacgc | ttttacacga | cttcaaatgg | 1500 |
| tcgccgtccg | atcaaaacga | cgccgtcgac | ttgtcggagg | tcctcaagct | ctcctgcgag | 1560 |
| atggccaatc | ccctcaccgt | taaagtacac | ccaaggcgca | gtttaagctt | ttaa | 1614 |

<210> SEQ ID NO 9
<211> LENGTH: 1506
<212> TYPE: DNA
<213> ORGANISM: Siraitia grosvenorii

<400> SEQUENCE: 9

| atggatggtt | ttcttccaac | agtggcggcg | agcgtgcctg | tgggagtggg | tgcaatattg | 60 |
| ttcacggcgt | tgtgcgtcgt | cgtgggaggg | gttttggttt | atttctatgg | accttactgg | 120 |
| ggagtgagaa | gggtgcctgg | tccaccagct | attccactgg | tcggacatct | tcccttgctg | 180 |
| gctaagtacg | gcccagacgt | tttctctgtc | cttgccaccc | aatatggccc | tatcttcagg | 240 |
| ttccatatgg | gtaggcagcc | attgataatt | atagcagacc | ctgagctttg | taaagaagct | 300 |
| ggtattaaga | aattcaagga | catcccaaat | agaagtgtcc | cttctccaat | atcagcttcc | 360 |
| cctcttcatc | agaagggtct | tttcttcaca | agggatgcaa | gatggtcgac | aatgcggaac | 420 |
| acgatattat | cggtctatca | gtcctcccat | ctagcgagac | taatacctac | tatgcaatca | 480 |
| atcattgaaa | ctgcaactca | aaatctccat | tcctctgtcc | aggaagacat | ccctttctcc | 540 |
| aatctctccc | tcaaattgac | caccgatgtg | attggaacag | cagccttcgg | tgtcaacttt | 600 |
| gggctctcta | atccacaggc | aaccaaaact | tgtgctacca | acggccaaga | caacaaaaat | 660 |
| gacgaagttt | cagacttcat | caatcaacac | atctactcca | caacgcagct | caagatggat | 720 |
| ttatcaggtt | ccttctcaat | catacttgga | ctgcttgtcc | ctatactcca | agaaccattt | 780 |
| agacaagtcc | taaagagaat | accattcacc | atggactgga | agtgaccg | gacaaatcag | 840 |
| aaattaagtg | gtcggcttaa | tgagattgtg | gagaagagaa | tgaagtgtaa | cgatcaaggt | 900 |
| tcaaaagact | tcttatcgct | cattttgaga | gcaagagagt | cagagacagt | atcaaggaat | 960 |
| gtcttcactc | cagactacat | cagtgcagtt | acgtatgaac | acctacttgc | tgggtcggct | 1020 |
| accacggcgt | ttacgttgtc | ttctattgta | tatttagttg | ctgggcatcc | agaagtcgag | 1080 |
| aagaagttgc | tagaagagat | tgacaacttt | ggtccatccg | atcagatacc | aacagctaat | 1140 |
| gatcttcatc | agaagtttcc | atatcttgat | caggtgatta | agagggctat | gaggttctac | 1200 |
| actgttcccc | ctctagtagc | cagagaaaca | gctaaagatg | tggagattgg | tggatatctt | 1260 |
| cttccaaagg | ggacatgggt | ttggttagca | cttggagttc | ttgccaagga | tccaaagaac | 1320 |
| tttccagaac | cagataaatt | caaaccagag | aggtttgatc | caaatgaaga | agaggagaaa | 1380 |
| caaaggcatc | cttatgcttt | aatccccttt | ggaattggtc | ctcgagcatg | cattggtaaa | 1440 |
| aaattcgccc | ttcaggagtt | gaagctctcg | ttgattcatt | tgtacaggaa | gtttgtattt | 1500 |
| cggcat | | | | | | 1506 |

<210> SEQ ID NO 10
<211> LENGTH: 1566
<212> TYPE: DNA
<213> ORGANISM: Siraitia grosvenorii

<400> SEQUENCE: 10

| atggaaatca | ttttatcata | tctcaacagc | tccatagctg | gactcttcct | cttgcttctc | 60 |
| ttctcgtttt | ttgttttgaa | aaaggctaga | acctgtaaac | gcagacagcc | tcctgaagca | 120 |
| gccggcggat | ggccgatcat | cggccacctg | agactgctcg | ggggttcgca | acttccccat | 180 |

```
gaaaccttgg gagccatggc cgacaagtat ggaccaatct tcagcatccg agttggtgtc    240
cacccatctc ttgttataag cagttgggaa gtggctaaag agtgctacac cacccctcgac   300 tcagttgtct cttctcgtcc caagagtttg ggtggaaagt tgttgggcta caacttcgcc    360
gcttttgggt tcaggcctta tgattccttt taccggagta tccgcaaaac catagcctcc    420
gaggtgctgt cgaaccgccg tctggagttg cagagacaca ttcgagtttc tgaggtgaag    480
agatcggtga aggagcttta caatctgtgg acgcagagag aggaaggctc agaccacata    540
cttattgatg cggatgaatg gattggtaat attaatttga acgtgattct gatgatggtt    600
tgtgggaagc ggtttcttgg cggttctgcc agcgatgaga aggagatgag gcggtgtctc    660
aaagtctcga gagatttctt cgatttgaca gggcagttta cggtgggaga tgccattcct    720
ttcctgcgat ggctggattt gggtggatat gcgaaggcga tgaagaaaac tgcaaaagaa    780
atggactgtc tcgttgagga atggctggaa gaacaccgcc ggaagagaga ctccggcgcc    840
accgacggtg aacgtgactt catggatgtg atgctttcga ttcttgaaga gatggacctt    900
gctggctacg acgctgacac agtcaacaaa gccacatgcc tgagcattat ttctggggga    960
atcgatacta taacgctaac tctgacatgg gcgatctcgt tattgctgaa caatcgagag   1020
gcactgcgaa gggttcaaga ggaggtggac atccatgtcg gaaacaaaag gcttgtggat   1080
gaatcagact tgagcaagct ggtgtatctc caagccgtcg tgaaagagac attaaggttg   1140
tacccagcag ggccgctgtc gggagctcga gagttcagtc gggactgcac ggtcggaggg   1200
tatgacgtgg ccgccggcac acggctcatc acaaaccttt ggaagataca gacggaccct   1260
cgggtgtggc cggagccact tgagttcagg ccggagaggt ttctgagcag ccaccagcag   1320
ttggatgtga agggccagaa ctttgaactg gcccccatttg gttgtggaag aagagtgtgc   1380
cctggggcgg ggcttggggt tcagatgacg cagttggtgc tggcgagtct gattcattcg   1440
gtggaacttg gaactcgctc cgatgaagcg gtggacatgg ctgctaagtt tggactcaca   1500
atgtacagag ccacccctct tcaggctctc gtcaagccac gcctccaagc cggtgcttat   1560
tcatga                                                              1566
```

<210> SEQ ID NO 11
<211> LENGTH: 1425
<212> TYPE: DNA
<213> ORGANISM: Siraitia grosvenorii

<400> SEQUENCE: 11

```
atgggtgtat tgtccatttt attattcaga tattccgtca agaagaagcc attaagatgc     60
ggtcacgatc aaagaagtac cacagatagt ccacctggtt caagaggttt gccattgata    120
ggtgaaactt tgcaattcat ggctgctatt aattctttga acggtgtata cgatttcgtt    180
agaataagat gtttgagata cggtagatgc tttaagacaa gaatcttcgg tgaaacccat    240 gttttttgtct caactacaga atccgctaag ttgatcttga aggatggtgg tgaaaaattc    300
accaaaaagt acatcagatc aatcgctgaa ttggttggtg acagaagttt gttatgtgca    360
tctcatttgc aacacaagag attgagaggt tgttgactaa atttgttttc tgccacattc    420
ttggcttctt tcgtaactca attcgatgaa caaatcgttg aagcttttag atcatgggaa    480
tccggtagta ccataatcgt tttgaacgaa gcattgaaga tcacttgtaa ggccatgtgc    540
aaaatggtca tgtccttaga aagagaaaac gaattggaag ctttgcaaaa ggaattgggt    600
catgtttgtg aagctatgtt ggcatttcca tgcagattcc ctggtacaag atttcacaat    660
```

-continued

```
ggtttgaagg caagaagaag aatcattaaa gttgtcgaaa tggccattag agaaagaaga    720
agatctgaag ctcctagaga agatttcttg caaagattgt tgacagaaga aaaggaagaa    780
gaagacggtg gtggtgtttt aagtgatgcc gaaattggtg acaacatatt gacaatgatg    840
atcgcaggtc aagataccac tgcctctgct attacctgga tggtcaagtt tttggaagaa    900
aaccaagatg tattgcaaaa cttaagagac gaacaattcg aaatcatggg taaacaagaa    960
ggttgtggtt catgcttctt gacattagaa gatttgggta atatgtccta tggtgcaaaa   1020
gtagttaagg aatcattgag attagcctcc gtcgtaccat ggtttcctag attggtttta   1080
caagattctt tgatccaagg ttacaaaatt aaaaagggt tggaacgtcaa catagacgta   1140
agatctttac attcagatcc atccttgtat aatgacccaa caaagtttaa ccctagtaga   1200
ttcgatgacg aagctaaacc ttactcattt ttggcattcg gtatgggtgg tagacaatgt   1260
ttgggtatga acatggcaaa ggccatgatg ttggttttct tgcacagatt ggtcacctca   1320
ttcagatgga aggttataga ttccgactct tcaatcgaaa aatgggcttt gttctctaag   1380
ttgaagtcag gttgccctat cgtagttacc cacatcggtt cctaa                   1425
```

<210> SEQ ID NO 12
<211> LENGTH: 1509
<212> TYPE: DNA
<213> ORGANISM: Siraitia grosvenorii

<400> SEQUENCE: 12

```
atggatttct actggatctg tgttcttctg ctttgcttcg catggttttc cattttatcc     60
cttcactcga gaacaaacag cagcggcact tccaaacttc ctcccggacc gaaacccttg    120
ccgatcatcg gaagcctttt ggctctcggc cacgagcccc acaagtcttt ggctaatctc    180
gctaaatctc atgccctct tatgacctta aagctcggcc aaatcaccac cgtcgtagtt    240
tcctccgctg ccatggctaa gcaagttctc caaacgcacg accagtttct gtccagcagg    300
accgttccag acgcaatgac ctctcacaac cacgatgctt tcgcactccc atggattccg    360
gtttcacccc tctggcgaaa ccttcgacga atatgcaaca accagttgtt tgccggcaag    420
attctcgacg ccaacgagaa tctccggcga accaaagtgg ccgagctcgt atccgatatc    480
tcgagaagtg cattgaaagg tgagatggtg gattttggaa acgtggtgtt cgtcacttcg    540
ctcaatctgc tttccaatac gattttctcg gtggatttct tcgacccaaa ttctgaaatt    600
gggaaagagt tcaggcacgc agtacgaggc ctcatggaag aagctgccaa accaaatttg    660
ggggattatt ccctctgct gaagaagata gatcttcaag gaataaagag gagacagacc    720
acttacttcg atcgggtttt taatgttttg gagcacatga tcgaccagcg tcttcagcag    780
cagaagacga cgtctggttc tacctccaac aacaacaacg acttactgca ctaccttctc    840
aacctcagca acgaaaatag cgacatgaaa ttggggaaac ttgagctgaa acacttctta    900
ttggtgctat tcgtcgctgg gactgaaacg agttctgcaa cactgcaatg gcaatggca    960
gaactactaa gaaacccaga aaagttagca aaagctcaag cggagaccag gcgggtgatt   1020
gggaaaggga acccaattga gaatcagac atttcgaggc tgccttatct gcaagcagtg   1080
gtgaaagaaa ctttcagatt gcacacacca gcgccatttc tactgccgcg caaagcacta   1140
caggacgtgg aaattgcagg tttcacagtc ccaaaggacg ctcaggtact ggtaaattta   1200
tgggctatga gcagagattc aagcatctgg gagaacccag agtggttcga gccagaaagg   1260
ttttggagt cggagctgga cgttagaggg agagattttg agctgatccc gttcggcggt   1320
gggcggagga tttgccccgg tctgccgttg gcgatgagaa tgttgcattt gatttgggt   1380
```

-continued

| | |
|---|---|
| tctctcatcc acttctttga ttggaagctt gaagatgggt gtcggccgga agacgtgaaa | 1440 |
| atggacgaaa agcttggcct cactctggag ttggcttttc ccctcacagc cttgcctgtc | 1500 |
| cttgtctaa | 1509 |

<210> SEQ ID NO 13
<211> LENGTH: 1734
<212> TYPE: DNA
<213> ORGANISM: Siraitia grosvenorii

<400> SEQUENCE: 13

| | |
|---|---|
| atgtcctcct gcggtggtcc aactcctttg aatgttatcg gtatcttatt acaatcagaa | 60 |
| tcctccagag cctgcaactc agacgaaaac tcaagaattt tgagagattt cgtaacaaga | 120 |
| gaagttaacg ctttcttatg gttgtccttg atcactatca cagcagtttt gatcagtaaa | 180 |
| gttgtcggtt tgtttagatt gtggtctaag gcaaagcaat tgagaggtcc accttgtcca | 240 |
| tcattctacg gtcattctaa gatcatctca agacaaaatt tgactgattt gttatatgac | 300 |
| tcccacaaaa agtacggtcc agtagttaaa ttgtggttag gtcctatgca attgttagtc | 360 |
| tccgtaaagg aaccaagttt gttgaaggaa atattggtta aagctgagga taagttgcct | 420 |
| ttaacaggta gagcctttag attggctttc ggtagatctt cattatttgc atccagtttc | 480 |
| gaaaaggttc aaaacagaag acaaagattg gccgaaaagt tgaataagat cgcattccaa | 540 |
| agagccaaca tcattccaga aaaggccgta gcttgtttca tgggtagagt tcaagatttg | 600 |
| atgatagaag aatctgtcga ctgtaataag gtttctcaac attggctttt tacttttgtta | 660 |
| ggttgcacat tgtttggtga cgccttctta ggttggtcta aggctacaat ctatgaagaa | 720 |
| ttgttgatga tgatcgctaa ggacgcatcc ttttgggcta gttatagagt taccccaatc | 780 |
| tggaagcaag gtttctggag ataccaagaa ttgtgtatga agttgaagtg cttgactcaa | 840 |
| gatatcgttc aacaatacag aaagcattac aagttgtttt ctcactcaca aaaccaaaac | 900 |
| ttacacaacg aaaccaagtc aactggtgtt gaagtcgctt ttgatattcc accttgtcct | 960 |
| gctgcagacg ttagaaaattc ttgctttttc tacggtttga acgatcatgt taacccaaac | 1020 |
| gaagaacctt gtggtaatat tatgggtgtc atgtttcacg gttgcttgac tacaacctct | 1080 |
| ttgatcgcat caatcttgga agattggcc actaacccag aaatccaaga aagattaat | 1140 |
| tctgaattga acttagttca aaagggtcca gtcaaggatc atagaaagaa tgttgacaac | 1200 |
| atgcctttgt tattggcaac aatctatgaa tcagctagat tattgccagc aggtcctta | 1260 |
| ttgcaaagat gtccttttgaa gcaagatttg gttttgaaaa caggtatcac cattccagct | 1320 |
| ggtaccttgg tcgtagttcc tattaaattg gttcaaatgg atgactcttc atggggttca | 1380 |
| gatgccaatg agtttaatcc atacagattc ttgtccatgg cttgtaatgg tattgacatg | 1440 |
| atacaaagaa cccctttagc tggtgaaaac attggtgacc aaggtgaagg ttcatttgtc | 1500 |
| ttgaatgacc caattggtaa cgtaggtttc ttaccttttg gtttcggtgc aagagcctgc | 1560 |
| gttggtcaaa agtttataat ccaaggtgtc gctactttgt tcgcaagttt gttggcccat | 1620 |
| tacgaaatta aattgcaatc cgagagtaag aatgattcta aaccatccag taacacctct | 1680 |
| gccagtcaaa tcgtcccaaa ctcaaaaatc gtattcgtaa gaagaaactc ataa | 1734 |

<210> SEQ ID NO 14
<211> LENGTH: 1422
<212> TYPE: DNA
<213> ORGANISM: Siraitia grosvenorii

<400> SEQUENCE: 14

```
atgtggactg tcgtgctcgg tttggcgacg ctgtttgtcg cctactacat ccattggatt    60
aacaaatgga gagattccaa gttcaacgga gttctgccgc cgggcaccat gggtttgccg   120
ctcatcggag agacgattca actgagtcga cccagtgact ccctcgacgt tcacccttc    180
atccagaaaa aagttgaaag tacgggccg atcttcaaaa catgtctggc cggaaggccg    240
gtggtggtgt cggcggacgc agagttcaac aactacataa tgctgcagga aggaagagca   300
gtggaaatgt ggtatttgga tacgctctcc aaattttcg gcctcgacac cgagtggctc    360
aaagctctgg gcctcatcca caagtacatc agaagcatta ctctcaatca cttcggcgcc   420
gaggccctgc gggagagatt tcttcctttt attgaagcat cctccatgga agcccttcac   480
tcctggtcta ctcaacctag cgtcgaagtc aaaaatgcct ccgctctcat ggttttagg    540
acctcggtga ataagatgtt cggtgaggat gcgaagaagc tatcgggaaa tatccctggg   600
aagttcacga agcttctagg aggatttctc agtttaccac tgaattttcc cggcaccacc   660
taccacaaat gcttgaagga tatgaaggaa atccagaaga agctaagaga ggttgtagac   720
gatagattgg ctaatgtggg ccctgatgtg aagatttct ggggcaagc ccttaaagat     780
aaggaatcag agaagttcat ttcagaggag ttcatcatcc aactgttgtt ttctatcagt   840
tttgctagct ttgagtccat ctccaccact cttactttga ttctcaagct ccttgatgaa   900
cacccagaag tagtgaaaga gttggaagct gaacacgagg cgattcgaaa agctagagca   960
gatccagatg gaccaattac ttgggaagaa tacaaatcca tgactttac attacaagtc   1020
atcaatgaaa ccctaaggtt ggggagtgtc acacctgcct tgttgaggaa aacagttaaa   1080
gatcttcaag taaaaggata cataatcccg gaaggatgga caataatgct tgtcaccgct   1140
tcacgtcaca gagacccaaa agtctataag gaccctcata tcttcaatcc atggcgttgg   1200
aaggacttgg actcaattac catccaaaag aacttcatgc cttttggggg aggcttaagg   1260
cattgtgctg gtgctgagta ctctaaagtc tacttgtgca ccttcttgca catcctctgt   1320
accaaatacc gatggaccaa acttggggga ggaaggattg caagagctca tatattgagt   1380
tttgaagatg ggttacatgt gaagttcaca cccaaggaat ga                      1422
```

<210> SEQ ID NO 15
<211> LENGTH: 1374
<212> TYPE: DNA
<213> ORGANISM: Siraitia grosvenorii

<400> SEQUENCE: 15

```
atgaagatga agatggaatc catgcgcacc tccctggata tctccgacca tgacatactt    60
ccaagggttt atcctcatgt tcacctatgg atcaacaaat atgggaaaaa cttcattcag   120
tggaatggca acgtagctca gttgattgtt tcggatcctg acacgatcaa ggagatactc   180
caaaaccgag aacaagctgt tcccaaaata gatctcagcg agatgcacg gaggatattc    240
gggaatgggc tttcgacttc tgacggtgaa aaatgggcta aggctcgaag aatcgctgat   300
tacgctttcc acggggatct cctaagaaat atggggccaa ccatggtttc ctgtgctgag   360
gcaatggtgg aaaagtggaa gcatcatcaa ggcaaagagc ttgatttgtt cgaagagttt   420
aaggtgctca cttcagatat cattgcacat acagcctttg gaagcagtta tttggaaggg   480
aaagttattt ttcagactct aagtaagctg agcatgatat tatttaagaa tcagttcaaa   540
cgaaggattc ctgttatcag caagttcttc agatcaaagg atgcgaggga gggagaggag   600
ctggaaagaa ggttgaaaaa ttccataatt tcaataatgg aaaagagaga agagaaggtg   660
```

```
ataagtggtg aagcagataa ctatggtaat gattttcttg gattacttt  gaaggcaaag    720 aatgagcctg accagaggca gaggatttct gttgatgatg tagtggatga atgcaaaaca    780
gtttacttcg ctgggcaaga aactacaagt gttttgcttg cttggaccgc ctttctttta    840
gcaactcatg agcattggca agaagaagca agaaaggaag tgctgaatat gtttggcaac    900
aagaatccaa ctttagaagg catcacaaaa ttaaagatta tgagcatgat catcaaggaa    960
tctctaagat tatatcctcc agccccgccc atgtcaagga aggttaaaaa ggaagtcaga   1020
ttggggaagc tggttctccc ccccaacatt caagtaagca tctcaactat tgcagttcat   1080
catgatactg caatatgggg tgaagatgcc catgtattca aaccagaaag attttctgaa   1140
ggaacagcta agatatccc atcagctgca tacatcccat ttggctttgg tcctcgaaac    1200
tgcatcggca atatcttggc catcaacgaa actaagattg cactgtcgat gattctacaa   1260
cgattttctt tcaccatctc cccggcctac gtccacgcac ctttccagtt cctcactatc   1320
tgcccccaac acggggttca ggtaaagctt cagtccctat taagtgaaag gtga         1374

<210> SEQ ID NO 16
<211> LENGTH: 1590
<212> TYPE: DNA
<213> ORGANISM: Siraitia grosvenorii

<400> SEQUENCE: 16
atggaagctg aatttggtgc cggtgctact atggtattat ccgttgtcgc aatcgtcttc     60
tttttcacat ttttacactt gtttgaatct ttctttttga agccagatag attgagatct    120
aagttgagaa agcaaggtat tggtggtcca tctccttcat ttttgttggg taatttgtca    180
gaaattaaat ccatcagagc tttgtcttca caagctaaga acgcagaaga tgcctctgct    240
ggtggtggtg gtggttccgc cagtatagct catggttgga cttcaaattt gtttcctcac    300
ttagaacaat ggagaaacag atatggtcca attttcgtat actccagtgg tacaatccaa    360
atcttgtgta tcacagaaat ggaaaccgtt aaggaaatct ctttgtcaac ctccttgagt    420
ttaggtaaac ctgctcattt gtctaaggat agaggtccat tgttaggttt gggtatctta    480
gcctcttcag gtcctatttg ggttcaccaa agaaagatca tcgctccaca attgtatttg    540
gataaagtaa agggtatgac ctcattgatg gttgaaagtg caaattctat gttaagatcc    600
tgggaaacta aagttgaaaa tcatggtggt caagccgaaa ttaacgtcga tggtgacttg    660
agagcattaa gtgccgatat catttctaag gcttgctttg gttcaaacta ttccgaaggt    720
gaagaaattt tcttgaagtt gagagcattg caagttgtca tgagtaaggg ttctattggt    780
atacctggtt ttagatacat accaactaaa aataacagag aaatgtggaa gttggaaaag    840
gaaatcgaat caatgatctt gaaggttgcc aacgaaagaa cacaacattc cagtcacgaa    900
caagatttgt tgcaaatgat tttggaaggt gcaaagtctt gggtgaaga caataagagt    960 atgaacatat caagagacaa gtttattgtt gacaattgta agaacatcta tttcgctggt   1020
catgaaacta cagctataac cgcatcttgg tgcttgatgt tgttagctgc acaccctgat   1080
tggcaagcaa gagccagatc tgaagtttta caatgttgcg atgacagacc aatcgatgca   1140
gacacagtca aaaatatgaa gaccttgact atggtaattc aagaaacttt gagattgtac   1200
ccacctgctg tattcgttac aagacaagca ttagaagata tcagattcaa aaacatcaca   1260
ataccaaagg gtatgaactt tcatatacca atccctatgt gcaacaaga  cttccactta   1320 tggggtcctg atgcttgttc atttgaccca caaagattct ccaatggtgt cttaggtgca   1380
```

```
tgcaaaaacc cacaagccta tatgccttt gtgttggtc caagagtctg tgccggtcaa    1440
catttcgcta tgatcgaatt gaaagtcatc gtatcattgg ttttgtccag attcgaattt   1500
tctttgtcac cttcctacaa gcattcacca gccttcagat tagttgtcga accagaaaac   1560
ggtgtcatat tgcatgtcag aaagttgtga                                    1590

<210> SEQ ID NO 17
<211> LENGTH: 1554
<212> TYPE: DNA
<213> ORGANISM: Siraitia grosvenorii

<400> SEQUENCE: 17
atggaagtgg atatcaatat cttcaccgtc ttttccttcg tattatgcac agtcttcctc     60
ttctttctat ccttcttgat cctcctcctc ctccgaacgc tcgccggaaa atccataacg    120
agctccgagt acacgccagt gtacggcacc gtctacggtc aggctttcta tttcaacaac   180
ctgtacgatc atctaacgga ggtgccaag agacatcgaa ccttccggct gcttgcgccg    240
gcatacagcg agatatacac gaccgatccg agaaacatcg agcatatgtt gaagacgaaa    300
ttcgataagt attcgaaagg aagcaaggat caagaaatcg ttggggatct gtttggagag   360
gggatatttg cagtcgatgg agataagtgg aagcagcaga ggaagctggc tagctatgaa    420
ttctcgacga ggattcttag ggattttagc tgctcggttt tcagacgaag tgctgctaaa    480
cttgttggag ttgtttcgga gttttccagc atgggtcggg ttttgatat ccaggatttg     540 ctaatgcggt gcgctttgga ctccattttc aaagtggggt tcggggttga tttgaattgc    600
ttggaggaat caagcaaaga agggagcgat tcatgaaag ccttcgatga ttctagcgct     660 cagattttt ggcgctatat cgatcccttc tggaaattga agagattgct taacatcggt     720
tccgaagctt cgtttaggaa caacataaaa accatagatg cttttgtgca ccagttgatc    780
agagacaaga gaaaattgct tcagcaaccg aatcacaaga atgacaaaga ggacatactt    840
tggaggtttc tgatggaaag tgagaaggat ccaacaagaa tgaatgatca atatctaagg    900
gatatagtcc tcaatttcat gttggctggc aaagattcaa gtggaggaac tctgtcctgg    960
ttcttctaca tgctatgcaa gaacccttta atacaggaaa aagttgcaga gaagtgagg    1020 caaattgttg cgtttgaagg ggaagaagtt gacatcaatt tgttcataca aaacttaact   1080
gattcagctc ttgacaaaat gcattatctt catgcagcat tgaccgagac tctgaggcta   1140
tatcctgcag tccctttgga tggaaggact gcagaaatag atgacattct tcctgatggc   1200
tataaactaa gaaaaggga tggagtatac tacatggcct attccatggg caggatgtcc   1260
tccctttggg gagaagatgc tgaagatttt aaacccgaaa gatggcttga agtggaact   1320 tttcaacccg aatcaccttt caattcatc gcttttcatg cgggtcctcg aatgtgtttg    1380 ggaaagagt ttgcttatcg acaaatgaag atagtatctg ctgctttgct tcaattttt     1440 cgattcaaag tagctgatac aacgaggaat gtgacttata ggatcatgct taccttcac    1500 attgatggag gtctccctct tcttgcaatt ccgagaatta gaaaatttac ctaa          1554

<210> SEQ ID NO 18
<211> LENGTH: 1686
<212> TYPE: DNA
<213> ORGANISM: Siraitia grosvenorii

<400> SEQUENCE: 18
ttggatagtg gagttaaaag agtgaaacgg ctagttgaag agaaacggcg agcagaattg     60
tctgcccgga ttgcctctgg agaattcaca gtcgaaaaag ctggttttcc atctgtattg   120
```

```
aggagtggct tatcaaagat gggtgttccc agtgagattc tggacatatt atttggtttc      180
gttgatgctc aagaagaata tcccaagatt cccgaagcaa aaggatcagt aaatgcaatt      240
cgtagtgagg ccttcttcat acctctctat gagctttatc tcacatatgg tggaatattt      300
aggttgactt ttgggccaaa gtcattcttg atagttctg atccttccat tgctaaacat       360
atactgaagg ataatccgag gaattattct aagggtatct tagctgaaat tctagagttt      420
gtcatgggga agggacttat accagctgac gagaagatat ggcgtgtacg aaggcgggct      480
atagtcccat ctttgcatct gaagtatgta ggtgctatga ttaatctttt tggagaagct      540
gcagataggc tttgcaagaa gctagatgct gcagcatctg atggggttga tgtggaaatg      600
gagtccctgt tctcccgttt gactttagat atcattggca aggcagtttt taactatgac      660
tttgattcac ttacaaatga cactggcata gttgaggctg tttacactgt gctaagagaa      720
gcagaggatc gcagtgttgc accaattcca gtatgggaaa ttccaatttg aaggatatt      780 tcaccacggc aaaaaaaggt ctctaaagcc ctcaaattga tcaacgacac cctcgatcaa      840
ctaattgcta tatgcaagag gatggttgat gaggaggagc tgcagtttca tgaggaatac      900
atgaatgagc aagatccaag catccttcat ttccttttgg catcaggaga tgatgtttca      960
agcaagcagc ttcgtgatga cttgatgact atgcttatag ctgggcatga aacatctgct     1020
gcagttttaa catggacctt ttatcttctt tccaaggagc cgaggatcat gtccaagctc     1080
caggaggagg ttgattcagt ccttggggat cggtttccaa ctattgaaga tatgaagaac     1140
ctcaaatatg ccacacgaat aattaacgaa tccttgaggc tttacccaca gccaccagtt     1200
ttaatacgtc gatctcttga caatgatatg ctcgggaagt acccccattaa aaagggtgag    1260 gacatattca tttctgtttg gaacttgcat cgcagtccaa aactctggga tgatgcggat     1320
aaatttaatc ctgaaaggtg gcctctggat ggacccaatc caaatgagac aaatcaaaat     1380
ttcagatatt tacctttgg tggcggacca cggaaatgtg tgggagacat gtttgcttcg     1440
tacgagactg ttgtagcact tgcaatgctt gttcggcgat ttgacttcca aatggcactt     1500
ggagcacctc ctgtaaaaat gacaactgga gctacaattc acacaacaga tggattgaaa     1560
atgacagtta cacgaagaat gagacctcca atcatacca cattagagat gcctgcagtg      1620
gtcgttgact cgtctgtcgt ggactcgtcc gtcgccattt tgaaagaaga aacacaaatt     1680
ggttag                                                                1686

<210> SEQ ID NO 19
<211> LENGTH: 1299
<212> TYPE: DNA
<213> ORGANISM: Siraitia grosvenorii

<400> SEQUENCE: 19
cagttcctct cctggtcctc ccagtttggc aagaggttca tcttctggaa tgggatcgag       60
cccagaatgt gcctcaccga gaccgatttg atcaaagagc ttctctctaa gtacagcgcc      120
gtctccggta agtcatggct tcagcaacag ggctccaagc acttcatcgg ccgcggtctc      180
ttaatggcca acggccaaaa ctggtaccac cagcgtcaca tcgtcgcgcc ggccttcatg      240
ggagacagac tcaagagtta cgccgggtac atggtgaatg cacaaaagga gatgcttcag      300
tcaattgaaa acgaggtcaa ctcggggcga tccgagttcg aaatcggtga gtatatgacc      360
agactcaccg ccgatataat atcacgaacc gagttcgaaa gcagctacga aagggaaag       420 caaattttcc atttgctcac cgtttttacag catctctgcg ctcaggcgag ccgccacctc      480
```

```
tgccttcctg aagccggtt ttttccgagt aaatacaaca gagagataaa ggcattgaag    540
acgaaggtgg aggggttgtt aatggagata atacagagca gaagagactg tgtggaggtg    600
gggaggagca gttcgtatgg aaatgatctg ttgggaatgt tgctgaatga gatgcagaag    660
aagaaagatg ggaatgggtt gagcttgaat ttgcagatta taatggatga atgcaagacc    720
ttcttcttcg ccggccatga aaccactgct cttttgctca cttggactgt aatgttattg    780
gccagcaacc cttcttggca acacaaggtt cgagccgaag ttatggccgt ctgcaatgga    840
ggaactctct ctcttgaaca tctctccaag ctctctctgt tgagtatggt gataaatgaa    900
tcgttgaggc tatacccgcc agcaagtatt cttccaagaa tggcatttga agatataaag    960
ctgggagatc ttgagatccc aaaagggctg tcgatatgga tcccagtgct tgcaattcac   1020
cacagtgaag agctatgggg caaagatgca aatgagttca acccagaaag atttgcaaat   1080
tcaaaagcct tcacttcggg gagattcatt ccctttgctt ctggccctcg caactgcgtt   1140
ggccaatcat ttgctctcat ggaaaccaag atcattttgg ctatgctcat ctccaagttt   1200
tccttcacca tctctgacaa ttatcgccat gcacccgtgg tcgtcctcac tataaaaccc   1260
aaatacggag tccaagtttg cttgaagcct ttcaattaa                          1299

<210> SEQ ID NO 20
<211> LENGTH: 1506
<212> TYPE: DNA
<213> ORGANISM: Siraitia grosvenorii

<400> SEQUENCE: 20
atggaagaca ccttcctact ctatccttcc ctctctcttc tctttcttct ttttgctttc     60
aagctcatcc gtcgatccgg aggagttcgc aggaacttac cgccgagtcc gccctctctt    120
ccggttatcg gccacctcca tctcttgaaa aagccactcc accggacttt ccagaaactt    180
tccgccaaat atggtcctgt tatgtccctc cgcctcgggt ctcgcctcgc agtcattgta    240
tcgtcgtcgt cggcggtgga cgagtgtttc actaaaaacg acgtcgtgct cgccaaccgt    300
cctcgtttgc taattggcaa acacctcggc tacaactaca ctaccatggt tggggctccc    360
tacggcgacc actggcgtag cctccgccgc atcggtgccc tcgaaatctt ctcttcatct    420
cgcctcaaca aattcgccga catccgaagg gatgaagtag agggattgct tcgcaaactc    480
tcacgcaatt cgctccatca attctcgaaa gtggaagttc aatcggcctt gtcggagctg    540
acgttcaaca tctcgatgag aatggcggca gggaaacggt attacggaga tgacgtgacg    600
gacgaggaag aggcgagaaa gttcagagag ttaattaaac agatagtggc gctgggcgga    660
gtatcaaatc caggggattt cgtcccgatt ctgaattgga ttccgaacgg tttcgagagg    720
aagttgatcg agtgtgggaa gaagacggat gcgttcttgc aggggctgat cgaggaccac    780
cggagaaaga aggaagaggg taggaacacg atgatcgatc acctgctctc tctgcaagaa    840
tcggagcctg ctcactacgg agaccaaata atcaaaggat ttatactggt gttactgacg    900
gcggggaccg atacatcggc cgtgacaatg gagtgggcgc tatctcatct cctgaacaat    960
cctgaagtgc taagaaggc aagagatgag gtcgacactg aaattggaca agaacgactt   1020
gtcgaagaat cagacgtagt atctaagtta ccctatcttc aagggatcat ctccgagact   1080
ctccggctga atcccgccgc tccgatgttg ttgccccatt acgcctcgga cgactgcacg   1140
atatgtggat acgacgtgcc acgtgacaca atcgtaatgg tcaatgcatg ggccatacat   1200
agggatccaa acgaatggga ggagcccacg tgtttcagac cagaacgata tgaaaagtcg   1260
tcgtcggaag cggaggtaca caagtcggtg agtttcgggg tgggaaggcg agcttgtcct   1320
```

```
gggtctggca tggcgcagag ggtgatgggc ttgactttgg cggcactggt tcagtgcttc    1380
gagtgggaga gagttggaga agaagaagtg gacatgaacg aaggctcagg tgccacaatg    1440
cccaagatgg tgccattgga ggccatgtgc agagctcgtc ccatcgtcca caaccttctt    1500
tactga                                                               1506
```

<210> SEQ ID NO 21
<211> LENGTH: 496
<212> TYPE: PRT
<213> ORGANISM: Arabidopsis thaliana

<400> SEQUENCE: 21

```
Met Ala Thr Glu Lys Thr His Gln Phe His Pro Ser Leu His Phe Val
1               5                   10                  15

Leu Phe Pro Phe Met Ala Gln Gly His Met Ile Pro Met Ile Asp Ile
            20                  25                  30

Ala Arg Leu Leu Ala Gln Arg Gly Val Thr Ile Thr Ile Val Thr Thr
        35                  40                  45

Pro His Asn Ala Ala Arg Phe Lys Asn Val Leu Asn Arg Ala Ile Glu
    50                  55                  60

Ser Gly Leu Ala Ile Asn Ile Leu His Val Lys Phe Pro Tyr Gln Glu
65                  70                  75                  80

Phe Gly Leu Pro Glu Gly Lys Glu Asn Ile Asp Ser Leu Asp Ser Thr
                85                  90                  95

Glu Leu Met Val Pro Phe Phe Lys Ala Val Asn Leu Leu Glu Asp Pro
            100                 105                 110

Val Met Lys Leu Met Glu Glu Met Lys Pro Arg Pro Ser Cys Leu Ile
        115                 120                 125

Ser Asp Trp Cys Leu Pro Tyr Thr Ser Ile Ile Ala Lys Asn Phe Asn
    130                 135                 140

Ile Pro Lys Ile Val Phe His Gly Met Gly Cys Phe Asn Leu Leu Cys
145                 150                 155                 160

Met His Val Leu Arg Arg Asn Leu Glu Ile Leu Glu Asn Val Lys Ser
                165                 170                 175

Asp Glu Glu Tyr Phe Leu Val Pro Ser Phe Pro Asp Arg Val Glu Phe
            180                 185                 190

Thr Lys Leu Gln Leu Pro Val Lys Ala Asn Ala Ser Gly Asp Trp Lys
        195                 200                 205

Glu Ile Met Asp Glu Met Val Lys Ala Glu Tyr Thr Ser Tyr Gly Val
    210                 215                 220

Ile Val Asn Thr Phe Gln Glu Leu Glu Pro Pro Tyr Val Lys Asp Tyr
225                 230                 235                 240

Lys Glu Ala Met Asp Gly Lys Val Trp Ser Ile Gly Pro Val Ser Leu
                245                 250                 255

Cys Asn Lys Ala Gly Ala Asp Lys Ala Glu Arg Gly Ser Lys Ala Ala
            260                 265                 270

Ile Asp Gln Asp Glu Cys Leu Gln Trp Leu Asp Ser Lys Glu Glu Gly
        275                 280                 285

Ser Val Leu Tyr Val Cys Leu Gly Ser Ile Cys Asn Leu Pro Leu Ser
    290                 295                 300

Gln Leu Lys Glu Leu Gly Leu Gly Leu Glu Glu Ser Arg Arg Ser Phe
305                 310                 315                 320

Ile Trp Val Ile Arg Gly Ser Glu Lys Tyr Lys Glu Leu Phe Glu Trp
                325                 330                 335
```

```
Met Leu Glu Ser Gly Phe Glu Arg Ile Lys Glu Arg Gly Leu Leu
                340                 345                 350

Ile Lys Gly Trp Ala Pro Gln Val Leu Ile Leu Ser His Pro Ser Val
355                 360                 365

Gly Gly Phe Leu Thr His Cys Gly Trp Asn Ser Thr Leu Glu Gly Ile
370                 375                 380

Thr Ser Gly Ile Pro Leu Ile Thr Trp Pro Leu Phe Gly Asp Gln Phe
385                 390                 395                 400

Cys Asn Gln Lys Leu Val Val Gln Val Leu Lys Ala Gly Val Ser Ala
                405                 410                 415

Gly Val Glu Glu Val Met Lys Trp Gly Glu Asp Lys Ile Gly Val
                420                 425                 430

Leu Val Asp Lys Glu Gly Val Lys Lys Ala Val Glu Glu Leu Met Gly
                435                 440                 445

Asp Ser Asp Asp Ala Lys Glu Arg Arg Arg Val Lys Glu Leu Gly
                450                 455                 460

Glu Leu Ala His Lys Ala Val Glu Lys Gly Gly Ser Ser His Ser Asn
465                 470                 475                 480

Ile Thr Leu Leu Leu Gln Asp Ile Met Gln Leu Ala Gln Phe Lys Asn
                485                 490                 495
```

```
<210> SEQ ID NO 22
<211> LENGTH: 495
<212> TYPE: PRT
<213> ORGANISM: Arabidopsis thaliana

<400> SEQUENCE: 22
```

```
Met Val Ser Glu Thr Thr Lys Ser Ser Pro Leu His Phe Val Leu Phe
1               5                   10                  15

Pro Phe Met Ala Gln Gly His Met Ile Pro Met Val Asp Ile Ala Arg
                20                  25                  30

Leu Leu Ala Gln Arg Gly Val Ile Ile Thr Ile Val Thr Thr Pro His
                35                  40                  45

Asn Ala Ala Arg Phe Lys Asn Val Leu Asn Arg Ala Ile Glu Ser Gly
            50                  55                  60

Leu Pro Ile Asn Leu Val Gln Val Lys Phe Pro Tyr Leu Glu Ala Gly
65              70                  75                  80

Leu Gln Glu Gly Gln Glu Asn Ile Asp Ser Leu Asp Thr Met Glu Arg
                85                  90                  95

Met Ile Pro Phe Phe Lys Ala Val Asn Phe Leu Glu Glu Pro Val Gln
                100                 105                 110

Lys Leu Ile Glu Glu Met Asn Pro Arg Pro Ser Cys Leu Ile Ser Asp
                115                 120                 125

Phe Cys Leu Pro Tyr Thr Ser Lys Ile Ala Lys Lys Phe Asn Ile Pro
                130                 135                 140

Lys Ile Leu Phe His Gly Met Gly Cys Phe Cys Leu Leu Cys Met His
145                 150                 155                 160

Val Leu Arg Lys Asn Arg Glu Ile Leu Asp Asn Leu Lys Ser Asp Lys
                165                 170                 175

Glu Leu Phe Thr Val Pro Asp Phe Pro Asp Arg Val Glu Phe Thr Arg
                180                 185                 190

Thr Gln Val Pro Val Glu Thr Tyr Val Pro Ala Gly Asp Trp Lys Asp
                195                 200                 205

Ile Phe Asp Gly Met Val Glu Ala Asn Glu Thr Ser Tyr Gly Val Ile
```

```
                 210                 215                 220

Val Asn Ser Phe Gln Glu Leu Glu Pro Ala Tyr Ala Lys Asp Tyr Lys
225                 230                 235                 240

Glu Val Arg Ser Gly Lys Ala Trp Thr Ile Gly Pro Val Ser Leu Cys
                245                 250                 255

Asn Lys Val Gly Ala Asp Lys Ala Glu Arg Gly Asn Lys Ser Asp Ile
            260                 265                 270

Asp Gln Asp Glu Cys Leu Lys Trp Leu Asp Ser Lys Lys His Gly Ser
        275                 280                 285

Val Leu Tyr Val Cys Leu Gly Ser Ile Cys Asn Leu Pro Leu Ser Gln
    290                 295                 300

Leu Lys Glu Leu Gly Leu Gly Leu Glu Glu Ser Gln Arg Pro Phe Ile
305                 310                 315                 320

Trp Val Ile Arg Gly Trp Glu Lys Tyr Lys Glu Leu Val Glu Trp Phe
                325                 330                 335

Ser Glu Ser Gly Phe Glu Asp Arg Ile Gln Asp Arg Gly Leu Leu Ile
            340                 345                 350

Lys Gly Trp Ser Pro Gln Met Leu Ile Leu Ser His Pro Ser Val Gly
        355                 360                 365

Gly Phe Leu Thr His Cys Gly Trp Asn Ser Thr Leu Glu Gly Ile Thr
    370                 375                 380

Ala Gly Leu Pro Leu Leu Thr Trp Pro Leu Phe Ala Asp Gln Phe Cys
385                 390                 395                 400

Asn Glu Lys Leu Val Val Glu Val Leu Lys Ala Gly Val Arg Ser Gly
                405                 410                 415

Val Glu Gln Pro Met Lys Trp Gly Glu Glu Lys Ile Gly Val Leu
            420                 425                 430

Val Asp Lys Glu Gly Val Lys Lys Ala Val Glu Leu Met Gly Glu
        435                 440                 445

Ser Asp Asp Ala Lys Glu Arg Arg Arg Ala Lys Glu Leu Gly Asp
    450                 455                 460

Ser Ala His Lys Ala Val Glu Glu Gly Gly Ser Ser His Ser Asn Ile
465                 470                 475                 480

Ser Phe Leu Leu Gln Asp Ile Met Glu Leu Ala Glu Pro Asn Asn
                485                 490                 495

<210> SEQ ID NO 23
<211> LENGTH: 495
<212> TYPE: PRT
<213> ORGANISM: Arabidopsis thaliana

<400> SEQUENCE: 23

Met Ala Phe Glu Lys Asn Asn Glu Pro Phe Pro Leu His Phe Val Leu
1               5                   10                  15

Phe Pro Phe Met Ala Gln Gly His Met Ile Pro Met Val Asp Ile Ala
                20                  25                  30

Arg Leu Leu Ala Gln Arg Gly Val Leu Ile Thr Ile Val Thr Thr Pro
            35                  40                  45

His Asn Ala Ala Arg Phe Lys Asn Val Leu Asn Arg Ala Ile Glu Ser
        50                  55                  60

Gly Leu Pro Ile Asn Leu Val Gln Val Lys Phe Pro Tyr Gln Glu Ala
65                  70                  75                  80

Gly Leu Gln Glu Gly Gln Glu Asn Met Asp Leu Leu Thr Thr Met Glu
                85                  90                  95
```

```
Gln Ile Thr Ser Phe Phe Lys Ala Val Asn Leu Leu Lys Glu Pro Val
                100                 105                 110

Gln Asn Leu Ile Glu Glu Met Ser Pro Arg Pro Ser Cys Leu Ile Ser
            115                 120                 125

Asp Met Cys Leu Ser Tyr Thr Ser Glu Ile Ala Lys Lys Phe Lys Ile
        130                 135                 140

Pro Lys Ile Leu Phe His Gly Met Gly Cys Phe Cys Leu Leu Cys Val
145                 150                 155                 160

Asn Val Leu Arg Lys Asn Arg Glu Ile Leu Asp Asn Leu Lys Ser Asp
                165                 170                 175

Lys Glu Tyr Phe Ile Val Pro Tyr Phe Pro Asp Arg Val Glu Phe Thr
            180                 185                 190

Arg Pro Gln Val Pro Val Glu Thr Tyr Val Pro Ala Gly Trp Lys Glu
        195                 200                 205

Ile Leu Glu Asp Met Val Glu Ala Asp Lys Thr Ser Tyr Gly Val Ile
210                 215                 220

Val Asn Ser Phe Gln Glu Leu Glu Pro Ala Tyr Ala Lys Asp Phe Lys
225                 230                 235                 240

Glu Ala Arg Ser Gly Lys Ala Trp Thr Ile Gly Pro Val Ser Leu Cys
                245                 250                 255

Asn Lys Val Gly Val Asp Lys Ala Glu Arg Gly Asn Lys Ser Asp Ile
            260                 265                 270

Asp Gln Asp Glu Cys Leu Glu Trp Leu Asp Ser Lys Glu Pro Gly Ser
        275                 280                 285

Val Leu Tyr Val Cys Leu Gly Ser Ile Cys Asn Leu Pro Leu Ser Gln
290                 295                 300

Leu Leu Glu Leu Gly Leu Gly Leu Glu Glu Ser Gln Arg Pro Phe Ile
305                 310                 315                 320

Trp Val Ile Arg Gly Trp Glu Lys Tyr Lys Glu Leu Val Glu Trp Phe
                325                 330                 335

Ser Glu Ser Gly Phe Glu Asp Arg Ile Gln Asp Arg Gly Leu Leu Ile
            340                 345                 350

Lys Gly Trp Ser Pro Gln Met Leu Ile Leu Ser His Pro Ser Val Gly
        355                 360                 365

Gly Phe Leu Thr His Cys Gly Trp Asn Ser Thr Leu Glu Gly Ile Thr
370                 375                 380

Ala Gly Leu Pro Met Leu Thr Trp Pro Leu Phe Ala Asp Gln Phe Cys
385                 390                 395                 400

Asn Glu Lys Leu Val Val Gln Ile Leu Lys Val Gly Val Ser Ala Glu
                405                 410                 415

Val Lys Glu Val Met Lys Trp Gly Glu Glu Lys Ile Gly Val Leu
            420                 425                 430

Val Asp Lys Glu Gly Val Lys Lys Ala Val Glu Glu Leu Met Gly Glu
        435                 440                 445

Ser Asp Asp Ala Lys Glu Arg Arg Arg Ala Lys Glu Leu Gly Glu
450                 455                 460

Ser Ala His Lys Ala Val Glu Glu Gly Gly Ser Ser His Ser Asn Ile
465                 470                 475                 480

Thr Phe Leu Leu Gln Asp Ile Met Gln Leu Ala Gln Ser Asn Asn
                485                 490                 495

<210> SEQ ID NO 24
<211> LENGTH: 495
<212> TYPE: PRT
```

<213> ORGANISM: Stevia rebaudiana

<400> SEQUENCE: 24

```
Met Ser Pro Lys Met Val Ala Pro Pro Thr Asn Leu His Phe Val Leu
1               5                   10                  15

Phe Pro Leu Met Ala Gln Gly His Leu Val Pro Met Val Asp Ile Ala
            20                  25                  30

Arg Ile Leu Ala Gln Arg Gly Ala Thr Val Thr Ile Ile Thr Thr Pro
        35                  40                  45

Tyr His Ala Asn Arg Val Arg Pro Val Ile Ser Arg Ala Ile Ala Thr
    50                  55                  60

Asn Leu Lys Ile Gln Leu Leu Glu Leu Gln Leu Arg Ser Thr Glu Ala
65                  70                  75                  80

Gly Leu Pro Glu Gly Cys Glu Ser Phe Asp Gln Leu Pro Ser Phe Glu
                85                  90                  95

Tyr Trp Lys Asn Ile Ser Thr Ala Ile Asp Leu Leu Gln Gln Pro Ala
            100                 105                 110

Glu Asp Leu Leu Arg Glu Leu Ser Pro Pro Asp Cys Ile Ile Ser
        115                 120                 125

Asp Phe Leu Phe Pro Trp Thr Thr Asp Val Ala Arg Arg Leu Asn Ile
130                 135                 140

Pro Arg Leu Val Phe Asn Gly Pro Gly Cys Phe Tyr Leu Leu Cys Ile
145                 150                 155                 160

His Val Ala Ile Thr Ser Asn Ile Leu Gly Glu Asn Glu Pro Val Ser
                165                 170                 175

Ser Asn Thr Glu Arg Val Val Leu Pro Gly Leu Pro Asp Arg Ile Glu
            180                 185                 190

Val Thr Lys Leu Gln Ile Val Gly Ser Ser Arg Pro Ala Asn Val Asp
        195                 200                 205

Glu Met Gly Ser Trp Leu Arg Ala Val Glu Ala Glu Lys Ala Ser Phe
210                 215                 220

Gly Ile Val Val Asn Thr Phe Glu Glu Leu Glu Pro Glu Tyr Val Glu
225                 230                 235                 240

Glu Tyr Lys Thr Val Lys Asp Lys Lys Met Trp Cys Ile Gly Pro Val
                245                 250                 255

Ser Leu Cys Asn Lys Thr Gly Pro Asp Leu Ala Glu Arg Gly Asn Lys
            260                 265                 270

Ala Ala Ile Thr Glu His Asn Cys Leu Lys Trp Leu Asp Glu Arg Lys
        275                 280                 285

Leu Gly Ser Val Leu Tyr Val Cys Leu Gly Ser Leu Ala Arg Ile Ser
290                 295                 300

Ala Ala Gln Ala Ile Glu Leu Gly Leu Gly Leu Glu Ser Ile Asn Arg
305                 310                 315                 320

Pro Phe Ile Trp Cys Val Arg Asn Glu Thr Asp Glu Leu Lys Thr Trp
                325                 330                 335

Phe Leu Asp Gly Phe Glu Glu Arg Val Arg Asp Arg Gly Leu Ile Val
            340                 345                 350

His Gly Trp Ala Pro Gln Val Leu Ile Leu Ser His Pro Thr Ile Gly
        355                 360                 365

Gly Phe Leu Thr His Cys Gly Trp Asn Ser Thr Ile Glu Ser Ile Thr
370                 375                 380

Ala Gly Val Pro Met Ile Thr Trp Pro Phe Phe Ala Asp Gln Phe Leu
385                 390                 395                 400
```

```
Asn Glu Ala Phe Ile Val Glu Val Leu Lys Ile Gly Val Arg Ile Gly
                405                 410                 415

Val Glu Arg Ala Cys Leu Phe Gly Glu Asp Lys Val Gly Val Leu
            420                 425                 430

Val Lys Lys Glu Asp Val Lys Ala Val Glu Cys Leu Met Asp Glu
        435                 440                 445

Asp Glu Asp Gly Asp Gln Arg Arg Lys Arg Val Ile Glu Leu Ala Lys
    450                 455                 460

Met Ala Lys Ile Ala Met Ala Glu Gly Gly Ser Ser Tyr Glu Asn Val
465                 470                 475                 480

Ser Ser Leu Ile Arg Asp Val Thr Glu Thr Val Arg Ala Pro His
                485                 490                 495

<210> SEQ ID NO 25
<211> LENGTH: 481
<212> TYPE: PRT
<213> ORGANISM: Stevia rebaudiana

<400> SEQUENCE: 25

Met Asp Ala Met Ala Thr Thr Glu Lys Lys Pro His Val Ile Phe Ile
1               5                   10                  15

Pro Phe Pro Ala Gln Ser His Ile Lys Ala Met Leu Lys Leu Ala Gln
                20                  25                  30

Leu Leu His His Lys Gly Leu Gln Ile Thr Phe Val Asn Thr Asp Phe
            35                  40                  45

Ile His Asn Gln Phe Leu Glu Ser Ser Gly Pro His Cys Leu Asp Gly
        50                  55                  60

Ala Pro Gly Phe Arg Phe Glu Thr Ile Pro Asp Gly Val Ser His Ser
65                  70                  75                  80

Pro Glu Ala Ser Ile Pro Ile Arg Glu Ser Leu Leu Arg Ser Ile Glu
                85                  90                  95

Thr Asn Phe Leu Asp Arg Phe Ile Asp Leu Val Thr Lys Leu Pro Asp
                100                 105                 110

Pro Pro Thr Cys Ile Ile Ser Asp Gly Phe Leu Ser Val Phe Thr Ile
            115                 120                 125

Asp Ala Ala Lys Lys Leu Gly Ile Pro Val Met Met Tyr Trp Thr Leu
        130                 135                 140

Ala Ala Cys Gly Phe Met Gly Phe Tyr His Ile His Ser Leu Ile Glu
145                 150                 155                 160

Lys Gly Phe Ala Pro Leu Lys Asp Ala Ser Tyr Leu Thr Asn Gly Tyr
                165                 170                 175

Leu Asp Thr Val Ile Asp Trp Val Pro Gly Met Glu Gly Ile Arg Leu
                180                 185                 190

Lys Asp Phe Pro Leu Asp Trp Ser Thr Asp Leu Asn Asp Lys Val Leu
            195                 200                 205

Met Phe Thr Thr Glu Ala Pro Gln Arg Ser His Lys Val Ser His His
        210                 215                 220

Ile Phe His Thr Phe Asp Glu Leu Glu Pro Ser Ile Ile Lys Thr Leu
225                 230                 235                 240

Ser Leu Arg Tyr Asn His Ile Tyr Thr Ile Gly Pro Leu Gln Leu Leu
                245                 250                 255

Leu Asp Gln Ile Pro Glu Glu Lys Lys Gln Thr Gly Ile Thr Ser Leu
                260                 265                 270

His Gly Tyr Ser Leu Val Lys Glu Glu Pro Glu Cys Phe Gln Trp Leu
            275                 280                 285
```

```
Gln Ser Lys Glu Pro Asn Ser Val Val Tyr Val Asn Phe Gly Ser Thr
    290                 295                 300

Thr Val Met Ser Leu Glu Asp Met Thr Glu Phe Gly Trp Gly Leu Ala
305                 310                 315                 320

Asn Ser Asn His Tyr Phe Leu Trp Ile Ile Arg Ser Asn Leu Val Ile
                325                 330                 335

Gly Glu Asn Ala Val Leu Pro Pro Glu Leu Glu Glu His Ile Lys Lys
            340                 345                 350

Arg Gly Phe Ile Ala Ser Trp Cys Ser Gln Glu Lys Val Leu Lys His
        355                 360                 365

Pro Ser Val Gly Gly Phe Leu Thr His Cys Gly Trp Gly Ser Thr Ile
    370                 375                 380

Glu Ser Leu Ser Ala Gly Val Pro Met Ile Cys Trp Pro Tyr Ser Trp
385                 390                 395                 400

Asp Gln Leu Thr Asn Cys Arg Tyr Ile Cys Lys Glu Trp Glu Val Gly
                405                 410                 415

Leu Glu Met Gly Thr Lys Val Lys Arg Asp Glu Val Lys Arg Leu Val
            420                 425                 430

Gln Glu Leu Met Gly Gly Gly His Lys Met Arg Asn Lys Ala Lys
        435                 440                 445

Asp Trp Lys Glu Lys Ala Arg Ile Ala Ile Ala Pro Asn Gly Ser Ser
    450                 455                 460

Ser Leu Asn Ile Asp Lys Met Val Lys Glu Ile Thr Val Leu Ala Arg
465                 470                 475                 480

Asn

<210> SEQ ID NO 26
<211> LENGTH: 1380
<212> TYPE: DNA
<213> ORGANISM: Siraitia grosvenorii

<400> SEQUENCE: 26
atggatgccc agcgaggtca caccaccacc attttgatgc ttccatgggt cggctacggc    60
catctcttgc ctttcctcga gctggccaaa agcctctcca ggaggaaatt attccacatc   120
tacttctgtt caacgtctgt tagcctcgac gccattaaac caaagcttcc tccttctatc   180
tcttctgatg attccatcca acttgtggaa cttcgtctcc cttcttctcc tgagttacct   240
cctcatcttc acacaaccaa cggccttccc tctcacctca tgcccgctct ccaccaagcc   300
ttcgtcatgg ccgcccaaca ctttcaggtc attttacaaa cacttgcccc gcatctcctc   360
atttatgaca ttctccaacc ttgggctcct caagtggctt catccctcaa cattccagcc   420
atcaacttca gtactaccgg agcttcaatg ctttctcgaa cgcttcaccc tactcactac   480
ccaagttcta aattcccaat ctcagagttt gttcttcaca atcactggag agccatgtac   540
accaccgccg atgggctct acagaagaa ggccacaaaa ttgaagaaac acttgcgaat   600
tgcttgcata cttcttgcgg ggtagttttg gtcaatagtt tcagagagct tgagacgaaa   660
tatatcgatt atctctctgt tctcttgaac aagaaagttg ttccggtcgg tcctttggtt   720
tacgaaccga atcaagaagg ggaagatgaa ggttattcaa gcatcaaaaa ttggcttgac   780
aaaaaggaac cgtcctcaac cgtcttcgtt tcatttggaa ccgaatactt cccgtcaaag   840
gaagaaatgg aagagatagc gtatgggtta gagctgagcg aggttaattt catctgggtc   900
cttagatttc ctcaaggaga cagcaccagc accattgaag acgccttgcc gaagggggttt   960
```

```
ctggagagag cgggagagag ggcgatggtg gtgaagggtt gggctcctca ggcgaagata   1020
ctgaagcatt ggagcacagg ggggcttgtg agtcactgtg gatggaactc gatgatggag   1080
ggcatgatgt ttggcgtacc cataatagcg gtcccgatgc atctggacca gcccttttaac  1140 gccggactct tggaagaagc tggcgtcggc gtggaagcca agcgaggttc ggacggcaaa   1200
attcaaagag aagaagttgc aaagtcgatc aaagaagtgg tgattgagaa aaccagggaa   1260
gacgtgagga agaaagcaag agaaatgggt gagattttga ggagtaaagg agatgagaaa   1320
attgatgagt tggtggctga aatttctctt ttgcgcaaaa aggctccatg ttcaatttaa   1380
```

<210> SEQ ID NO 27
<211> LENGTH: 1434
<212> TYPE: DNA
<213> ORGANISM: Siraitia grosvenorii

<400> SEQUENCE: 27

```
atgcttccat ggctggctca cggccatgtc tcccctttct tcgagctcgc caagttgctc     60
gccgctagaa acttccacat attcttctgc tccaccgccg taaacctccg ctccgtcgaa    120
ccaaaactct ctcagaagct ctcctcccac gtggagctgg tggagctcaa cctaccgccc    180
tcgccggagc tccctccgca ccgccacacc accgccggcc ttccaccgca cctcatgttc    240
tcgctcaagc gagctttcga catggccgct cccgccttcg ccgccatcct ccgcgacctg    300
aacccggact tgctcatcta cgacttcctg cagccgtggg cggcggcgga ggctctgtcg    360
gcggatattc cggccgtgat gttcaaaagc acgggtgcgc tcatggcggc catggtcgcg    420
tacgagctga cgtttccgaa ctctgatttt ttctcgcttt ccctgagat cgtctctcc     480 gagtgcgaga ttaaacagct gaagaacttg tttcaatgtt ctgtgaatga tgcgaaagac    540
aagcaaagga ttaagggatg ttatgagaga tcttgcggca tgattttggt gaaatctttc    600
agagaaatcg aaggcaaata tattgatttt ctctctactc tgctgggcaa gaaggttgtt    660
ccagttggtc cacttgttca acaaacagaa gacgacgtcg tatcaggaag ttttgacgaa    720
tggctaaatg gaaaagatag atcgtcttcc atactcgtgt ctttcggaag cgagttctac    780
ctgtccagag aagacatgga agagatcgcg catggcttag agctgagcca ggtgaacttc    840
atatgggtcg tcaggtttcc ggcgggagga gagagaaaca cgacaaaggt ggaagaagaa    900
ctgccaaaag ggtttctaga gagttaga gagagaggga tggtggtgga gggctgggcg     960
ccgcaggctc agatcttgaa acatccaagc gtcggcggat tcctcagcca ctgcgggtgg    1020
agctccgtcg tggagagcat gaaattcggc gttccgatca tcgccatgcc gatgcacctc    1080
gaccagccgc tgaattcccg gctggtcgag cggctcggcg tcggcgtagt ggtggagaga    1140
gacggccgcc tccggggaga ggtggagaga gttgtcagag aggtggtggt ggagaaaagt    1200
ggagagagag tgaggaagaa ggtggaggag tttgcagaga tcatgaagaa gaaaaaagac    1260
aatgaagaga tggacgtagt cgtggaagag ttggtgacgc tctgcaggaa gaagaagaag    1320
gaggaggatt tacagagtaa ttattggtgc agaaccgcca ttgatgacca ttgttctgaa    1380
gtcgtgaaga ttgaagatgc tgcagcagcc gacgaggagc ctctttgcaa ataa           1434
```

<210> SEQ ID NO 28
<211> LENGTH: 1383
<212> TYPE: DNA
<213> ORGANISM: Siraitia grosvenorii

<400> SEQUENCE: 28

```
atggctgtca cttacagcct gcacatagca atgtacccctt ggtttgcttt cggccacttg    60
```

```
actccatttc tccaagtctc caacaagctt gccaaggaag gccacaaaat ctccttcttc      120
atcccaacga aaacgctaac caaattgcag cctttcaatc tctttccaga tctcattacc      180
tttgtcccca tcactgttcc tcatgttgat ggtctccctc ttggagctga gactactgct      240
gatgtttctc acccttcaca gctcagtctc atcatgactc tatggattg cacccaaccc      300 gaaatcgagt gtcttcttcg agacataaaa cctgatgcca tcttcttcga tttcgcgcac      360
tgggtgccaa aattggcatg tggattgggc attaagtcga ttgattacag tgtctgttct      420
gcagtatcaa ttggttatgt tttgcccta ttaaggaaag tttgtggaca agatttatta      480
actgaagatg attttatgca gccatctcct ggctacccga gttccaccat caatcttcaa      540
gctcatgagg ctcgatattt tgcatctctg agccgctgga ggtttggcag tgatgtccct      600
ttctttagtc gccatcttac tgcacttaat gaatgcaatg ctttagcatt caggtcatgt      660
agggagattg aagggccttt tatagactat ccagaaagtg aattaaaaaa gcctgtgttg      720
ctttccggag cagtggatct acaaccgcca accacaactg tagaagaaag atgggcaaaa      780
tggctatcag ggttcaacac cgactcggtc gtatattgtg catttggaag tgagtgtacc      840
ttagcaaaag accaattcca agaactgctg ttgggttttg agctttcaaa tatgccattc      900
tttgctgcac ttaaaccacc ttttggtgtt gactcggttg aagcagcctt gcctgaaggt      960
tttgaacaga gagttcaggg aagagggggtg gtctatgggg gatgggtcca acagcagctc     1020
attttggagc acccatcaat tggatgcttt gttacacatt gtggatcagg ctccttatca     1080
gaggcgttag tgaagaagtg tcaattagtg ttgttacctc gtatcggtga ccactttttc     1140
cgagcaagaa tgttgagcaa ttatttgaaa gttggtgtgg aggtagagaa aggagaagga     1200
gatggatctt ttacaaagga aagtgtgtgg aaggcagtga agacagtgat ggatgaagag     1260
aatgaaactg ggaaagagtt cagagcgaac cgtgccaaga taagagagct attgctcgac     1320
gaagatctcg aggagtctta tatcaacaat ttcatccaca gcctgcatac tttgaatgca     1380
tga                                                                   1383
```

<210> SEQ ID NO 29
<211> LENGTH: 174
<212> TYPE: DNA
<213> ORGANISM: Artificial sequence
<220> FEATURE:
<223> OTHER INFORMATION: Partial gene sequence from Siraitia grosvenorii

<400> SEQUENCE: 29

```
atggcggatc ggaaagagag cgttgtgatg ttcccgttca tggggcaggg ccatatcatc       60
ccttttctag ctttggccct ccagattgag cacagaaaca gaaactacgc catatacttg      120
gtaaatactc ctctcaacgt taagaaaatg agatcttctc tccctccaga ttga            174
```

<210> SEQ ID NO 30
<211> LENGTH: 1347
<212> TYPE: DNA
<213> ORGANISM: Siraitia grosvenorii

<400> SEQUENCE: 30

```
atggaagcta agaactgcaa aaaggttctg atgttcccat ggctggcgca tggtcacata       60
tcaccatttg tagagctggc caagaagctc acagacaaca acttcgccgt ttttctatgt      120
tcttcccctg caaatcttca aaacgtcaag ccaaaactcc cccatcacta ctctgattcc      180
attgaactcg tggagctcaa ccttccatcg tcgccggagc ttccccctca tatgcacacc      240
```

```
accaatggcc tcccttttgca tttagttccc accctcgttg acgccttgga catggccgct    300
ccgcacttct ccgccatttt acaggaactg aatccagatt ttctcatatt cgacatcttc    360
caaccctggg cggctgaaat cgcttcctcc ttcggcgttc ctgctatttt gttgcttatc    420
gttggatctg ctataaccgc tttaggggtt cattttgtcc ggagctccgg tacggaattc    480
cccttteccg agcttactaa atcattcaag aaggaggacg accgaaaacc tccaggagat    540
tccggcaacg atagaggaaa acggctattc aaatgtctgc tggacctgga acattcttca    600
gagactattt tggtgaacag ttttacagag atagagggca aatatatgga ctatctctcg    660
gtcttactga agaagaagat ccttccgatt ggtcctttgg ttcagaaaat ggctccgat     720
gacgatgaat cgggaatcct ccggtggctt gacaagaaga aaccgaattc aactgtgtac    780
gtttcgttcg ggagtgagta ctatttgagc aaagaagaca tagcagagct tgcgcatggt    840
ctggaaatca gcggcgtcaa tttcatctgg attgttcggt ttccaaaggg agagaaaatc    900
gccattgaag aggcattacc agatgaaatt cttgaaagag tcggagagag aggcgtcgtc    960
gttgatggat gggcgccgca gatgaaaata ttagggcatt cgagcgtcgg cgggtttctg   1020
tctcactgcg gatggaactc tgtgctggag agtctggtgc tcggcgtgcc gatcatatcc   1080
ctgccgatac acctcgaaca gccgtggaac gccttggtag cggagcacgt cggcgtttgt   1140
gtgagggcga agagacga cggaggaaat cttcaaagag agttggtggc ggaggccatt     1200
aaagaagtgg tggttgagga acaggacgcg gaactgagaa gcaaagcaag agtaattagt   1260
gaaatcttga aaataaaga agctgaaaca atacaagatt tggtggctga gcttcaccgg    1320
ctttctgacg caagaagagc ttgttga                                        1347

<210> SEQ ID NO 31
<211> LENGTH: 1389
<212> TYPE: DNA
<213> ORGANISM: Siraitia grosvenorii

<400> SEQUENCE: 31
atggaaaaaa atcttcacat agtgatgctt ccatggtcgg cgttcggcca tctcatacca     60
ttttttcacc tctccatagc cttagccaaa gccaaagttt atatctcctt cgtctccact    120
ccaagaaata ttcagagact yccccaaatc ccgccggact tagcttcttt catagatttg    180
gtggccattc ccttgccgag actcgacgac gatctgttgc tagaatctgc agaggccact    240
tctgatattc cgatcgacaa gattcagtat ttgaagcgag ccgtcgacct cctccgccac    300
cccttcaaga gtttgtcgc cgaacaatcg ccggactggg tcgtcgttga ttttcatgct    360
tattgggccg cgagatctta ccaggagttt caagttcccg tcgcctactt ctgtattttc    420
tcggccatct gtttgcttta tcttggacct ccagacgtgt attcgaagga tcctcagatc    480
atggcacgaa tatctcccgt taccatgacg gtgccgccgg agtgggtcgg ttttccgtcc    540
gccgtagcct acaacttgca tgaggcgacg gtcatgtact ctgctctcta tgaaacaaat    600
gggtctggaa taagcgactg cgagaggatt cgccggctcg tcctttcctg tcaagccgtg    660
gccattcgaa gctgcgagga gattgaaggc gaatacctta ggttatgtaa gaaactgatt    720
ccaccgcagg ggattgccgt cggcttgctt ccgccggaaa agccaccaaa atcagatcac    780
gagctcatca aatggcttga cgagcaaaag ctccgattcg tcgtgtacgt gacattcggc    840
agcgaatgca acctgacgaa ggaccaagtt cacgagatag cccacgggct ggaactgtcg    900
gagctgccat ttttatgggc actgaggaaa cccagctggg cagctgagga agacgatggg    960
ctgccgtctg ggtttcgtga gagaacgtcc gggagagggg tggtgagcat ggagtgggtg   1020
```

```
ccgcagttgg agattctggc gcaccaggcc atcggcgtct ctttagttca cgggggctgg    1080
ggctctatta tcgagtcgct acaagctggg cactgtctgg ttgtgctgcc gtttatcatc    1140
gaccagccgc tgaactcaaa gcttttggtg gagaaaggga tggcgcttga gatcagaagg    1200
aacggttctg atggatggtt tagtagagaa gacatcgccg gaactttgag agaagctatg    1260
cggtcgtctg aggaaggcgg gcagctgagg agccgtgcaa agaggcggc ggccatcgtt     1320 ggagatgaga agctgcagtg gaacaatac ttcggcgcgt tcgtacagtt tctgagggac     1380
aagtcttga                                                            1389
```

<210> SEQ ID NO 32
<211> LENGTH: 1395
<212> TYPE: DNA
<213> ORGANISM: Siraitia grosvenorii

<400> SEQUENCE: 32

```
atgtccgagg agaaaggcag agggcacagc tcgtcgacgg agagacacac tgctgccgcc     60
atgaacgccg agaaacgaag caccaaaatc ttgatgctcc catggctggc tcacggccac    120
atatctccat acttcgagct cgccaagagg ctcaccaaga aaaactgcca cgtttacttg    180
tgttcttcgc ctgtaaatct ccaaggcatc aagccgaaac tctctgaaaa ttactcttcc    240
tccattgaac ttgtggagct tcatcttcca tctctccccg accttcctcc ccatatgcac    300
acgaccaaag gcatccctct acatctacaa tccaccctca tcaaagcctt cgacatggcc    360 gccccctgatt tttccgacct gttgcagaaa ctcgagccgg atctcgtcat ttccgatctc    420
ttccagccat gggcagttca attagcgtcg tctcggaaca ttcccgtcgt caatttcgtt    480
gtcaccggag tcgctgttct tagtcgtttg gctcacgtgt tttgcaactc cgttaaggaa    540
ttccctttcc cggaactcga tctaaccgac cattggatct ccaagagccg ccgcaaaacg    600
tccgacgaat taggtcgcga gtgcgcgatg cgatttttca actgcatgaa acaatcttca    660
aacatcactc tagccaacac ttttccccgag ttcgaagaaa aatacatcga ttatctctct   720
tcctcgttta agaaaaagat tcttccggtt gctcctctag ttcctgaaat cgacgcagac    780
gacgagaaat cggaaattat cgagtggctt gacaagaaga aaccgaaatc gactgtttac    840
gtttcgtttg ggagtgagta ttatctgacg aaagaagaca gggaagagct cgcccatggc    900
ttagaaaaga gcggcgtgaa tttcatctgg gttattaggt ttccaaaggg cgagaagatc    960
accattgaag aggctttacc agaaggattt ctcgagagag tagggacag gggagtgatt   1020 atcgacgggt gggcgccgca gttgaaaata ttgaggcatt caagcgtggg cgggttcgtg   1080
tgccactgcg ggtggaactc tgtggtggag agcgtggtgt ttggggtgcc gatcatagcc   1140
ttgccgatgc agctcgatca gccatggcat gcgaaggtgg cggaggacgg cggcgtctgt   1200
gcggaggcga agagagacgt tgaagggagc gttcagagag aagaggtggc gaaggccatt   1260
aaagaggtgg tgtttgagaa gaggggggg gttctgagtg aaaagcaag agagatcagc     1320 gaggccttga gaaagaggga aggggaaatc atagaggaat tggttgctga gtttcaccag   1380
ctctgtgaag cttga                                                    1395
```

<210> SEQ ID NO 33
<211> LENGTH: 1242
<212> TYPE: DNA
<213> ORGANISM: Artificial sequence
<220> FEATURE:
<223> OTHER INFORMATION: Partial gene sequence from Siraitia grosvenorii

<400> SEQUENCE: 33

```
ttctgctcca cgcctgtaaa tttggaagcc attaaaccaa agctttccaa aagctactct      60
gattcgatcc aactaatgga ggttcctctc gaatcgacgc cggagcttcc tcctcactat     120
catacagcca aaggccttcc gccgcattta atgcccaaac tcatgaatgc ctttaaaatg     180
gttgctccca atctcgaatc gatcctaaaa accctaaacc cagatctgct catcgtcgac     240
attctccttc catggatgct tccactcgct tcatcgctca aaattccgat ggttttcttc     300
actattttcg gtgccatggc catctccttt atgatttata atcgaaccgt ctcgaacgag     360
cttccatttc cagaatttga acttcacgag tgctggaaat cgaagtgccc ctatttgttc     420
aaggaccaag cggaaagtca atcgttctta gaatacttgg atcaatcttc aggcgtaatt     480
ttgatcaaaa cttccagaga gattgaggct aagtatgtag actttctcac ttcgtcgttt     540
acgaagaagg ttgtgaccac cggtcccctg gttcagcaac cttcttccgg cgaagacgag     600
aagcagtact ccgatatcat cgaatggcta gacaagaagg agccgttatc gacggtgctc     660
gtttcgtttg ggagcgagta ttatctgtca aggaagagat ggaagaaat cgcctacggg      720
ctggagagcg ccagcgaggt gaatttcatc tggattgtta ggtttccgat gggacaggaa     780
acggaggtcg aggcggcgct gccggagggg ttcatccaga gggcaggaga gagagggaaa     840
gtggtcgagg gctgggctcc gcaggcgaaa atattggcgc atccgagcac cggcggccat     900
gtgagccaca acgggtggag ctcgattgtg gagtgcttga tgtccggtgt accggtgatc     960
ggcgcgccga tgcaacttga cgggccaatc gtcgcaaggc tggtggagga gatcggcgtg    1020
ggtttggaaa tcaagagaga tgaggaaggg agaatcacga ggggcgaagt tgccgatgca    1080
atcaagacgg tggcggtggg caaaaccggg gaagatttta aaggaaagc aaaaaaaatc     1140
agcagcattt tgaagatgaa agatgaagaa gaggttgaca cttttggcaat ggaattagtg    1200
aggttatgcc aaatgaaaag agggcaggag tctcaggact aa                       1242
```

<210> SEQ ID NO 34
<211> LENGTH: 912
<212> TYPE: DNA
<213> ORGANISM: Artificial sequence
<220> FEATURE:
<223> OTHER INFORMATION: Partial gene sequence from Siraitia grosvenorii

<400> SEQUENCE: 34

```
tcccggtcaa cggtagagga cttcacggag cttcgagagt ggatgccttc tggatcgaac      60
atggtctacc ggtaccacga gattaaaaaa tccttagatg gagcaaccgg caacgaatcg     120
gggacgtctg attcggtccg attcggaatt gtgattgagg agagtgttgc tgtggctgta     180
agaagctccc ctgaactgga accggaatgg ttcgatttgc tcgcgaagct ttaccagaag     240
ccagttgttc cggtaggatt tctacctcca gtaattgaag atgcggaaga attgagcagc     300
gatatcaagg aatggttaga caaacagagc tcaaactcgg tcctttacgt cgcattcggg     360
accgaggcga ctctgagtca agatgacgtc actgagttag ccatgggct tgagcaatct     420
gggataccat ttttctgggt actgagaacc tcacctcggg acgagtcaga catgttaccg     480
gccgggttca aggagcgagt cgaaggtcga ggaagtgttc acgtgggatg ggtctcgcag     540
gtgaagatac tgagtcacga ctcggttggc ggttgtttga cacactgtgg atggaactcg     600
atcatagagg ggctcggatt cgggcgcgtt atggtattgt ttccagtcgt gaacgaccag     660
ggattgaacg ctagattgtt gggggagaag aagctcggga tagagataga aagggacgag    720
cgagatggat cgttcacacg cgactcggtg tcggaatcgg tgaggtcggc aatggcggaa    780
```

```
agttcaggcg aggccttgag agtgagggcc agggaaatga aggggttgtt tggaaacgga      840
gatgagaacg agcatcaact gaacaagttt gtacaatttc tcgaggcaaa caggaatagg      900
cagtccgagt aa                                                          912
```

```
<210> SEQ ID NO 35
<211> LENGTH: 1125
<212> TYPE: DNA
<213> ORGANISM: Artificial sequence
<220> FEATURE:
<223> OTHER INFORMATION: Partial gene sequence from Siraitia grosvenorii

<400> SEQUENCE: 35
ctgctgccga ttccgctgcc gaaaccggcc gccgatctct tgccggaagg tgcagaggcg       60
acggtggata ttccgtccga caagattccg tatctgaaat tggccctcga tctcgccgag      120
cagccgtttc ggaagttcgt cgttgatcgt ccgccggatt ggatgatcgt cgattttaat      180
gctacttggg tctgcgatat ttctcgggag cttcaaatcc caatcgtttt ctttcgtgtt      240
ctttcgcctg gatttcttgc tttctttgcg catgttcttg ggagtggtct gccgctgtcg      300
gagatcgaaa gcctgatgac tccgccggtg atcgacgggt cgacggtggc gtaccgccgg      360
catgaagctg ccgttatttg tgctgggttt tttgagaaga acgcttctgg tatgagtgat      420
cgcgatcggg taaccaaaat tctctctgcc agtcaagcaa tcgcagttcg ttcttgctac      480
gaatttgacg ttgagtattt gaaattgtac gagaaatatt gtggaaaaag agtgattcct      540
ctagggtttc tccctccaga aaagccccaa aagtccgagt tcgccgccga ttcgccatgg      600
aaaccgacct tcgagtggct tgacaaacaa aagccccgat cagtggtgtt cgtcggattc      660
ggcagcgaat gcaaactcac gaaagatgat gtttacgaga tagcgcgcgg ggtggagctg      720
tcggagctgc cattttttgtg ggctctgaga aaaccgatct gggcggcggc ggacgattcc      780
gacgctctgc ctgccggatt cctcgagcgg acggcggaga gagggattgt gagcatgggg      840
tgggcgccgc agatggagat tttaacgcac ccgtcgattg gcggctctct gtttcacgcc      900 gggtgtgggat ccgccattga agctctgcaa ttcgggcatt gccttgttct gttgccattc      960
atcgtggatc agccactgaa tgcaaggctt ctggtggaga agggtgttgc agtcgaagtt     1020
ggaagaaagg aagacgggtc tttagtgga gaagacatag ctaaagctct gagagaagct     1080
atggtttcag aagaaggtga gcagatgagg aggcaagcga gaaag                     1125
```

```
<210> SEQ ID NO 36
<211> LENGTH: 486
<212> TYPE: DNA
<213> ORGANISM: Artificial sequence
<220> FEATURE:
<223> OTHER INFORMATION: Partial gene sequence from Siraitia grosvenorii

<400> SEQUENCE: 36
atggaaaacg acggcgtttt gcacgtggtg gtattcccat ggctagcctt gggtcatctc       60
attcctttcg ctcgactcgc cacctgctta gcccacaagg gtctcagggt ttcgttcgta      120
tcaaccacaa ggaacctgag cagaattccc aaaatacccc cacatctctc ctcctccgtc      180
aacctcgtcg gctttcctct gccccacgtc gacggccttc cggacgccgc cgaggcttcc      240
tccgacgtgc cttacaacaa gcaacagtta ctgaagaagg ccttcgactc tctggaatca      300
ccgctcgccg atttgcttcg tgatttgaat cccgattgga ttatctacga ttacgcctct      360
cattggcttc cgcagctcgc ggcggagctc cgtatctcgt ctgttttctt cagcctcttc      420
```

```
accgcggcgt tcttgctttt tcttggccca ccgtcggcgt tgtccggcga cggcagttcc    480
cggtga                                                              486
```

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41
<211> LENGTH: 1461
<212> TYPE: DNA
<213> ORGANISM: Siraitia grosvenorii

<400> SEQUENCE: 41

```
gtggggccgt cgtctgttga agctcctcag cggacgattt cgaagcctga acagagggag     60
ctaccgttga ggaagattcc cggggactat gggccgccgt tgttgggtcc gattaaggac    120
cgacaagact attttttacaa tcaggggagg gaggagttcc tgagatcacg catgaacagg    180
tacgaatcaa ctgtgtacag aactaatatg ccaccaggtc cctttatctc ctccgattct    240
cgtgtcatcg ttttactcga cggcaagagc ttccctgtac tcttcgacgt ttctaaagtt    300
ctgaaacaag acgtcttcac cggaacttat atgcccttaa cggagctcac tggcggctac    360
cgagttcttt cttatctcga cccctccgag cccgatcacg agaagcttaa acagttcctc    420
ttctacctcc tcaagtaccg tcgcgacaag attctgccgg agtttcactc tacctttttcg    480
gagctgtttg agactctgga aggaggtg gctgccgccg gtagagcaga ttataatgat    540
cccggtgaac aggcggcgtt taacttcttg gctcggtctc tgttcggcgc caacccgccc    600
gacaccaaac tgggaaacga cgctccgagt ttaatatcca aatgggtgct gttccagctg    660
ggtccggttc tcactcttgg tcttcccaag cctgtcgagg agcttctcct gcgaaccgtc    720
cggctgccac cggcgcttgt gaaatcggat taccagcggc tgtacgattt cttttacgag    780
gcgtcggagg ctgtgtttgc ggaggcggat agattgggca ttgcgagaga ggaagcgtgt    840
cacaacttgg tcttcgccac gtgcttcaat tccttcggag ggatgaagat cctcttcccc    900
aatatgataa aatggatcgg acgtgccgga gtgaatctcc atacgagct cgcacgggag    960
ataagatccg ccgtcaaagc ccacggcggc aagatcacga tggcggctat ggaacagatg   1020
ccgctgatga gtccgtagt gtacgaaacg ctcagaatcg aaccccggt tcctgcgcaa   1080
tacgggcgag cgaaggagga cctggtgatc gagagccacg acgccgcttt cgagatcaaa   1140
gaaggggaaa tgttgtgtgg gtaccagcca ttcgccacta gagatccgaa aatattcgag   1200
```

```
agatccgaag aattcgtacc ggatcggttc accggcgacg gcgaggagtt gctgaagcac    1260
gtgctctggt caaacggacc ggagactcaa tccccaaccg ttaaagacaa gcagtgcgct    1320
ggcaaagact tcatagtctt cgtctcccgc ctcctcgtcg tcgaactctt cctccgatac    1380
gactccttcg acattgaagt cgcagcttcg ccgttgggcg ccgccgtcac cataacttcc    1440
ctgaagaagg caagctttta a                                              1461
```